US008759306B2

(12) United States Patent
Kaletta

(10) Patent No.: US 8,759,306 B2
(45) Date of Patent: Jun. 24, 2014

(54) RNAI FOR THE CONTROL OF INSECTS AND ARACHNIDS

(75) Inventor: Titus Jan Kaletta, Klein-Winternheim (DE)

(73) Assignee: Devgen N.V., Zwijnaarde (BE)

(*) Notice: Subject to any disclaimer, the term of this patent is extended or adjusted under 35 U.S.C. 154(b) by 1301 days.

(21) Appl. No.: 11/921,370

(22) PCT Filed: May 31, 2006

(86) PCT No.: PCT/IB2006/002360

§ 371 (c)(1),
(2), (4) Date: Oct. 1, 2009

(87) PCT Pub. No.: WO2006/129204

PCT Pub. Date: Dec. 7, 2006

(65) Prior Publication Data

US 2010/0011654 A1 Jan. 21, 2010

Related U.S. Application Data

(60) Provisional application No. 60/685,765, filed on May 31, 2005.

(30) Foreign Application Priority Data

May 31, 2005 (EP) .................................... 05253339

(51) Int. Cl.
*C12N 15/11* (2006.01)
*C07H 21/04* (2006.01)

(52) U.S. Cl.
USPC ........................................ 514/44 A; 536/24.5

(58) Field of Classification Search
USPC ........................................ 514/44 A; 536/24.5
See application file for complete search history.

(56) References Cited

U.S. PATENT DOCUMENTS

| | | | | |
|---|---|---|---|---|
| 5,759,809 A | | 6/1998 | Iatrou | |
| 5,795,715 A | * | 8/1998 | Livache et al. | 435/6.18 |
| 6,326,193 B1 | | 12/2001 | Liu et al. | |
| 6,506,559 B1 | * | 1/2003 | Fire et al. | 435/6.16 |
| 6,573,099 B2 | * | 6/2003 | Graham | 435/455 |
| 6,790,629 B2 | * | 9/2004 | Julius et al. | 435/7.21 |
| 6,846,482 B2 | | 1/2005 | Liu et al. | |
| 2007/0027309 A1 | * | 2/2007 | Weinstock et al. | 536/23.7 |

FOREIGN PATENT DOCUMENTS

| | | | |
|---|---|---|---|
| CN | 1322743 | A | 11/2001 |
| WO | WO 99/32619 | A1 | 7/1999 |
| WO | WO 99/53050 | A1 | 10/1999 |
| WO | WO 00/01846 | A2 | 1/2000 |
| WO | WO 01/34815 | A1 | 5/2001 |
| WO | WO 01/37654 | A2 | 5/2001 |
| WO | WO 01/71042 | A2 | 9/2001 |
| WO | WO 01/85909 | A2 | 11/2001 |
| WO | WO 01/94371 | A1 | 12/2001 |
| WO | WO 01/94627 | A2 | 12/2001 |
| WO | WO 01/96584 | A2 | 12/2001 |
| WO | WO 02/46432 | A2 | 6/2002 |
| WO | WO 03/004644 | A1 | 1/2003 |
| WO | WO 03/052110 | A2 | 6/2003 |
| WO | WO 2004/001013 | A2 | 12/2003 |
| WO | WO 2004/022771 | A2 | 3/2004 |
| WO | WO 2004/049807 | A1 | 6/2004 |
| WO | WO 2005/047300 | A2 | 5/2005 |

OTHER PUBLICATIONS

USDA-FP 133348 5th Instar Glassy winged sharpshooter Homalodisca coagulate cDNA clone WHHC5-010_A12 5' mRNA sequence retrieved from EBI accession No. EM_EST:DN196635 on Dec. 20, 2011, Feb. 26, 2005, pp. 1-2.*

Lysiphlebus testaceipes ribosomal protein S2 (RpS4) mRNA complete cds, retrieved from EBI accession No. EM-INV:AY961528 on Dec. 20, 2011, Apr. 6, 2005, pp. 1-2.*

Domazet-Loso et al. Genome Res. 13, 2213-2219, 2003.*

Blast search result comparing SEQ ID No. 1 and AY961528, retrieved from http://blast.ncbi.nlm.nih.gov/Blast.cgi, dated Dec. 20, 2011, pp. 1-3.*

Blast search result comparing SEQ ID No. 1 and DN196635, retrieved from http://blast.ncbi.nlm.nih.gov/Blast.cgi, dated Dec. 20, 2011, pp. 1-3.*

Blast search result comparing SEQ ID No. 71 and AY231807, retrieved from http://blast.ncbi.nlm.nih.gob/Blast.cgi, dated Jul. 3, 2012 pp. 1-2.*

EBI Accession No. EM_PRO:AI187495, "EST284 *Manduca sexta* male antennae Uni-ZAP XR library *Manduca sexta* cDNA clone pMsmaD64 3' similar to 40S ribosomal protein S4, mRNA sequence," Database EMBL, Oct. 14, 1998.

EBI Accession No. EM_PRO:BI637800, "SD19884.5prime SD *Drosophila melanogaster* Schneider L2 cell culture pOT2 *Drosophila melanogaster* cDNA clone SD19884 5 similar to RpS4: FBan0011276 GO:[protein biosynthesis (GO:0006412); cytosolic small ribosomal (40S)-subunit (GO:0005843); ribosomal protein (GO:0003735); . . . ," Database EMBL, Sep. 11, 2001.

(Continued)

*Primary Examiner* — Brian Whiteman
(74) *Attorney, Agent, or Firm* — Wolf, Greenfield & Sacks, P.C.

(57) ABSTRACT

The present invention describes a new non-compound based approach for insect and/or arachnid control. The present inventors have identified for the first time novel targets for RNAi, which can effectively control insect and/or arachnid pest populations. Accordingly, the invention provides both nucleotide and amino acid sequences for the novel targets. Also provided are RNA constructs including double stranded RNA regions for mediating RNAi in insects, DNA constructs, expression vectors, host cells and compositions for controlling insects and/or arachnids using RNAi. Finally, the invention also provides for the use of the constructs, vectors, host cells and compositions in control of insects and/or arachnids populations and suitable kits for use in an RNAi based method of controlling insect and/or arachnid pests.

83 Claims, 13 Drawing Sheets

(56) References Cited

OTHER PUBLICATIONS

Figure 1:
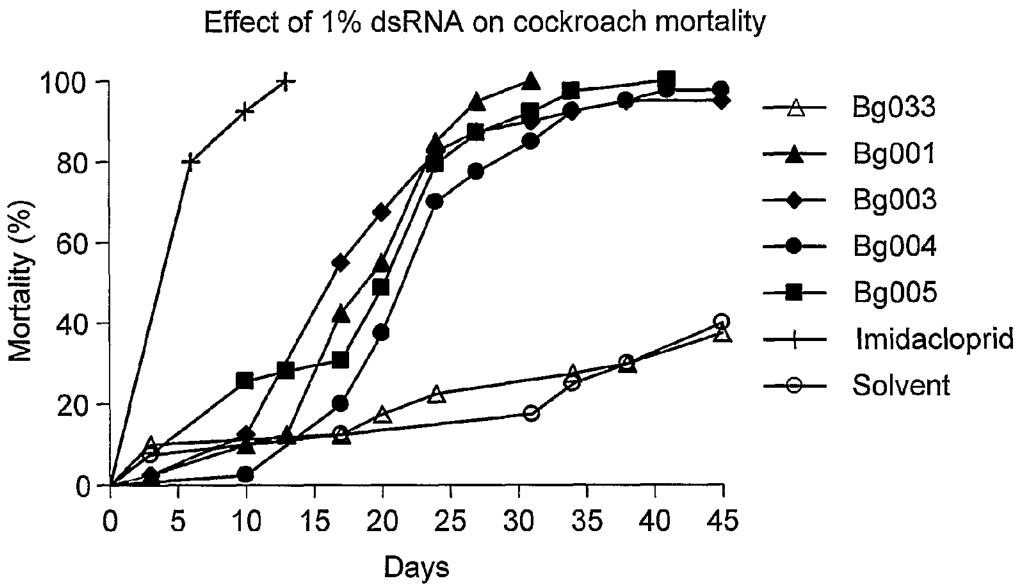

EBI Accession No. EPOP:CQ595843, "Sequence 23601 from Patent WO0171042," Database EPO Proteins, Feb. 2, 2004.

Elbashir et al., Duplexes of 21-nucleotide RNAs mediate RNA interference in cultured mammalian cells. Nature. May 24, 2001;411(6836):494-8.

Fire et al., Potent and specific genetic interference by double-stranded RNA in *Caenorhabditis elegans*. Nature. Feb. 19, 1998;391(6669):806-11.

GENBANK Submission; NCBI, Accession No. AF260897; Jeong et al.; Mar. 16, 2005.

GENBANK Submission; NCBI, Accession No. AF526210; Song et al.; Sep. 9, 2002.

GENBANK Submission; NCBI, Accession No. DN646445; Feder et al.; Mar. 28, 2005.

GENBANK Submission; NCBI, Accession No. X73679; Martinez-Gonzalez et al.; Apr. 18, 2005.

Yokokura et al., Sequence and expression of a gene encoding a ribosomal protein S4 homolog from *Drosophila melanogaster*. Gene. Oct. 15, 1993;132(2):251-4.

Gong et al., Double-stranded RNA-mediated gene silencing in cultured mosquito C6/36 cells of *Aedes albopictus*. Chin J Parasit Dis Con. 2004. 17(5):261-263. Figures.

Kramer et al., RNA interference as a metabolic engineering tool: potential for in vivo control of protein expression in an insect larval model. Metab Eng. Jul. 2003;5(3):183-90.

* cited by examiner

SEQ ID NO 1; DNA; Blattella germanica taaggcatggatgttggacaagctcggtggagtgtatgctccaagaccaagcacaggacctcacaagttacgagagagtctgc
cccttgtaatatttcttcgtaataggctgaaatatgcattaaccaactgtgaggttaagaaaattgttatgcagcgccttattaaggttg
atggaaaagtcagaacagaccccaactatccagctggttttatggatgttgttacaattgaaaaaactggagaatttttccgtctgat
ttatgacgtgaaaggacgtttcaccattcacagaataactgctgaagaagccaagtataaactgtgcaaggtaaagagagtgca
gactgggcccaagggtattccattcttggtgacccatgatggtagaactcttagatatcctgatcctgtcatcaaagttaatgataca
gttcaacttgacatcgctacttccaagattatggatagcatcaaatttgataatggtaatctctgtatgattactggaggccgtaacttg
ggtcgtgttggaactgtagttaatcgagaacgtcatcctggttcctttgacattgtgcatgttaaagattcacaaggacacacatttgc
taccagattgaa SEQ ID NO 2; PRT; Blattella germanica Lys Ala Trp Met Leu Asp Lys Leu Gly Gly Val Tyr Ala Pro Arg Pro Ser Thr Gly Pro His Lys
Leu Arg Glu Ser Leu Pro Leu Val Ile Phe Leu Arg Asn Arg Leu Lys Tyr Ala Leu Thr Asn Cys
Glu Val Lys Lys Ile Val Met Gln Arg Leu Ile Lys Val Asp Gly Lys Val Arg Thr Asp Pro Asn Tyr
Pro Ala Gly Phe Met Asp Val Val Thr Ile Glu Lys Thr Gly Glu Phe Phe Arg Leu Ile Tyr Asp
Val Lys Gly Arg Phe Thr Ile His Arg Ile Thr Ala Glu Glu Ala Lys Tyr Lys Leu Cys Lys Val Lys
Arg Val Gln Thr Gly Pro Lys Gly Ile Pro Phe Leu Val Thr His Asp Gly Arg Thr Leu Arg Tyr
Pro Asp Pro Val Ile Lys Val Asn Asp Thr Val Gln Leu Asp Ile Ala Thr Ser Lys Ile Met Asp Ser
Ile Lys Phe Asp Asn Gly Asn Leu Cys Met Ile Thr Gly Gly Arg Asn Leu Gly Arg Val Gly Thr
Val Val Asn Arg Glu Arg His Pro Gly Ser Phe Asp Ile Val His Val Lys Asp Ser Gln Gly His
Thr Phe Ala Thr Arg Leu Asn SEQ ID NO 3; DNA; Blattella germanica; degenerate primer; w is a or t; r is a or g; m is a or c; y is c or t catttgaagc gtttwrmygc ycc SEQ ID NO 4; DNA; Blattella germanica; specific primer gtgcccttgc caatgatgaa cacgttg SEQ ID NO 5; DNA; specific T7 primer cgctaatacg actcactata ggggagtgta tgctccaaga ccaag SEQ ID NO 6; DNA; Blattella germanica; specific primer caatctggta gcaaatgtgt gtcc SEQ ID NO 7; DNA; Blattella germanica; specific primer ggagtgtatg ctccaagacc aag SEQ ID NO 8; DNA; synthetic T7 primer cgctaatacg actcactata ggcaatctgg tagcaaatgt gtgtcc SEQ ID NO 9; RNA; Blattella germanica; u can be t (for DNA complement)

ggaguguaug cuccaagacc aagcacagga ccucacaagu uacgagagag ucugccccuu

FIG. 5 guaauauuuc uucguaauag gcugaaauau gcauuaacca acugugaggu uaagaaaauu
guuaugcagc gccuuauuaa gguugaugga aaagucagaa cagaccccaa cuauccagcu
gguuuuaugg auguuguuac aauugaaaaa acuggagaau uuuuccgucu gauuuaugac
gugaaaggac guuucaccau ucacagaaua acugcugaag aagccaagua uaaacugugc
aagguaaaga gagugcagac ugggcccaag gguauuccau ucuuggugac ccaugauggu
agaacucuua gauauccuga uccugucauc aaaguuaaug auacaguuca acuugacauc
gcuacuucca agauuaugga uagcaucaaa uuugauaaug guaaucucug uaugauuacu
ggaggccgua acuugggucg uguuggaacu guaguuaauc gagaacguca uccugguucc
uuugacauug ugcauguuaa agauucacaa ggacacacau uugcuaccag auug SEQ ID NO 10; RNA; Blattella germanica; u can be t (for DNA complement)

ggaguguaug cuccaagacc aagcacagga ccucacaagu uacgagagag ucugccccuu
guaauauuuc uucguaauag gcugaaauau gcauuaacca acugugaggu uaagaaaauu
guuaugcagc gccuuauuaa gguugaugga aaagucagaa cagaccccaa cuauccagcu
gguuuuaugg auguuguuac aauugaaaaa acuggagaau uuuuccgucu gauuuaugac
gugaaaggac guuucaccau ucacagaaua acugcugaag aagccaagua uaaacugugc
aagguaaaga gagugcagac ugggcccaag gguauuccau ucuuggugac ccaugauggu
agaacucuua gauauccuga uccugucauc aaaguuaaug auacaguuca acuugacauc
gcuacuucca agauuaugga uagcaucaaa uuugauaaug guaaucucug uaugauuacu
ggaggccgua acuugggucg uguuggaacu guaguuaauc gagaacguca uccugguucc
uuugacauug ugcauguuaa agauucacaa gga SEQ ID NO 11; DNA; Blattella germanica;

tcccaggcgaccttatgaaaaggcacgtcttgatcaggagttgaaaatcataggagaatatggtcttaggaacaaacgtgaagt
gtggcgagtcaagtataccttggcaaaaatccgtaaagctgccagagaacttctgactttggaagagaaagatcagcgcaggtt
gtttgaaggcaatgctcttcttcgtcggttggtgcgtattggagtgttggatgaaacccgtatgaagcttgattacgtcttgggtttgaag
attgaagatttcttggaacgacgtctccaaacacaagttttcaagttggggcttgcaaaatcaatccatcatgctcgtgtgctgatcc
gtcaaagacatatcagggttcgtaagcaggtcgtgaatattccaagcttcattgtgagacttgattcccagaagcatattgacttctc
g SEQ ID NO 12; PRT; Blattella germanica;

Pro Arg Arg Pro Tyr Glu Lys Ala Arg Leu Asp Gln Glu Leu Lys Ile Ile Gly Glu Tyr Gly Leu Arg
Asn Lys Arg Glu Val Trp Arg Val Lys Tyr Thr Leu Ala Lys Ile Arg Lys Ala Ala Arg Glu Leu
Leu Thr Leu Glu Glu Lys Asp Gln Arg Arg Leu Phe Glu Gly Asn Ala Leu Leu Arg Arg Leu Val
Arg Ile Gly Val Leu Asp Glu Thr Arg Met Lys Leu Asp Tyr Val Leu Gly Leu Lys Ile Glu Asp
Phe Leu Glu Arg Arg Leu Gln Thr Gln Val Phe Lys Leu Gly Leu Ala Lys Ser Ile His His Ala
Arg Val Leu Ile Arg Gln Arg His Ile Arg Val Arg Lys Gln Val Val Asn Ile Pro Ser Phe Ile Val
Arg Leu Asp Ser Gln Lys His Ile Asp Phe
Ser

SEQ ID NO 13; DNA; Blattella germanica; degenerate primer; n is a, c, g, or t; y is c or t; k is g or t tcggtcttct cgaagacnta ygtkac SEQ ID NO 14; DNA; Blattella germanica; degenerate primer; m is a or c; y is c or t; b is c, g or t ccgccgaagg gmgayttbag

FIG. 5 CONT'D

SEQ ID NO 15; DNA; specific T7 primer cgctaatacg actcactata ggcaggcgac cttatgaaaa ggc SEQ ID NO 16; DNA; Blattella germanica; specific primer cgagaagtca atatgcttct ggg SEQ ID NO 17; DNA; Blattella germanica; specific primer caggcgacct tatgaaaagg c SEQ ID NO 18; DNA; specific T7 primer cgctaatacg actcactata ggcgagaagt caatatgctt ctggg SEQ ID NO 19; RNA; Blattella germanica; u can be t (for DNA complement)

caggcgaccu uaugaaaagg cacgucuuga ucaggaguug aaaaucauag gagaauaugg
ucuuaggaac aaacgugaag uguggcgagu caaguauacc uuggcaaaaa uccguaaagc
ugccagagaa cuucugacuu uggaagagaa agaucagcgc agguuguuug aaggcaaugc
ucuucuucgu cgguuggugc guauuggagu guuggaugaa acccguauga agcuugauua
cgucuugggu uugaagauug aagauuucuu ggaacgacgu cuccaaacac aaguuuucaa
guuggggcuu gcaaaaucaa uccaucaugc ucgugugcug auccgucaaa gacauaucag
gguucguaag caggucguga auauuccaag cuucauugug agacuugauu cccagaagca
uauugacuuc ucg SEQ ID NO 20; RNA; Blattella germanica; u can be t (for DNA complement)

caggcgaccu uaugaaaagg cacgucuuga ucaggaguug aaaaucauag gagaauaugg
ucuuaggaac aaacgugaag uguggcgagu caaguauacc uuggcaaaaa uccguaaagc
ugccagagaa cuucugacuu uggaagagaa agaucagcgc agguuguuug aaggcaaugc
ucuucuucgu cgguuggugc guauuggagu guuggaugaa acccguauga agcuugauua
cgucuugggu uugaagauug aagauuucuu ggaacgacgu cuccaaacac aaguuuucaa
guuggggcuu gcaaaaucaa uccaucaugc ucgugugcug auccgucaaa gacauaucag
gguucguaag caggucguga auauuccaag cuucauugug agacuugauu cc SEQ ID NO 21; DNA; Blattella germanica;

tgtgaaaggaccacgaggcaccttgaagcgcggtttcaagcatcttgctttagatatccacttggttcatccaaggctcctgaaggt
ggaaaaatggtttggaacaaagaaggagttggcagccgtgcgcaccgtctgctctcatattgagaacatgattaaaggagtcac
aaagggtttcctgtacaaaatgcgcgccgtgtatgcccatttccccattaactgcgtaaccacagaaaacaattccgttattgaagt
gcgtaacttcttgggcgagaagttcatccgcagagtgaagatggctccgggagtgaccgtcaccaattctccaaagcagaaag
acgagctcattctggagggcaacgacatcgaggatgtatcgagatcagccgcactcatccaacaatcgacgactgtgaagaa
caaggacatccggaaattccttgac SEQ ID NO 22; PRT; Blattella germanica;

Val Lys Gly Pro Arg Gly Thr Leu Lys Arg Gly Phe Lys His Leu Ala Leu Asp Ile His Leu Val
His Pro Arg Leu Leu Lys Val Glu Lys Trp Phe Gly Thr Lys Lys Glu Leu Ala Ala Val Arg Thr
Val Cys Ser His Ile Glu Asn Met Ile Lys Gly Val Thr Lys Gly Phe Leu Tyr Lys Met Arg Ala Val
Tyr Ala His Phe Pro Ile Asn Cys Val Thr Thr Glu Asn Asn Ser Val Ile Glu Val Arg Asn Phe
Leu Gly Glu Lys Phe Ile Arg Arg Val Lys Met Ala Pro Gly Val Thr Val Thr Asn Ser Pro Lys
Gln Lys Asp Glu Leu Ile Leu Glu Gly Asn Asp Ile Glu Asp Val Ser Arg Ser Ala Ala Leu Ile Gln
Gln Ser Thr Thr Val Lys Asn Lys Asp Ile

FIG. 5 CONT'D

Arg Lys Phe Leu Asp

SEQ ID NO 23; DNA; Blattella germanica; forward degenerative primer; n is a, c, g, or t gtgaaggccc gnntggtgac 20

SEQ ID NO 24; DNA; Blattella germanica; reverse degenerative primer;-d is a, g or t; h is a, c or t; r is a or g; v is a,c or g gtcgtcttct cdgahacrta vagacc SEQ ID NO 25; DNA; T7 primer forward cgctaatacg actcactata gggtgaaagg accacgaggc acc SEQ ID NO 26; DNA; Blattella germanica; specific primer reverse ccgtcaagga atttccggat g SEQ ID NO 27; DNA; Blattella germanica; specific primer forward gtgaaaggac cacgaggcac c SEQ ID NO 28; DNA; specific T7 primer reverse cgctaatacg actcactata ggccgtcaag gaatttccgg atg SEQ ID NO 29; RNA; Blattella germanica; u can be t (for DNA complement)

gugaaaggac cacgaggcac cuugaagcgc gguuucaagc aucuugcuuu agauauccac
uugguucauc caaggcuccu gaagguggaa aaaugguuug gaacaaagaa ggaguuggca
gccgugcgca ccgucugcuc ucauauugag aacaugauua aaggagucac aaaggguuuc
cuguacaaaa ugcgcgccgu guaugcccau uucccCauua acugcguaac cacagaaaac
aauuccguua uugaagugcg uaacuucuug ggcgagaagu ucauccgcag agugaagaug
gcuccgggag ugaccgucac caauucucca aagcagaaag acgagcucau ucuggagggc
aacgacaucg aggauguauc gagaucagcc gcacucaucc aacaaucgac gacugugaag
aacaaggaca uccggaaauu ccuugacgg SEQ ID NO 30; RNA; Blattella germanica; u can be t (for DNA complement)

gugaaaggac cacgaggcac cuugaagcgc gguuucaagc aucuugcuuu agauauccac
uugguucauc caaggcuccu gaagguggaa aaaugguuug gaacaaagaa ggaguuggca
gccgugcgca ccgucugcuc ucauauugag aacaugauua aaggagucac aaaggguuuc
cuguacaaaa ugcgcgccgu guaugcccau uuccccauua acugcguaac cacagaaaac
aauuccguua uugaagugcg uaacuucuug ggcgagaagu ucauccgcag agugaagaug
gcuccgggag ugaccgucac caauucucca aagcagaaag acgagcucau ucuggagggc
aacgacaucg aggauguauc gagaucagcc gcacucaucc aacaaucgac gacugugaag
aacaagga

FIG. 5 CONT'D

SEQ ID NO 31; DNA; Blattella germanica;

ggcttgatcccaatgaaataaacgaaattgcaaataccaattccagacaaaatattcgtaaactgattaaagatggtcttatcatc
aagaagcccgtagctgtacactcaagggcccgtgttcgcaagaacaccgaagcaagaagaaaaggacgtcactgcggttttg
gcaaaaggaagggtacggcaaatgcccgtatgccacagaaggtcttgtggattaatcgcatgcgtgttctgagaaggcttctca
agaagtacagggaagcaaagaagatcgacagacatctataccaccagctgtacatgaaggccaagggtaacgtgttcaaga
acaagcgtgtcctgatggagttcatccacaagaagaaggctgagaaggccaggacaaagatgcttaacgac SEQ ID NO 32; PRT; Blattella germanica;

Leu Asp Pro Asn Glu Ile Asn Glu Ile Ala Asn Thr Asn Ser Arg Gln Asn Ile Arg Lys Leu Ile Lys
Asp Gly Leu Ile Ile Lys Lys Pro Val Ala Val His Ser Arg Ala Arg Val Arg Lys Asn Thr Glu Ala
Arg Arg Lys Gly Arg His Cys Gly Phe Gly Lys Arg Lys Gly Thr Ala Asn Ala Arg Met Pro Gln
Lys Val Leu Trp Ile Asn Arg Met Arg Val Leu Arg Arg Leu Leu Lys Lys Tyr Arg Glu Ala Lys
Lys Ile Asp Arg His Leu Tyr His Gln Leu Tyr Met Lys Ala Lys Gly Asn Val Phe Lys Asn Lys
Arg Val Leu Met Glu Phe Ile His Lys Lys Lys Ala Glu Lys Ala Arg Thr Lys Met Leu Asn Asp

SEQ ID NO 33; DNA; Blattella germanica; degenerative primer forward; r is a or g; b is c or g or t tgcgatgcgg caaraaraag gtbtgg SEQ ID NO 34; DNA; Blattella germanica; degenerative primer reverse; y is c or t; r is a or g gtcggcgagc ytcrgcytg SEQ ID NO 35; DNA; specific T7 primer forward cgctaatacg actcactata ggggcttgat cccaatgaaa taaacg SEQ ID NO 36; DNA; Blattella germanica; specific primer reverse gtcgttaagc atctttgtcc tggc SEQ ID NO 37; DNA; Blattella germanica; specific primer forward ggcttgatcc caatgaaata aacg SEQ ID NO 38; DNA; specific T7 primer reverse cgctaatacg actcactata gggtcgttaa gcatctttgt cctggc SEQ ID NO 39; RNA; Blattella germanica; u can be t (for DNA complement)

ggcuugaucc caaugaaaua aacgaaauug caaauaccaa uuccagacaa aauauucgua
aacugauuaa agauggucuu aucaucaaga agcccguagc uguacacuca agggcccgug

FIG. 5 CONT'D uucgcaagaa caccgaagca agaagaaaag gacgucacug cgguuuuggc aaaaggaagg
guacggcaaa ugcccguaug ccacagaagg ucuuguggau uaaucgcaug cguguucuga
gaaggcuucu caagaaguac agggaagcaa agaagaucga cagacaucua uaccaccagc
uguacaugaa ggccaagggu aacguguuca agaacaagcg uguccugaug gaguucaucc
acaagaagaa ggcugagaag gccaggacaa agaugcuuaa cgac SEQ ID NO 40; RNA; Blattella germanica; u can be t (for DNA complement)

ggcuugaucc caaugaaaua aacgaaauug caaauaccaa uuccagacaa aauauucgua
aacugauuaa agauggucuu aucaucaaga agcccguagc uguacacuca agggcccgug
uucgcaagaa caccgaagca agaagaaaag gacgucacug cgguuuuggc aaaaggaagg
guacggcaaa ugcccguaug ccacagaagg ucuuguggau uaaucgcaug cguguucuga
gaaggcuucu caagaaguac agggaagcaa agaagaucga cagacaucua uaccaccagc
uguacaugaa ggccaagggu aacguguuca agaacaagcg uguccugaug gaguucaucc
acaagaagaa ggcugagaag gcc SEQ ID NO 41; DNA; Blattella germanica;

atggatgccatcaagaagaagatgcaggcgatgaagctggagaaggacaacgcgatggatcgcgcccttctctgcgaacag
caggcccgcgacgccaacatccgggccgagaaggctgaggaggaggcccgatccctgcagaagaagatccagcagattg
agaatgatcttgatcagaccatggagcagttgatgcaagtcaacgccaagctggacgagaaggacaaggccctgcagaatgc
tgagagtgaggtcgctgccctcaaccgccgaatccaactgctggagga
ggatcttgagaggtctgaggaacgtttggccacagccaccgccaagttggctgaggcttcccaggctgccgatgagtcagagc
gagctcgtaagattcttgaatccaaaggcctggcagatgaagagcgtatggatgctttggagaaccagctgaaggaagccagg
ttcatggctgaggaagctgacaagaaatatgatgaggtcgcacgtaagttggctatggttgaggccgacttggaaagagcaga
agagcgtgccgagactggtgaatccaagattgtggagcttgaggaagaactgcgcgttgtcggcaacaacctgaagtccctga
ggtgtctgaagagagaaggccaacctgcgtgaggaagagtacaagcaacagattaagactctgaataccaggctaaaggaggc
tgaagctcgtgctgagttcgctgaaagatccgtgcagaaattgcagaaggaggttgacaggcttgaggatgaattggtacacga
gaaggagaagtacaagtacatttgtgacgatcttgatatgactttcaccgaacttattggc SEQ ID NO 42; PRT; Blattella germanica;

Met Asp Ala Ile Lys Lys Lys Met Gln Ala Met Lys Leu Glu Lys Asp Asn Ala Met Asp Arg Ala
Leu Leu Cys Glu Gln Gln Ala Arg Asp Ala Asn Ile Arg Ala Glu Lys Ala Glu Glu Glu Ala Arg
Ser Leu Gln Lys Lys Ile Gln Gln Ile Glu Asn Asp Leu Asp Gln Thr Met Glu Gln Leu Met Gln
Val Asn Ala Lys Leu Asp Glu Lys Asp Lys Ala Leu Gln Asn Ala Glu Ser Glu Val Ala Ala Leu
Asn Arg Arg Ile Gln Leu Leu Glu Glu Asp Leu Glu Arg Ser Glu Glu Arg Leu Ala Thr Ala Thr
Ala Lys Leu Ala Glu Ala Ser Gln Ala Ala Asp Glu Ser Glu Arg Ala Arg Lys Ile Leu Glu Ser
Lys Gly Leu Ala Asp Glu Glu Arg Met Asp Ala Leu Glu Asn Gln Leu Lys Glu Ala Arg Phe Met
Ala Glu Glu Ala Asp Lys Lys Tyr Asp Glu Val Ala Arg Lys Leu Ala Met Val Glu Ala Asp Leu
Glu Arg Ala Glu Glu Arg Ala Glu Thr Gly Glu Ser Lys Ile Val Glu Leu Glu Glu Glu Leu Arg
Val Val Gly Asn Asn Leu Lys Ser Leu Glu Val Ser Glu Glu Lys Ala Asn Leu Arg Glu Glu Glu
Tyr Lys Gln Gln Ile Lys Thr Leu Asn Thr Arg Leu Lys Glu Ala Glu Ala Arg Ala Glu Phe Ala
Glu Arg Ser Val Gln Lys Leu Gln Lys Glu Val Asp Arg Leu Glu Asp Glu Leu Val His Glu Lys
Glu Lys Tyr Lys Tyr Ile Cys Asp Asp Leu Asp Met Thr Phe Thr Glu Leu Ile Gly

SEQ ID NO 43; DNA; Blattella germanica; specific primer forward atggatgcca tcaagaagaa gatgcag

FIG. 5 CONT'D

SEQ ID NO 44; DNA; Blattella germanica; specific primer reverse gccaataagt tcggtgaaag tcatatcaag SEQ ID NO 45; DNA; specific T7 primer forward cgctaatacg actcactata ggatggatgc catcaagaag aagatg SEQ ID NO 46; DNA; specific T7 primer reverse cgctaatacg actcactata gggccaataa gttcggtgaa agtcat SEQ ID NO 47; RNA; Blattella germanica; u can be t (for DNA complement)

auggaugcca ucaagaagaa gaugcaggcg augaagcugg agaaggacaa cgcgauggau
cgcgcccuuc ucugcgaaca gcaggcccgc gacgccaaca uccgggccga gaaggcugag
gaggaggccc gaucccugca gaagaagauc cagcagauug agaaugaucu ugaucagacc
auggagcagu ugaugcaagu caacgccaag cuggacgaga aggacaaggc ccugcagaau
gcugagagug aggucgcugc ccucaaccgc cgaauccaac ugcuggagga ggaucuugag
aggucugagg aacguuuggc cacagccacc gccaaguugg cugaggcuuc ccaggcugcc
gaugagucag agcgagcucg uaagauucuu gaauccaaag gccuggcaga ugaagagcgu
auggaugcuu uggagaacca gcugaaggaa gccagguuca uggcugagga agcugacaag
aaauaugaug aggucgcacg uaaguuggcu augguugagg ccgacuugga aagagcagaa
gagcgugccg agacugguga auccaagauu guggagcuug aggaagaacu gcgcguuguc
ggcaacaacc ugaagucccu ugaggugucu gaagagaagg ccaaccugcg ugaggaagag
uacaagcaac agauuaagac ucugaauacc aggcuaaagg aggcugaagc ucgugcugag
uucgcugaaa gauccgugca gaaauugcag aaggagguug acaggcuuga ggaugaauug
guacacgaga aggagaagua caaguacauu ugugacgauc uugauaugac uuucaccgaa
cuuauuggc SEQ ID NO 48; RNA; Blattella germanica; u can be t (for DNA complement)

ccaucaagaa gaagaugcag gcgaugaagc uggagaagga caacgcgaug gaucgcgccc
uucucugcga acagcaggcc cgcgacgcca acauccgggc cgagaaggcu gaggaggagg
cccgaucccu gcagaagaag auccagcaga uugagaauga ucuugaucag accauggagc
aguugaugca agucaacgcc aagcuggacg agaaggacaa ggcccugcag aaugcugaga
gugaggucgc ugcccucaac cgccgaaucc aacugcugga ggaggaucuu gagaggucug
aggaacguuu ggccacagcc accgccaagu uggcugaggc uucccaggcu gccgaugagu
cagagcgagc ucguaagauu cuugaaucca aaggccuggc agaugaagag cguauggaug
cuuuggagaa ccagcugaag gaagccaggu ucauggcuga ggaagcugac aagaaauaug
augaggucgc acguaaguug gcuaugguug aggccgacuu ggaaagagca gaagagcgug
ccgagacugg ugaauccaag auuguggagc uugaggaaga acugcgcguu gucggcaaca
accugaaguc ccuugaggug ucugaagaga aggccaaccu gcgugaggaa gaguacaagc
aacagauuaa gacucugaau accaggcuaa aggaggcuga agcucgugcu gaguucgcug
aaagauccgu gcagaaauug cagaaggagg uugacaggcu ugaggaugaa uugguacacg
agaaggagaa guacaaguac auuugugacg aucuugauau g SEQ ID NO 49; DNA; Blattella germanica;

gctctggagctcatattcccttcgcagtatgtggatcaggtggacctcgaggtctacgacaatgtttctgcaggaaagtacacggtg
gggttgggacaggctcgcatggggttctgcacggacagggaggacatcaactctctgtgtctcaccgtcgtcagtcgactgatgg
aacgatggagcatcccctactcgcaaattgggcgcctggaagtaggcaccgagacccttctgg

FIG. 5 CONT'D acaagtcgaagagcgtcaagactgtcctgatgcaactcttcaaggacaacacggacatcgagggcgtggataccgtgaacgc
ctgttacgggggcacctcggctctcttcaatgcgatttcgtgggtggagtccagctcctgggatggcaggtatgctcttgtggtcgctg
gggacattgctgtgtatgctaaaggcagtgcgaggcccaccggtggagcaggggctgtggccatgctagtgggcgccaatgct
cccctagtgttcgacagaggagttcgttcatcacacatgcaacatgcttatgacttctacaaaccggatctgtcctcgctgtacccca
ccgtggatggcaagctgtcaattcaatgctatcttagtgccttagatcattgttatcaactgtactgctccaagatccagaaacaactt
ggagagaagttcgatattgagcggctggatgcagttctcttccacgcgccttattgtaagttggtgcagaagtctcttgctcgcctcgt
cttgaacgactttgtgcgggcatcagaggaggagcggacgactaaatactccagtctggaagcactaaaggcgtgaagcta
gaagatacgtacttcgaccgagaagttgagaaagcagtcatgacatacagcaagaacatgtttgaagagaaaacaaagccct
cgctgttgctcgccaaccaagtcggcaacatgtacactccttcgctttacggaggtttggtctctctattggtcagcaagagcgccca
ggagttggcagggaagcgcgtggccttgttttcttacggctccggactggcctcttccatgttctctctaagaatatcatcggacgcc
agcgcgaaatcttctctgcaacgcctcgtctcgaatctctcgcacatcaagccgcagctggatctgcgccacaaggtgtcaccag
aggagtttgcacaaacgatggagacgagggaacacaaccaccacaaagctccatacaccccagagggctcgatcgacgtct
tgtttccaggaacttggtatctggagagcgtggacagcc SEQ ID NO 50; PRT; Blattella germanica;

Ala Leu Glu Leu Ile Phe Pro Ser Gln Tyr Val Asp Gln Val Asp Leu Glu Val Tyr Asp Asn Val
Ser Ala Gly Lys Tyr Thr Val Gly Leu Gly Gln Ala Arg Met Gly Phe Cys Thr Asp Arg Glu Asp
Ile Asn Ser Leu Cys Leu Thr Val Val Ser Arg Leu Met Glu Arg Trp Ser Ile Pro Tyr Ser Gln Ile
Gly Arg Leu Glu Val Gly Thr Glu Thr Leu Leu Asp Lys Ser Lys Ser Val Lys Thr Val Leu Met
Gln Leu Phe Lys Asp Asn Thr Asp Ile Glu Gly Val Asp Thr Val Asn Ala Cys Tyr Gly Gly Thr
Ser Ala Leu Phe Asn Ala Ile Ser Trp Val Glu Ser Ser Ser Trp Asp Gly Arg Tyr Ala Leu Val
Val Ala Gly Asp Ile Ala Val Tyr Ala Lys Gly Ser Ala Arg Pro Thr Gly Gly Ala Gly Ala Val Ala
Met Leu Val Gly Ala Asn Ala Pro Leu Val Phe Asp Arg Gly Val Arg Ser Ser His Met Gln His
Ala Tyr Asp Phe Tyr Lys Pro Asp Leu Ser Ser Leu Tyr Pro Thr Val Asp Gly Lys Leu Ser Ile
Gln Cys Tyr Leu Ser Ala Leu Asp His Cys Tyr Gln Leu Tyr Cys Ser Lys Ile Gln Lys Gln Leu
Gly Glu Lys Phe Asp Ile Glu Arg Leu Asp Ala Val Leu Phe His Ala Pro Tyr Cys Lys Leu Val
Gln Lys Ser Leu Ala Arg Leu Val Leu Asn Asp Phe Val Arg Ala Ser Glu Glu Glu Arg Thr Thr
Lys Tyr Ser Ser Leu Glu Ala Leu Lys Gly Val Lys Leu Glu Asp Thr Tyr Phe Asp Arg Glu Val
Glu Lys Ala Val Met Thr Tyr Ser Lys Asn Met Phe Glu Glu Lys Thr Lys Pro Ser Leu Leu Leu
Ala Asn Gln Val Gly Asn Met Tyr Thr Pro Ser Leu Tyr Gly Gly Leu Val Ser Leu Leu Val Ser
Lys Ser Ala Gln Glu Leu Ala Gly Lys Arg Val Ala Leu Phe Ser Tyr Gly Ser Gly Leu Ala Ser
Ser Met Phe Ser Leu Arg Ile Ser Ser Asp Ala Ser Ala Glu Ser Pro Leu Gln Arg Leu Val Ser
Asn Leu Ser His Ile Lys Pro Gln Leu Asp Leu Arg His Lys Val Ser Pro Glu Glu Phe Ala Gln
Thr Met Glu Thr Arg Glu His Asn His His Lys Ala Pro Tyr Thr Pro Glu Gly Ser Ile Asp Val
Leu Phe Pro Gly Thr Trp Tyr Leu Glu Ser Val Asp Ser

SEQ ID NO 51; DNA; Blattella germanica; specific primer forward gctctggagc tcatattccc ttcgc SEQ ID NO 52; DNA; Blattella germanica; specific primer reverse ggctgtccac gctctccaga tacc SEQ ID NO 53; DNA; specific T7 primer forward cgctaatacg actcactata gggctctgga gctcatattc ccttc SEQ ID NO 54; DNA; specific T7 primer reverse

FIG. 5 CONT'D cgctaatacg actcactata ggggctgtcc acgctctcca g

SEQ ID NO 55; RNA; Blattella germanica; u can be t (for DNA complement)

gcucuggagc ucauauuccc uucgcaguau guggaucagg uggaccucga ggucuacgac
aauguuucug caggaaagua cacggugggg uugggacagg cucgcauggg guucugcacg
gacagggagg acaucaacuc ucugugucuc accgucguca gucgacugau ggaacgaugg
agcaucccc u acucgcaaau ugggcgccug gaaguaggca ccgagacccu ucuggacaag
ucgaagagcg ucaagacugu ccugaugcaa cucuucaagg acaacacgga caucgagggc
guggauaccg ugaacgccug uuacgggggc accucggcuc ucuucaaugc gauuucgugg
guggagucca gcuccuggga uggcagguau gcucuugugg ucgcugggga cauugcugug
uaugcuaaag gcagugcgag gcccaccggu ggagcagggg cuguggccau gcuagugggc
gccaaugcuc cccuaguguu cgacagagga guucguucau cacacaugca acaugcuuau
gacuucuaca aaccggaucu guccucgcug uaccccaccg uggauggcaa gcugucaauu
caaugcuauc uuagugccuu agaucauugu uaucaacugu acugcuccaa gauccagaaa
caacuuggag agaaguucga uauugagcgg cuggaugcag uucucuucca cgcgccuuau
uguaaguugg ugcagaaguc ucuugcucgc cucgucuuga acgacuuugu gcgggcauca
gaggaggagc ggacgacuaa auacuccagu cuggaagcac uaaaaggcgu gaagcuagaa
gauacguacu ucgaccgaga aguugagaaa gcagucauga cauacagcaa gaacauguuu
gaagagaaaa caaagcccuc gcuguugcuc gccaaccaag ucggcaacau guacacuccu
ucgcuuuacg gagguuuggu cucucuauug gucagcaaga gcgcccagga guuggcaggg
aagcgcgugg ccuuguuuuc uuacggcucc ggacuggccu cuuccauguu cucucuaaga
auaucaucgg acgccagcgc gaaaucuucu cugcaacgcc ucgucucgaa ucucucgcac
aucaagccgc agcuggaucu gcgccacaag gugucaccag aggaguuugc acaaacgaug
gagacgaggg aacacaacca ccacaaagcu ccauacaccc cagagggcuc gaucgacguc
uuguuuccag gaacuuggua ucuggagagc guggacagcc SEQ ID NO 56; RNA; Blattella germanica; u can be t (for DNA complement)

gcucuggagc ucauauuccc uucgcaguau guggaucagg uggaccucga ggucuacgac
aauguuucug caggaaagua cacggugggg uugggacagg cucgcauggg guucugcacg
gacagggagg acaucaacuc ucugugucuc accgucguca gucgacugau ggaacgaugg
agcaucccc u acucgcaaau ugggcgccug gaaguaggca ccgagacccu ucuggacaag
ucgaagagcg ucaagacugu ccugaugcaa cucuucaagg acaacacgga caucgagggc
guggauaccg ugaacgccug uuacgggggc accucggcuc ucuucaaugc gauuucgugg
guggagucca gcuccuggga uggcagguau gcucuugugg ucgcugggga cauugcugug
uaugcuaaag gcagugcgag gcccaccggu ggagcagggg cuguggccau gcuagugggc
gccaaugcuc cccuaguguu cgacagagga guucguucau cacacaugca acaugcuuau
gacuucuaca aaccggaucu guccucgcug uaccccaccg uggauggcaa gcugucaauu
caaugcuauc uuagugccuu agaucauugu uaucaacugu acugcuccaa gauccagaaa
caacuuggag agaaguucga uauugagcgg cuggaugcag uucucuucca cgcgccuuau
uguaaguugg ugcagaaguc ucuugcucgc cucgucuuga acgacuuugu gcgggcauca
gaggaggagc ggacgacuaa auacuccagu cuggaagcac uaaaaggcgu gaagcuagaa
gauacguacu ucgaccgaga aguugagaaa gcagucauga cauacagcaa gaacauguuu
gaagagaaaa caaagcccuc gcuguugcuc gccaaccaag ucggcaacau guacacuccu
ucgcuuuacg gagguuuggu cucucuauug gucagcaaga gcgcccagga guuggcaggg
aagcgcgugg ccuuguuuuc uuacggcucc ggacuggccu cuuccauguu cucucuaaga
auaucaucgg acgccagcgc gaaaucuucu cugcaacgcc ucgucucgaa ucucucgcac
aucaagccgc agcuggaucu gcgccacaag gugucaccag aggaguuugc acaaacgaug
gagacgaggg aacacaacca ccacaaagcu ccauacaccc cagagggcuc gaucgacguc
uuguuuccag gaacuuggu SEQ ID NO 57; DNA; Blattella germanica;

FIG. 5 CONT'D gaggcccagagcaagagaggtatcctcactctgaagtaccccattgaacatggaatcatcaccaactgggatgacatggaga
agatctggcatcacaccttctacaatgaactccgagtggctccagaggaacacccaatcctgctgactgaggctcccctgaacc
caaaggccaacagggagaagatgactcaaatcatgtttgagaccttcaacacccccgccatgtatgttgccatccaggccgtgc
tgtccctctacgcttccggccgtaccactggtattgtgctggactctggtgacggcgtctcccacaccgtacccatctatgaaggtta
cgcattgccccatgccatcctgcgtctggacttggccggccgtgacttgactgactacctgatgaagatcctgaccgagcgtggct
acagcttcacaactacagcagagcgag SEQ ID NO 58; PRT; Blattella germanica;

Glu Ala Gln Ser Lys Arg Gly Ile Leu Thr Leu Lys Tyr Pro Ile Glu His Gly Ile Ile Thr Asn Trp
Asp Asp Met Glu Lys Ile Trp His His Thr Phe Tyr Asn Glu Leu Arg Val Ala Pro Glu Glu His
Pro Ile Leu Leu Thr Glu Ala Pro Leu Asn Pro Lys Ala Asn Arg Glu Lys Met Thr Gln Ile Met
Phe Glu Thr Phe Asn Thr Pro Ala Met Tyr Val Ala Ile Gln Ala Val Leu Ser Leu Tyr Ala Ser
Gly Arg Thr Thr Gly Ile Val Leu Asp Ser Gly Asp Gly Val Ser His Thr Val Pro Ile Tyr Glu Gly
Tyr Ala Leu Pro His Ala Ile Leu Arg Leu Asp Leu Ala Gly Arg Asp Leu Thr Asp Tyr Leu Met
Lys Ile Leu Thr Glu Arg Gly Tyr Ser Phe Thr Thr Thr Ala Glu Arg

SEQ ID NO 59; DNA; Blattella germanica; degenerative primer forward gaggcccaga gcaagagagg tatcc SEQ ID NO 60; DNA; Blattella germanica; degenerative primer reverse ctcgctctgc tgtagttgtg aagctg SEQ ID NO 61; DNA; specific T7 primer forward cgctaatacg actcactata gggaggccca gagcaagaga gg SEQ ID NO 62; DNA; specific T7 primer reverse cgctaatacg actcactata ggtctgctgt agttgtgaag ctgtagcc SEQ ID NO 63; RNA; Blattella germanica; u can be t (for DNA complement)

gaggcccaga gcaagagagg uauccucacu cugaaguacc ccauugaaca uggaaucauc
accaacuggg augacaugga gaagaucugg caucacaccu ucuacaauga acuccgagug
gcuccagagg aacacccaau ccugcugacu gaggcucccc ugaacccaaa ggccaacagg
gagaagauga cucaaaucau guuugagacc uucaacaccc ccgccaugua uguugccauc
caggccgugc ugucccucua cgcuuccggc cguaccacug guauugugcu ggacucuggu
gacggcgucu cccacaccgu acccaucuau gaagguuacg cauugcccca ugccauccug
cgucuggacu uggccggccg ugacuugacu gacuaccuga ugaagauccu gaccgagcgu
ggcuacagcu ucacaacuac agcaga SEQ ID NO 64; RNA; Blattella germanica; u can be t (for DNA complement)

uggcaucaca ccuucuacaa ugaacuccga guggcuccag aggaacaccc aauccugcug
acugaggcuc cccugaaccc aaaggccaac agggagaaga ugacucaa SEQ ID NO 65; DNA; synthetic Bg001 fragment tatgctccaagaccaagcacaggacctcacaagttacgagagagtctgcc

FIG. 5 CONT'D

SEQ ID NO 66; DNA; synthetic Bg001 fragment cttgggtcgtgttggaactgtagttaatcgagaacgtcatcctggttcct SEQ ID NO 67; DNA; synthetic Bg001 concatemer 1 tatgctccaagaccaagcacaggacctcacaagttacgagagagtctgcctatgctccaagaccaagcacaggacctcacaa
gttacgagagagtctgcctatgctccaagaccaagcacaggacctcacaagttacgagagagtctgcctatgctccaagacca
agcacaggacctcacaagttacgagagagtctgcctatgctccaagaccaagcacaggacctcacaagttacgagagagtct
gcc SEQ ID NO 68; DNA; synthetic Bg001 concatemer 2 cttgggtcgtgttggaactgtagttaatcgagaacgtcatcctggttcctcttgggtcgtgttggaactgtagttaatcgagaacgtcat
cctggttcctcttgggtcgtgttggaactgtagttaatcgagaacgtcatcctggttcctcttgggtcgtgttggaactgtagttaatcga
gaacgtcatcctggttcctcttgggtcgtgttggaactgtagttaatcgagaacgtcatcctggttcct SEQ ID NO 69; DNA; synthetic Bg001 fragment gctgaaatatgcattaaccaactgtgaggttaagaaaattgttatgcagcgccttattaaggttgatggaaaagtcagaacagacc
ccaactatccagct SEQ ID NO 70; DNA; synthetic Bg001 concatemer 3 gctgaaatatgcattaaccaactgtgaggttaagaaaattgttatgcagcgccttattaaggttgatggaaaagtcagaacagacc
ccaactatccagctgctgaaatatgcattaaccaactgtgaggttaagaaaattgttatgcagcgccttattaaggttgatggaaaa
gtcagaacagaccccaactatccagctgctgaaatatgcattaaccaactgtgaggttaagaaaattgttatgcagcgccttatta
aggttgatggaaaagtcagaacagaccccaactatccagct

FIG. 5 CONT'D

RNAI FOR THE CONTROL OF INSECTS AND ARACHNIDS

RELATED APPLICATIONS

This application is a national stage filing under 35 U.S.C. §371 of international application PCT/IB2006/002360, filed May 31, 2006, and claims the benefit under 35 U.S.C. §119(e) of U.S. provisional application Ser. No. 60/685,765, filed May 31, 2005.

FIELD OF THE INVENTION

The present invention relates to the field of double-stranded RNA (dsRNA) mediated gene silencing in insect species. More particularly, the present invention relates to genetic constructs designed for the expression of dsRNA corresponding to novel targets identified for the first time herein. These constructs are particularly useful in dsRNA mediated insect pest control, especially control of household insects or arachnids, for instance cockroaches.

BACKGROUND TO THE INVENTION

Pest control and particularly insect and/or arachnid control, especially control of household insects, ecto-parasites and insects relevant for public health and hygiene (e.g. urban protection) such as cockroaches, fleas, ants, termites, earwigs, mosquitos, flies and house crickets is an important field. The presence of insects in locations such as at home, in offices, restaurants, hospitals or warehouses undoubtedly causes distress because there is a common public perception that insects such as cockroaches or flies live in places that are dirty and not well kept.

These insects do not only causes distress but also contaminate food and eating utensils, destroy fabric and paper products and impart stains and unpleasant odours to surfaces they contact. Furthermore, these insects can pose health risks as carriers for bacteria. For example, cockroaches may transmit bacteria that cause food poisoning (*Salmonella* spp. and *Shigella* spp.). German cockroaches are believed capable of transmitting disease-causing organisms such as *Staphylococcus* spp., *Streptococcus* spp., hepatitis virus and coliform bacteria. They also have been implicated in the spread of typhoid and dysentery. Some people, especially those with asthma, are sensitive to the allergens produced by these cockroaches.

There are various chemical insecticides and capturing devices developed and commercially available for fighting household pests. However, increasing efficacy of these means is usually linked with increased health risk. Insecticides may contaminate food which is nearly unavoidable in places such as kitchens, restaurants or food storages and incorporation may cause health risks to humans.

The solution to this problem of contamination has been to use less toxic insecticides. However, when applying less toxic insecticides, there is an increased probability that the insect may become resistant over time. Insecticides act by binding to a certain insect protein, such as an acetylcholine receptor for example, and cause death of the pest species by either deactivating or over-activating the protein. Insecticides have been developed to be safe at certain concentration, but can and do impact on human health when incorporated at higher dosages or over long periods. In contrary to agrochemicals, household insecticides are applied in places where food is stored or prepared and food contamination and contact to humans cannot be avoided.

One alternative to chemical pesticides is to utilise biological agents. Over the last few years, downregulation of genes (also referred to as "gene silencing") in multicellular organisms by means of RNA interference or "RNAi" has become a well-established technique.

In general, RNAi comprises contacting the organism with a double stranded RNA fragment or "dsRNA" (generally either as two annealed complementary single strands of RNA or as a hairpin construct) that comprises a nucleotide sequence that corresponds to (at least part of) the nucleotide sequence of the gene to be downregulated (the "target gene"). Reference is inter alia made to the International application WO 99/32619 (Carnegie Institute of Washington), the International application WO 99/53050 (CSIRO), the International application WO 00/01846 (Devgen) and to Fire et al., Nature, Vol. 391, pp. 806-811, February 1998.

In nematodes, RNAi can be performed by feeding the nematode with the dsRNA fragment as such, or alternatively with a bacterial strain that either contains the dsRNA fragment or that upon ingestion by the nematode is capable of expressing the dsRNA fragment. For this so-called "RNAi by feeding", reference is inter alia made to the International application WO 00/01846 by applicant, and to WO 99/32619 cited above, in which the nematode *C. elegans* is used.

Many dsRNA constructs have been described in the art. A classic dsRNA is produced from a DNA construct comprising two convergent promoters flanking the sequence complementary to the target sequence which needs to be downregulated (see for example WO00/01846 (Devgen)). As the technology of dsRNA mediated gene silencing advanced, new constructs were designed to improve the dsRNA for various purposes.

In order to produce the dsRNA more efficiently, a stem-loop-stem structure or "hairpin" was developed. As described in, for example, document WO 99/53050 (CSIRO), this hairpin allows the formation of dsRNA from one single RNA transcript. The RNA transcript comprises the sense and antisense version of the complementary sequence, separated by a non-complementary loop structure allowing the RNA transcript to fold back and to base pair into a dsRNA stem portion.

DsRNA gene silencing finds application in many different areas, such as for example dsRNA mediated gene silencing in clinical applications (WO2004/001013) and in plants. In plants, dsRNA constructs useful for gene silencing have also been designed to be cleaved and to be processed into Short interfering RNAs (siRNAs).

RNAi has also been proposed as a means of protecting plants against plant parasitic nematodes, i.e. by expressing in the plant (e.g. in the entire plant, or in a part, tissue or cell of a plant) one or more nucleotide sequences that form a dsRNA fragment that corresponds to a target gene in the plant parasitic nematode that is essential for its growth, reproduction and/or survival. Reference may be made to the International application WO 00/01846 by the present applicant, U.S. Pat. No. 6,506,559 (based on WO 99/32619), and to International applications WO 01/96584, WO 01/37654 and WO 03/052110 for a description of such techniques.

Elbashir et al. (Nature, 411, 494-498, 2001) have demonstrated effective RNAi-mediated gene silencing in mammalian cells using dsRNA fragments of 21 nucleotides in length (also termed small interfering RNAs or siRNAs).

WO 03/004644 describes delivery of dsRNA to arthropods in general terms and is incorporated herein by reference. WO 03/004644 details down regulation of the reporter gene GUS (Clonetech) using RNAi in *Drosophila melanogaster* and down regulation of the vATPase gene in *H. armigera*.

WO 01/34815 relates to baculovirus expression vectors which produce dsRNA and the use of these vectors in pest control.

Although the technique of RNAi has been generally known in the art in plants, nematodes and mammalian cells for some years, to date little is known about the use of RNAi to down-regulate gene expression in insects and/or arachnids. In addition, little is known on the application of RNAi to control pest species such as household insects, ecto-parasites and insects and/or arachnids relevant for public health and hygiene.

Constructs suitable and efficient for dsRNA mediated pest control, should meet at least some of the following requirements (1) the dsRNA must be taken up by the pest organisms (2) the dsRNA must have good stability in the pest organisms (3) the dsRNA must be effective in the pest organism to control its viability, growth and/or development and/or (4) the dsRNA must guarantee maximized safety and minimized environmental impact.

It is now the purpose of the present invention to provide dsRNA constructs, which meet the above-mentioned requirements.

DESCRIPTION OF THE INVENTION

The present invention describes a new non-compound based approach for insect and/or arachnid control. The active ingredient is a nucleic acid, a double-stranded RNA (dsRNA), which can be used as an insecticidal or arachnicidal formulation (for example in baits or gel applications). The sequence of the dsRNA matches a part of an essential insect gene and causes down-regulation of the insect target via RNA interference (RNAi). As a result of the down-regulation of mRNA, the dsRNA prevents expression of the corresponding insect protein and hence causes death, growth arrest or sterility of the insect and/or arachnid.

Targets

The present inventors have identified for the first time novel targets for RNAi, which can effectively control insect or arachnid pest populations.

For the avoidance of doubt, a target is defined herein as a gene whose protein product is required for the insect and/or arachnid to maintain its normal physiological and biochemical functions. Inhibition of the expression of the target gene limits the insect's and/or arachnids ability to feed, grow, or survive. Examples of insect and/or arachnid genes that may be employed in the practice of the invention include essential genes, genes involved in processes such as development, metabolism, or neurotransmission, and genes whose products are targets of existing insecticides and/or arachnids. In a preferred embodiment of the invention, the target is part of pathways required for cellular function such as transcription, translation, the cytoskeleton, cell-cycle, metabolism (anabolism or catabolism), endocytosis, intracellular and intercellular transport, calcium binding, nucleus import and export, nucleic acid binding, signal peptidase-protein binding, the proteasome, vesicle transport, neuro-transmission, water-balance, ion-balance, splicing, mitosis, meiosis, chromosome organisation, stability or integrity, micro RNAs, siRNAs, posttranslational protein modifications, electron transport, apoptosis, membrane integrity, and cell adhesion.

The novel target genes identified in the present invention comprise:

A) structural proteins, for instance tropomyosin 1 (GenBank AF260897) (SEQ ID NOs 41 and 42), actin 5C (GenBank AY004248) (SEQ ID NOs 57 and 58), and homologous or heterologous proteins having the same biological function in the same or in other insect and/or arachnid species;

B) metabolic enzymes, for instance the HMG Coenzyme A synthase (GenBank X73679) (SEQ ID NO 49 and 50), and homologous or heterologous proteins having the same biological function in the same or in other insect and/or arachnid species;

C) enzymes involved in ion/pH homeostasis, such as V-ATPase and homologous or heterologous proteins having the same biological function in the same or in other insect and/or arachnid species;

D) enzymes involved in the transcriptional/translational machinery, such as for instance Ribosomal protein S4 homolog (SEQ ID NOs 1 and 2)
Ribosomal protein S9 homolog (SEQ ID NOs 11 and 12)
Ribosomal protein L9 homolog (SEQ ID NOs 21 and 22)
Ribosomal protein L19 homolog (SEQ ID NOs 31 and 32)

Accordingly, according to a first aspect there is provided a nucleic acid molecule comprising the nucleotide sequence as set forth in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180 and 181, or an orthologous nucleotide sequence from an insect and/or arachnid species, wherein the orthologous nucleotide sequence has at least 70%, preferably at least 75%, 80%, 85%, 90%, more preferably at least about 95% and even more preferably at least about 96%, 97%, 98%, most preferably at least 99% sequence identity with the nucleotide sequence of any one of SEQ ID NOs 1, 11, 21 and 31. Preferred orthologous sequences comprise, or if being used according to the methods of the invention include, sequences from household insects, ecto-parasites and insects and/or arachnids relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. More preferred orthologous sequences are from cockroaches (Blattodea) such as but not limited to *Blatella* spp. (e.g. *Blatella germanica* (german cockroach)), *Periplaneta* spp. (e.g. *Periplaneta americana* (American cockroach) and *Periplaneta australiasiae* (Australian cockroach)), *Blatta* spp. (e.g. *Blatta orientalis* (Oriental cockroach)) and *Supella* spp. (e.g. *Supella longipalpa* (brown-banded cockroach); ants (Formicoidea), such as but not limited to *Solenopsis* spp. (e.g. *Solenopsis invicta* (Red Fire Ant)), *Monomorium* spp. (e.g. *Monomorium pharaonis* (Pharaoh Ant)), *Camponotus* spp. (e.g. *Camponotus* spp (Carpenter Ants)), *lasius* spp. (e.g. *Lasius niger* (Small Black Ant)), *Tetramorium* spp. (e.g. *Tetramorium caespitum* (Pavement Ant)), *Myrmica* spp. (e.g. *Myrmica rubra* (Red Ant)), *Formica* spp (wood ants), *Crematogaster* spp. (e.g. *Crematogaster lineolata* (Acrobat Ant)), *Iridomyrmex* spp. (e.g. *Iridomyrmex humilis* (Argentine Ant)), *Pheidole* spp. (Big Headed Ants), and *Dasymutilla* spp. (e.g. *Dasymutilla occidentalis* (Velvet Ant)); termites (Isoptera and/or Termitidae) such as but not limited to *Amitermes* spp. (e.g. *Amitermes floridensis* (Florida dark-winged subterranean termite)), *Reticulitermes* spp. (e.g. *Reticulitermes flavipes* (the eastern subterranean termite), *Reticulitermes hesperus* (Western Subterranean Termite)), *Coptotermes* spp. (e.g. *Coptotermes formosanus* (Formosan Subterranean Termite)), *Incisitermes* spp. (e.g. *Incisitermes minor* (Western Drywood Termite)) and *Neotermes* spp. (e.g. *Neotermes connexus* (Forest Tree Termite)).

According to another aspect there is provided a nucleic acid molecule comprising, consisting essentially of, or consisting of the nucleotide sequence as set forth in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200.

SEQ ID NO's 4, 6, 7, 16, 27, 26, 27, 36 and 37 all represent the nucleotide sequences of specific primers which were utilised to identify the novel sequences of the invention in a selective and specific manner.

The novel identified genes all represent components of the transcriptional/translational machinery of *Blatella germanica*. By inhibiting expression of these genes or by inhibiting expression of the novel identified target genes, through RNAi, an important pest may be controlled.

It is predicted, and would be understood by the skilled person, that also orthologues of these novel target genes represent further targets for down-regulation in the control of other insect and/or arachnid species. Thus, orthologues of the novel nucleic acid molecules of the present invention are also contemplated.

Protein or nucleotide sequences are likely to be homologous if they show a "significant" level of sequence similarity or identity. Truly homologous sequences are related by divergence from a common ancestor gene. Sequence homologues can be of two types: (i) where homologues exist in different species they are known as orthologues. e.g. the α-globin genes in mouse and human are orthologues. (ii) paralogues are homologous genes within a single species. e.g. the α- and β-globin genes in mouse are paralogues. By "orthologues" is meant herein both types of homologues referred to above.

In one embodiment, the orthologue will share at least about 40%, 50% or 60% nucleotide-sequence identity with the nucleotide sequence as set forth in any one of SEQ ID NO 1, 11, 21, 31, 41, 49 or 57. Preferably, the orthologue will share at least about 70%, 75%, 80%, 85%, 90%, more preferably at least about 95% and even more preferably at least about 96%, 97%, 98% or 99% sequence identity with the nucleotide sequence as set forth in any one of SEQ ID NOs 1, 11, 21, 31, 41, 49 or 57.

According to another embodiment, the invention encompasses target genes which are insect or arachnidae orthologues of a gene comprising, consisting essentially of, or consisting of a nucleotide sequence as represented in any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200. By way of example, orthologous may comprise a nucleotide sequence as represented in any of SEQ ID NOs 71 to 200, or a fragment of at least 17, 18, 19, 20, 21, 22, 23, 24, 25, 26 or 27 nucleotides thereof. A non-limiting list of insect or arachnid orthologous genes or sequences comprising at least a fragment of 17 nucleotides of one of the sequences of the invention is given in Tables 4 and 5. The sequences presented in Tables 4 and 5 are intended to form part of the present invention. Thus, orthologues comprise, consist essentially of or consist of any of the sequences set forth in Tables 4 and 5.

According to another aspect, the invention thus encompasses any of the methods described herein for controlling insect and/or arachnid infestation or infection, comprising contacting insects and/or arachnids with a double-stranded RNA, wherein the double-stranded RNA comprises annealed complementary strands, one of which has a nucleotide sequence which is complementary to at least part of the nucleotide sequence of a target gene comprising a fragment of at least 17, 18, 19, 20 or 21 nucleotides of any of the sequences as represented in SEQ ID NOs 71 to 200, whereby the double-stranded RNA is taken up by the insect and/or arachnid and thereby controls growth, kills or prevents infestation or infection by the insect and/or arachnid. Said insect and/or arachnid may comprise, consist essentially of or consist of any target organisms/species described herein.

Related nucleic acid molecules encompassed by the invention may also be defined in terms of hybridisation to a nucleic acid molecule comprising the nucleotide sequence of any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180 and 181. Preferably, the hybridisation conditions are moderate stringency hybridisation conditions and even more preferably high stringency hybridisation conditions. Such conditions of moderate and high stringency would be immediately familiar to one of skill in the art. For example, a hybridization reaction incubated at 42° C. in a solution comprising 50% formamide, 5×SSC, and 1% SDS or at 65° C. in a solution comprising 5×SSC and 1% SDS, with a wash in 0.2×SSC and 0.1% SDS at 65° C. represent suitable high stringency conditions.

The invention also provides the protein products of these novel target genes, and orthologues thereof.

Accordingly, according to a second aspect there is provided a protein comprising the amino acid sequence as set forth in any one of SEQ ID NOs 2, 12, 22 or 32 or an orthologous protein having a conserved amino acid sequence from a further insect and/or arachnid species.

As mentioned above, it is predicted also that orthologues of the novel target genes will represent further targets for down-regulation in the control of other insect and/or arachnid species. Thus, orthologues of the novel protein molecules of the present invention are also contemplated.

In one embodiment, the orthologue will share at least about 40% amino acid sequence identity with the amino acid sequence as set forth in any one of SEQ ID NOs 2, 12, 22 or 32. Preferably, the orthologue will share at least about 40%, 50%, 60%, 65%, 70%, 80%, more preferably at least about 90% and even more preferably at least about 96%, 97%, 98% or 95% amino acid sequence identity with the amino acid sequence as set forth in any one of SEQ ID NOs 2, 12, 22 or 32.

In another embodiment, the invention also provides for a nucleic acid encoding a protein comprising the amino acid sequence as set forth in any one of SEQ ID NOs 2, 12, 22 or 32. The nucleic acid molecules encompassed by this aspect of the invention also include those which are functionally equivalent in that they encode the same protein molecule. Thus, all nucleic acid molecules which are possible due to the degeneracy of the genetic code are intended to fall within the scope of this aspect of the invention.

Target Organisms/Species

The "target species" as used in the present invention, may be any insect or arachnid species which represents a pest. The term also relates to the insect or arachnid at any stage in its development. Because insects have a non-living exoskeleton, they cannot grow at a uniform rate and rather grow in stages by periodically shedding their exoskeleton. This process is referred to as moulting or ecdysis. The stages between moults are referred to as "instars" and this stage may be targeted according to the invention. Also, insect eggs or live young may also be targeted according to the present invention. All stages in the developmental cycle, which includes metamorphosis in the pterygotes, may be targeted by RNAi according to the present invention. Thus, individual stages such as larvae, pupae, nymph etc stages of development may all be targeted.

The target species may be any insect or arachnid, meaning any organism or species belonging to the Kingdom Animals, more specifically to the Phylum Arthropoda, and to the Class Insecta or the Class Arachnida. The methods of the invention are applicable to all insects and arachnids that are susceptible to gene silencing by RNA interference and that are capable of internalising double-stranded RNA from their surrounding environment.

In one embodiment of the invention, the insect or arachnid may belong to the following orders: Acari, Arachnida, Anoplura, Blattodea, Coleoptera, Collembola, Dermaptera, Dictyoptera, Diplura, Diptera, Embioptera, Ephemeroptera, Grylloblatodea, Hemiptera, Heteroptera, Homoptera, Hymenoptera, Isoptera, Lepidoptera, Mallophaga, Mecoptera, Neuroptera, Odonata, Orthoptera, Phasmida, Phithiraptera, Plecoptera, Protura, Psocoptera, Siphonaptera, Siphunculata, Thysanura, Sternorrhyncha, Strepsiptera, Thysanoptera, Trichoptera, Zoraptera and Zygentoma.

In preferred, but non-limiting, embodiments of the invention the insect or arachnid is chosen from the group consisting of:

(1) Acari: mites including Ixodida (ticks)
(2) Arachnida: Araneae (spiders) and Opiliones (harvestman), examples include: *Latrodectus mactans* (black widow) and *Loxosceles recluse* (Brown Recluse Spider)
(3) Anoplura: lice, such as *Pediculus humanus* (human body louse)
(4) Blattodea: cockroaches including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). A most preferred target is German cockroach (*Blatella germanica*).
(5) Coleoptera: beetles, examples include: the family of Powderpost beetle (family of Bostrichoidea); *Dendroctonus* spp. (Black Turpentine Beetle, Southern Pine Beetle, IPS Engraver Beetle); Carpet Beetles (*Anthrenus spp, Attagenus* spp); Old House Borer (family of Cerambycidae: *Hylotrupes bajulus*); *Anobium punctatum; Tribolium* spp (flour beetle); *Trogoderma granarium* (Khapra Beetle); *Oryzaephilus sarinamensis* (Toothed Grain Beetle) etc. (Bookworm)
(6) Dermaptera: family of earwigs
(7) Diptera: mosquitoes (Culicidae) and flies (Brachycera), examples are: Anophelinae such as *Anopheles* spp. and Culicinae such as *Aedes fulvus*; Tabanidae such as *Tabanus punctifer* (Horse Fly), *Glossina morsitans* morsitans (tsetse fly), drain flies (Psychodidae) and Calyptratae such as *Musca domestica* (House fly), flesh flies (family of Sarcophagidae) etc.
(8) Heteroptera: bugs, such as *Cimex lectularius* (bed bug)
(9) Hymenoptera: wasps (Apocrita), including ants (Formicoidea), bees (Apoidea): *Solenopsis invicta* (Red Fire Ant), *Monomorium pharaonis* (Pharaoh Ant), *Camponotus* spp (Carpenter Ants), *Lasius niger* (Small Black Ant), *tetramorium caespitum* (Pavement Ant), *Myrmica rubra* (Red Ant), *Formica* spp (wood ants), *Crematogaster lineolata* (Acrobat Ant), *Iridomyrmex humilis* (Argentine Ant), *Pheidole* spp. (Big Headed Ants, *Dasymutilla occidentalis* (Velvet Ant) etc.
(10) Isoptera: termites, examples include: *Amitermes floridensis* (Florida dark-winged subterranean termite), the eastern subterranean termite (*Reticulitermes flavipes*), the *R. hesperus* (Western Subterranean Termite), *Coptotermes formosanus* (Formosan Subterranean Termite), *Incisitermes minor* (Western Drywood Termite), *Neotermes connexus* (Forest Tree Termite) and Termitidae
(11) Lepidoptera: moths, examples include: Tineidae & Oecophoridae such as *Tineola bisselliella* (Common Clothes Moth), and Pyralidae such as *Pyralis farinalis* (Meal Moth) etc
(12) Psocoptera: booklice (Psocids)
(13) Siphonaptera: fleas such as *Pulex irritans*
(14) Sternorrhyncha: aphids (Aphididae)
(15) Zygentoma: silverfish, examples are: *Thermobia domestics* and *Lepisma saccharine*

Preferred target insects or arachnids include household insects, ecto-parasites and insects and/or arachnids relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. More preferred targets are cockroaches (Blattodea) such as but not limited to *Blatella* spp. (e.g. *Blatella germanica* (german cockroach)), *Periplaneta* spp. (e.g. *Periplaneta americana* (American cockroach) and *Periplaneta australiasiae* (Australian cockroach)), *Blatta* spp. (e.g. *Blatta orientalis* (Oriental cockroach)) and *Supella* spp. (e.g. *Supella longipalpa* (brown-banded cockroach); ants (Formicoidea), such as but not limited to *Solenopsis* spp. (e.g. *Solenopsis* invicta (Red Fire Ant)), *Monomorium* spp. (e.g. *Monomorium pharaonis* (Pharaoh Ant)), *Camponotus* spp. (e.g. *Camponotus* spp (Carpenter Ants)), *Lasius* spp. (e.g. *Lasius niger* (Small Black Ant)), *Tetramorium* spp. (e.g. *Tetramorium caespitum* (Pavement Ant)), *Myrmica* spp. (e.g. *Myrmica rubra* (Red Ant)), *Formica* spp (wood ants), *Crematogaster* spp. (e.g. *Crematogaster lineolata* (Acrobat Ant)), *Iridomyrmex* spp. (e.g. *Iridomyrmex humilis* (Argentine Ant)), *Pheidole* spp. (Big Headed Ants), and *Dasymutilla* spp. (e.g. *Dasymutilla occidentalis* (Velvet Ant)); termites (Isoptera and/or Termitidae) such as but not limite to *Amitermes* spp. (e.g. *Amitermes floridensis* (Florida dark-winged subterranean termite)), *Reticulitermes* spp. (e.g. *Reticulitermes flavipes* (the eastern subterranean termite), *Reticulitermes hesperus* (Western Subterranean Termite)), *Coptotermes* spp. (e.g. *Coptotermes formosanus* (Formosan Subterranean Termite)), *Incisitermes* spp. (e.g. *Incisitermes minor* (Western Drywood Termite)), *Neotermes* spp. (e.g. *Neotermes connexus* (Forest Tree Termite)). More preferred targets are cockroaches. A most preferred target is German cockroach (*Blatella germanica*).

RNA Constructs

By "complementary" is meant that the RNA strand represents the RNA equivalent of the specified sequence if that sequence is a DNA sequence or the RNA equivalent of the complement of the DNA sequence.

The present invention relates to additional targets for RNAi mediated down regulation of gene expression. For all targets identified herein, there is provided in a further aspect of the invention an RNA construct comprising a double stranded RNA region, at least one strand of which comprises a nucleotide sequence that is complementary to a portion of the nucleotide sequence of any one of any one of (i) the target nucleic acid molecules defined in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180 and 181; or (ii) the nucleic acid molecules comprising the nucleotide sequence as set forth in any one of SEQ ID NOs 41, 43, 44, 47, 48, 109 to 147, 182 to 187, 49, 51, 52, 55, 56, 148 to 150, 57, 63, 64, 151 to 179, and 188 to 200, or an orthologous nucleotide sequence thereof from an insect and/ or arachnid species. As described above, the orthologue may share at least about 50% nucleotide sequence identity with the nucleotide sequence as set forth in any one of SEQ ID NO's 1, 4, 6, 7, 11, 16, 17, 21, 26, 27, 31, 36, 37, 41, 43, 44, 49, 51, 52 and 57. Preferably, the orthologue will share at least about 70%, 75%, 80%, 85%, 90%, more preferably at least about 95% and even more preferably at least about 96%, 97%, 98% or 99% sequence identity with the nucleotide sequence as set forth in any one of SEQ ID NO's 1, 4, 6, 7, 11, 16, 17, 21, 26, 27, 31, 36, 37, 41, 43, 44, 49, 51, 52 and 57.

As aforementioned, the orthologues of targets identified herein in *Blatella germanica* are considered to be viable targets in other insect and/or arachnid species, including household insects and/or arachnids, ecto-parasites and insects relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas.

Most preferred targets are derived from cockroaches, for example cockroaches of the genus *Blatella*, including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). The most preferred target is German cockroach (*Blatella germanica*), in which the novel targets have been identified.

It has been previously reported that the formation of short interfering RNAs (siRNAs) of about 21 bp is desirable for effective gene silencing. However, in applications of applicant it has been shown that the minimum length of dsRNA preferably is at least about 80-100 bp in order to be efficiently taken up by certain pest organisms. There are indications that in invertebrates such as the free living nematode *C. elegans* or the plant parasitic nematode *Meloidogyne incognita* these longer fragments are more effective in gene silencing, possibly due to a more efficient uptake of these long dsRNA by the invertebrate.

It has also recently been suggested that synthetic RNA duplexes consisting of either 27-mer blunt or short hairpin (sh) RNAs with 29 bp stems and 2-nt 3' overhangs are more potent inducers of RNA interference than conventional 21-mer siRNAs (see Williams, Nature Biotechnology Vol 23, 2, February 2005, 181 and Kim et al, Nature Biotechnology Vol 23, 2, February 2005, 222-229 and Siolas et al, Nature Biotechnology Vol 23, 2, February 2005, 227-231 which references are incorporated herein in their entirety). Thus, molecules based upon the targets identified above and being either 27-mer blunt or short hairpin (sh) RNA's with 29-bp stems and 2-nt 3'overhangs are also included within the scope of the invention.

Therefore, in one embodiment, the RNA construct has a double stranded RNA region which has a length of at least about 17 bp, preferably at least about 21 bp, more preferably between about 20-1500 bp, even more preferably between about 80-1000 bp and most preferably between about 17-27 bp or between about 80-250 bp; such as double stranded RNA regions of about 17 bp, 18 bp, 20 bp, 21 bp, 22 bp, 23 bp, 24 bp, 25 bp, 26 bp, 27 bp, 50 bp, 80 bp, 100 bp, 150 bp, 200 bp, 250 bp, 300 bp, 350 bp, 400 bp, 450 bp, 500 bp, 550 bp, 600 bp, 650 bp, 700 bp, 900 bp, 100 bp, 1100 bp, 1200 bp, 1300 bp, 1400 bp or 1500 bp.

The upper limit on the length of the double-stranded RNA may be dependent on i) the requirement for the dsRNA to be taken up by the insect and/or arachnid and ii) the requirement for the dsRNA to be processed within the relevant cell into fragments that direct RNAi. The chosen length may also be influenced by the method of synthesis of the RNA and the mode of delivery of the RNA to the cell. Preferably the double-stranded RNA to be used in the methods of the invention will be less than 10,000 bp in length, more preferably 1000 bp or less, more preferably 500 bp or less, more preferably 300 bp or less, more preferably 100 bp or less.

Efficacy in terms of pest control may be increased by targeting multiple target genes with a single RNA construct. Thus, the pest is less likely to survive and acquire resistance because there will be multiple double stranded RNA's mediating RNA interference, possibly all at the same time or possibly in a cascaded manner.

The methods of the invention encompass the simultaneous or sequential provision of two or more different double-stranded RNAs or RNA constructs to the same insect and/or arachnid, so as to achieve down-regulation or inhibition of multiple target genes or to achieve a more potent inhibition of a single target gene.

According to a further embodiment, the RNA constructs according to the invention comprise at least one double stranded RNA region, at least one of which comprises a nucleotide sequence that is complementary to a portion of any of the nucleotide sequences described herein, wherein the complementarity of said nucleotide sequence comprises at least 70%, preferably at least 75%, 80%, 85%, 90%, more preferably at least about 95% and even more preferably at least about 96%, 97%, 98% or 99% sequence identity with (i) the portion of the nucleotide sequence of the nucleic acid molecules as set forth in any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180 and 181 or (ii) the nucleic acid molecules comprising the nucleotide sequence as set forth in any one of SEQ ID NOs 41, 43, 44, 47, 48, 109 to 147, 182 to 187, 49, 51, 52, 55, 56, 148 to 150, 57, 63, 64, 151 to 179, and 188 to 200, or an orthologous nucleotide sequence thereof from an insect and/or arachnid species, wherein the percentage sequence identity is calculated over the same length.

With "over the same length" is meant that when % identity is calculated between sequences, this is done over the corresponding stretch of nucleotideds in both sequences.

Alternatively, multiple target genes are down regulated by the provision of one double-stranded RNA that acts against multiple target sequences. Alternatively, a single target may be more efficiently inhibited by the presence of more than one copy of the double stranded RNA fragment corresponding to the target gene. Thus, in one embodiment of the invention, the double-stranded RNA construct comprises multiple dsRNA regions, at least one strand of each dsRNA region comprising a nucleotide sequence that is complementary to at least part of a target nucleotide sequence of an insect and/or arachnid target gene. According to the invention, the dsRNA regions in the RNA construct may be complementary to the same or to different target genes and/or the dsRNA regions may be complementary to target genes from the same or from different insect and/or arachnid species.

Accordingly, the invention provides an isolated double stranded RNA or RNA construct of the invention which comprises at least two double stranded RNA regions, at least one strand of each of which comprises, consists essentially of, or consists of a nucleotide sequence that is complementary to a portion of the nucleotide sequence of any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, or an orthologous nucleotide sequence from an insect and/or arachnid species, wherein the orthologous nucleotide sequence has at least 70%, 80%, 85%, 87.5%, 90%, 95% or at least 99% sequence identity with at least the relevant portion of the nucleotide sequence of any one of SEQ ID NOs 1, 11, 21 and 31 or the nucleic acid molecules comprising the nucleotide sequence as set forth in any one of SEQ ID NOs 41, 43, 44, 49, 51, 52 and 57. Preferably said double stranded RNA or RNA construct comprises, consists essentially of or consists of one or at least two nucleotide sequences independently chosen from any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, preferably any of SEQ ID NOs 65 to 70.

Thus, in one embodiment of the invention, the RNA construct comprises multiple dsRNA regions, at least one strand of each dsRNA region comprising a nucleotide sequence that is complementary to a portion of the nucleotide sequence of a target gene from the insect and/or arachnid species. According to the invention, the dsRNA regions in the RNA construct may be complementary to the same or to different target genes; the dsRNA regions may be complementary to targets from the same or from different insect species.

The dsRNA regions may be combined as follows:

a) when multiple dsRNA regions targeting a single target gene are combined, they may be combined in the original order (ie the order in which the fragments appear in the target gene) in the RNA construct, b) alternatively, the original order of the fragments may be ignored so that they are scrambled and combined randomly or deliberately in any order into the RNA construct, c) alternatively, one single fragment may be repeated several times, for example from 1 to 10 times, e.g. 1, 2, 3, 4, 5, 6, 7, 8, 9 or 10 times in the RNA construct, or d) the dsRNA regions (targeting a single or different target genes) may be combined in the sense or antisense orientation.

In addition, the target gene(s) to be combined may be chosen from one or more of the following categories of genes (including all possible combinations thereof, as appropriate):

e) "essential" genes or "pathogenicity genes" encompass genes that are vital for one or more target insects and/or arachnids and result in a lethal or severe (e.g. movement, feeding, paralysis, drinking, fertility, reproduction, growth) phenotype when silenced. The choice of a strong lethal target gene results in a potent RNAi effect. In the RNA constructs of the invention, multiple dsRNA regions targeting the same or different (very effective) lethal genes can be combined to further increase the potency, efficacy or speed of the RNAi effect in insect and/or arachnid control.

f) "weak" genes encompass target genes with a particularly interesting function in one of the cellular pathways described herein, but which result in a weak phenotypic effect when silenced independently. In the RNA constructs of the invention, multiple dsRNA regions targeting a single or different weak gene(s) may be combined to obtain a stronger RNAi effect.

g) "insect and/or arachnid specific" genes encompass genes and portions of genes that have no substantially homologous counterpart in non-pest organisms as can be determined by bioinformatics homology searches, for example by BLAST searches. The choice of an insect and/or arachnid specific target gene or portion thereof results in a species specific RNAi effect, with no effect or no substantial (adverse) effect in non-target organisms.

h) "conserved genes" encompass genes that are conserved (at the amino acid level) between the target organism and non-target organism(s). To reduce possible effects on non-target species, such effective but conserved genes are analysed and target sequences from the variable regions of these conserved genes are chosen to be targeted by the dsRNA regions in the RNA construct. Here, conservation is assessed at the level of the nucleic acid sequence. Such variable regions thus encompass the least conserved sections, at the level of the nucleic acid sequence, of the conserved target gene(s).

i) "conserved pathway" genes encompass genes that are involved in the same biological pathway or cellular process, or encompass genes that have the same functionality in different insect and/or arachnid species resulting in a specific and potent RNAi effect and more efficient pest control;

j) alternatively, the RNA constructs according to the present invention target multiple genes from different biological pathways, resulting in a broad, cellular RNAi effect and more efficient insect and/or arachnid control.

Preferably, all double stranded RNA regions comprise at least one strand that is complementary to a portion of the nucleotide sequence of any one of SEQ ID NO 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200. However, provided one of the double stranded RNA regions comprises at least one strand that is complementary to a portion of the nucleotide sequence of any one of SEQ ID NO 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, the other double stranded RNA regions may comprise at least one strand that is complementary to a portion of any target gene from the insect and/or arachnid species (including known target genes).

The invention also provides any of the RNA constructs herein described, further comprising at least one additional functional sequence and optionally a linker. In one embodiment, the multiple dsRNA regions are connected by one or more linkers. In another embodiment, the linker is present at a site in the RNA construct, separating the dsRNA regions from another region of interest. Different linker types for the dsRNA constructs are provided by the present invention.

"Conditionally self-cleaving linkers" are RNA sequences capable of being processed under certain conditions. One example of suitable conditionally self-cleaving linkers are RNA sequences that are self-cleaving at low pH conditions. Suitable examples of such RNA sequences are described by Jayasena and Gold (Proc Natl Acad Sci USA. 1997 Sep. 30; 94(20):10612-7), which document is incorporated herein by reference.

Another example of suitable conditionally self-cleaving linkers are RNA sequences that are self-cleaving at high pH conditions. Suitable examples of such RNA sequences are described by Borda et al. (Nucleic Acids Res. 2003 May 15; 31(10):2595-600), which document is incorporated herein by reference. This sequence originates from the catalytic core of the hammerhead ribozyme HH16.

In one aspect of the invention, the linkers may be used to disconnect smaller dsRNA regions in the pest organism. Advantageously, in this situation the linker sequence may promote division of a long dsRNA into smaller dsRNA regions under particular circumstances, resulting in the release of separate dsRNA regions under these circumstances and leading to more efficient gene silencing by these smaller dsRNA regions.

In another aspect of the invention, a linker is located at a site in the RNA construct, separating the dsRNA regions from another sequence of interest, which preferably provides some additional function to the RNA construct. Non-limiting examples of other functional sequences (of interest) which may be incorporated in the RNA construct are for instance (i) additional sequences to facilitate large-scale production of the dsRNA construct; (ii) additional sequences to increase/decrease stability of dsRNA; (iii) additional sequences to bind to proteins or other molecules in a composition to facilitate uptake by the pest species; (iv) additional sequences that are aptamers and that bind to receptors or to molecules in the gut of the pest species to facilitate uptake, endocytosis and/or transcytosis by the pest species; (v) additional sequences to catalyze processing of dsRNA regions.

According to a particular embodiment the pest species has a gut system, such as for example insects and/or arachnids, and the linker is self-cleaving in the gut of the insect and/or arachnid. The pH in the gut is variable ranging from extremely acid to extremely basic.

Alternatively, the linkers are self-cleaving in the endosomes. This may be advantageous when the constructs of the present invention are taken up by the pest organisms via endocytosis or transcytosis, and are therefore compartmentalized in the endosomes of the pest species. The endosomes may have a low pH environment, leading to cleavage of the linker.

The above mentioned linkers that are self cleaving in hydrophobic conditions are particularly useful in dsRNA constructs of the present invention when used to be transferred from one cell to another via the transit in a cell wall, for example when crossing the cell wall of an insect and/or arachnid pest organism.

An intron may also be used as a linker. An "intron" as used herein may be any non-coding RNA sequence of a messenger RNA. Particular suitable intron sequences for the constructs of the present invention (1) are U-rich (35-45%); (2) have an average length of 100 bp (varying between about 50 and about 500 bp) which base pairs may be randomly chosen or may be based on known intron sequences; (3) start at the 5' end with -AG:GT- or -CG:GT- and/or (4) have at their 3' end -AG:GC- or -AG:AA.

A non-complementary RNA sequence, ranging from about 1 base pair to about 10,000 base pairs, may also be used as a linker.

As described above the dsRNA regions of the invention may correspond to only a portion of the target gene, provided that the complementarity is such that RNAi can occur to effectively control the insect and/or arachnid pest. It is not essential to the invention that the full length sequence of the pertinent target gene is known, as long as the dsRNA region containing construct used is capable of down-regulating the target gene.

For example, it is possible to use a dsRNA fragment based on a partial gene sequence (such as an EST) from the insect and/or arachnid, as long as said partial sequence is an ortholog of one of the sequences described as SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200. The degree of sequence homology or complementarity is determined over the length of the dsRNA fragment used.

Furthermore, it is also possible in the invention to use dsRNA fragments that differ from the nucleic acid molecules comprising the sequences described in SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200 in one or more nucleotide positions (e.g. by a deletion, insertion or substitution), as long as the resulting dsRNA fragment is still capable of downregulating the target gene.

Preferably, the dsRNA fragment in the RNA construct has a complementarity, or level of homology comprising at least about 70% nucleotide sequence identity, preferably at least about 80% sequence identity, even more preferably at least about 85% or 87.5% sequence identity, still more preferably about 90% sequence identity, still more preferably at least about 95% sequence identity and most preferably at least about 96%, 97%, 98% or 99% sequence identity with the relevant portion of the nucleotide sequence of any one of the target nucleic acid molecules comprising the nucleotide sequence as set forth in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, or an orthologous nucleotide sequence from an insect and/or arachnid species.

Methods for determining sequence identity are routine in the art and include use of the Blast software and GAP analysis (GCG program). High levels of sequence identity (complementarity) of at least one strand of the dsRNA with the target gene are required to mediate effective RNAi, and thus pest control.

However, it is equally advantageous that the dsRNA regions of the invention are selective to the pest target sequence versus the sequences of mammalian orthologues. This is especially relevant in the present invention where the pest must be controlled in an environment, such as a kitchen, where food is present and in which humans and other mammals may be exposed to compositions designed to control the pest. A selective biological agent is preferable to a chemical agent which may be equally toxic to a mammal, as it is to the pest species.

Furthermore, for a biological agent such as the RNA constructs of the present invention, there is the advantage that the molecules will biodegrade over time and thus will pose less of an environmental and health risk to human users than a chemical agent (such as the known insecticides).

Thus, according to a preferred embodiment, the at least one strand of the double stranded RNA in the RNA construct which comprises a nucleotide sequence that is complementary to a portion of the nucleotide sequence of a nucleic acid molecule as set forth in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, or an orthologous nucleotide sequence from an insect and/or arachnid species has less than about 5%, less than about 10%, less than about 12.5%, less than about 15%, less than about 20%, less than about 30%, less than about 40% sequence identity with the corresponding (orthologous) nucleotide sequence from a mammalian species. In one embodiment, there is no sequence identity with mammalian sequences over 21 contiguous nucleotides. In another embodiment, there is less than about 10% or less than about 12.5% sequence identity over 24 contiguous nucleotides with the corresponding nucleotide sequence from a mammalian species. Preferably, the mammalian species is a human.

In one embodiment, the at least one strand (of the double stranded RNA in the RNA construct which comprises a nucleotide sequence that is complementary to a portion of the nucleotide sequence of a nucleic acid molecule as set forth in any one of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200 or an orthologous nucleotide sequence from an insect and/or arachnid species) comprises at least 17 nucleotides, preferably at least 18 nucleotides, 19 nucleotides, 20 nucleotides, 21 nucleotides, 24 nucleotides, 27 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 900 nucleotides, 1000 nucleotides, 1100 nucleotides, 1200 nucleotides or 1300 nucleotides of any of the nucleic acid molecules comprising the nucleotide sequence as set forth in any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, or the complement thereof.

An RNA construct is also provided comprising at least one double stranded RNA region, at least one strand of which comprises at least about 17 nucleotides, preferably at least about 18 nucleotides, 19 nucleotides, 20 nucleotides, 21 nucleotides, 23 nucleotides, 24 nucleotides, 25 nucleotides, 27 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 900 nucleotides, 1000 nucleotides, 1100 nucleotides, 1200 nucleotides or about 1300 nucleotides of any of the nucleic acid molecules comprising the nucleotide sequence as set forth in any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200, or the complement thereof.

DNA and Expression Constructs and Host Cells

In a further aspect, the invention also provides a DNA construct comprising the nucleotide sequence of the novel targets of the invention, as represented in SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180, 181, 41, 43, 44, 47, 48, 109 to 147, 182 to 187, 49, 51, 52, 55, 56, 148 to 150, 57, 63, 64, 151 to 179, and 188 to 200.

The invention further relates to a DNA construct comprising a region encoding an RNA construct of the invention.

The invention also provides, in a still further aspect, an expression construct comprising any of the DNA constructs of the invention.

The expression construct is such that it is capable, under suitable conditions, of providing (through transcription) an RNA construct comprising a dsRNA region as referred to above.

Genetic constructs for expressing dsRNA are well-known in the art: reference is for example made to the constructs described in WO 99/32619; in WO 00/01846 and WO 01/88121 (all Devgen); WO 00/44914 and WO 01/70949, as well as the prior art already mentioned above. As mentioned therein, such constructs may be DNA or RNA (and are preferably DNA) and may be in the form of a suitable expression vector (such as an expression vector suitable for the transformation of and for expression in bacteria) or other expression system. For example, the construct may be present in (for example by transformation) a suitable bacterial or viral system for the production in bacteria or for transformation of insects and/or arachnids, and these and other host cells containing the genetic constructs form a further aspect of the invention.

An expression construct according to the invention will usually contain—besides the sequence(s) encoding the dsRNA fragment itself—suitable regulatory elements (such as promoters, terminators and enhancers) and other elements of such genetic constructs known per se; and may for example express the dsRNA regions as two separate complementary RNA strands that hybridize to form the desired dsRNA region or may express the dsRNA region in the form of a single RNA containing the two complementary strands, that self-hybridize to form a "stem-loop" or "hairpin" structure that contains the desired dsRNA region. All such constructs may be suitably used in the present invention, which is not particularly limited as to the type of construct used, as long as said construct is suitable for expression of a dsRNA which can mediate effective RNAi in an insect and/or arachnid pest.

The constructs themselves may also be constructed in a manner known per se, for which again reference is made to the above prior art references, as well as to the standard handbooks such as Sambrook et al, "Molecular Cloning: A Laboratory Manual"-(2nd. ed.), Vols. 1-3, Cold Spring Harbor Laboratory Press (1989) and F. Ausubel et al, eds., "Current protocols in molecular biology", Green Publishing and Wiley Interscience, New York (1987).

The dsRNA regions may be expressed preferably in a bacterial host under the control of a constitutive promoter or an inducible promoter (e.g. a promoter that is induced by a specific compound, by damage to the bacteria, etc.). The constitutive or inducible promoter may be non-specific or specific (for example, for a specific part of the life cycle of the bacteria).

The bacterial host cell may need to be inactivated before being utilised as a biological pesticide. This may be done by any technique known in the art, such as by heating or by treatment with phenol or formaldehyde for example. Alternatively, an inactivated virus, such as a suitably modified baculovirus may be utilised in order to deliver the dsRNA regions of the invention to the insect and/or arachnid pest.

The expression constructs may further contain all other elements known per se for nucleic acid sequences or genetic constructs, such as promoters or other control elements, terminators, translation or transcription enhancers, integration factors, signal sequences, selection markers, etc., that are preferably suited for use in a bacterial cell. The sequences that encode these further elements of the construct may again be either isolated from a suitable biological source, or provided synthetically.

Some specific, but non-limiting examples of suitable promoters include, but are not limited to, promoters from an RNA PolI, an RNA PolII, an RNA PolIII, T7 RNA polymerase, T3 RNA polymerase or SP6 RNA polymerase, and also the promoters and other regulatory elements referred to in the prior art cited above, such as in WO 00/01846 for example. The invention further provides bacterial promoters that can direct expression of single stranded RNA, which can upon expression form a hairpin secondary structure containing a loop and a double stranded RNA region are utilised.

Specific, but non-limiting examples of transformation techniques for introducing the constructs into bacterial or viral hosts include transformation, electroporation, transfection etc.

The invention thus provides an expression construct comprising: (a) a nucleic acid encoding an RNA construct as described herein; (b) one or more control sequences capable of driving expression of the nucleic acid of (a); and optionally (c) a transcription termination sequence.

The expression constructs may be inserted into a plasmid or a vector, which may be commercially available. According to one embodiment of the present invention, the expression construct is a bacterial expression vector, suitable for transformation into bacteria and suitable for maintenance and expression of an RNA construct according to the present invention in a transformed bacterial cell. Reference is hereby made to the plasmids and vectors described in WO 01/01846 by applicant, which reference is incorporated herein in its entirety. An alternative is to use a virus cell which can infect an insect species, such as the viruses described in WO 01/34815, which reference is incorporated herein in its entirety.

The term "control sequence" as used herein is to be taken in a broad context and refers to regulatory nucleic acid sequences capable of driving and/or regulating expression of the sequences to which they are ligated and/or operably linked. According to one embodiment of the present invention, the control sequence is operable in a bacterium or virus; preferably the control sequence is a derived from a bacterial sequence. The term "control sequence" encompasses a promoter or a sequence capable of activating or enhancing expression of a nucleic acid molecule in a ceH, tissue or organ.

Optionally, one or more transcription termination sequences may also be incorporated in the expression construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

The expression constructs of the invention may further include an origin of replication which is required for maintenance and/or replication in a specific cell type.

One example is when a expression construct is required to be maintained in a bacterial cell as an episomal genetic element (e.g. plasmid or cosmid molecule) in a cell. Preferred origins of replication include, but are not limited to, f1-ori and colE1 ori.

The expression construct may optionally comprise a selectable marker gene. As used herein, the term "selectable marker gene" includes any gene, which confers a phenotype on a cell in which it is expressed to facilitate the identification and/or selection of cells, which are transfected or transformed, with an expression construct of the invention. Examples of suitable selectable markers include resistance genes against ampicillin ($Amp^r$), tetracydine ($Tc^r$), kanamycin ($Kan^r$), phosphinothricin, and chloramphenicol (CAT) gene. Other suitable marker genes provide a metabolic trait, for example manA. Visual marker genes may also be used and include for example beta-glucuronidase (GUS), luciferase and Green Fluorescent Protein (GFP).

Thus, as described above, the invention provides a host cell comprising an RNA construct and/or a DNA construct and/or an expression construct of the invention. Preferably, the host cell is a bacterial cell, but may be a virus for example. A virus such as a baculovirus may be utilised which specifically infects insects and/or arachnids. This ensures safety for mammals, especially humans, since the virus will not infect the mammal, so no unwanted RNAi effect will occur.

The bacterial cell or virus preferably should be inactivated prior to use as a delivery agent for mediating RNAi in an insect pest when the agent is to be used in an environment where contact with humans or other mammals is likely (such as a kitchen as discussed above). Inactivation may be achieved by any means, such as by heat treatment, phenol or formaldehyde treatment for example.

A method for generating the RNA constructs of the invention is also provided. This method comprises the steps of a. contacting a DNA construct of the invention or an expression construct of the invention with cell-free components; or b. administering a DNA construct of the invention or an expression construct of the invention to a cell, under conditions that allow transcription of said DNA construct to produce said RNA construct.

Thus, an in vitro method is provided, wherein the necessary components for transcription are provided. These components would be immediately familiar to one of skill in the art and numerous in vitro expression kits are commercially available.

Alternatively, the expression may be driven in a host cell. Preferably, the cell is a bacterial cell, but may be a virus for example.

Furthermore, in a further aspect of the invention, the host cells of the invention may be used as source for production of the dsRNA molecules and RNA constructs of the invention. For example, bacterial host cells, containing the expression construct of the invention (as hereinbefore described) may be cultured under suitable conditions (for example at 37° C. or 42° C.) in order to produce the RNA constructs of the invention in effective amounts. Large scale bacterial fermentation and harvesting processes are well known in the art and are utilised commercially. Bacterial culture may be carried out in any suitable media, such as for example LB broth, optionally supplemented with suitable antibiotics such as ampicillin, carbenicillin or chloramphenicol where an antibiotic resistant host strain is being utilised.

The resultant bacterial cultures thus produce the RNA constructs of the invention in large quantities. The bacteria themselves may be formulated into a suitable pesticide composition as described herein, or may be used as a direct (food) source of the RNA constructs of the invention for uptake, for example by ingestion, by a target insect or arachnid.

Similarly, in one embodiment, the bacteria may be used as a source of dsRNA by disrupting or otherwise inactivating the bacteria, as discussed above. For example, the cells may be ruptured or lysed using any suitable means, such as by osmotic shock for example, and the lysate or other suitable cellular fraction or extract of the bacteria utilised in the compositions of the invention.

In one embodiment, the bacterial extract or lysate may be suitably purified to leave a substantially pure RNA construct containing extract. Preferably, substantially all bacterial components are removed from the final dsRNA containing extracts, which may subsequently be formulated into any one of the compositions of the invention. Suitable purification steps are well known in the art and may include, by way of example and not limitation, suitable filtration steps, for example separation on the basis of charge or molecular weight. Suitable hybridization reactions may also be employed in order to purify the dsRNA molecules of interest.

The RNA constructs may be purified to substantial purity by standard techniques, including selective precipitation; column chromatography, immunopurification methods, and others (see, e.g., Scopes, Protein Purification: Principles and Practice (1982); Ausubel et al., supra; and Sambrook et al., supra).

The RNA and DNA constructs, including the double stranded RNA molecules, will typically incorporate natural bases. However, variants are included within the scope of the invention. Thus, the scope of "RNA" and "DNA" encompasses synthetic analogues, including well known sugar-modified bases, which are capable of base pairing and mediating RNAi or of being transcribed to produce RNA respectively in an analogous manner to natural nucleic acids. For example, nucleic acid analogues incorporating non-natural, chemically modified or derivatized bases, or nucleic acid analogues having a modified backbone are envisaged. This applies equally to the linkers which may be incorporated into the constructs of the invention. In particular, the term "double-stranded RNA" or "dsRNA" is to be interpreted as encompassing dsRNA containing non-natural bases. Double stranded RNA comprising non-natural or bases or having a chemically modified backbone may provide additional advantages regarding the increase or decrease of the stability of the dsRNA construct.

Pesticide Compositions

The invention relates, in a still further aspect to a pesticide composition comprising an RNA construct of the invention and/or a DNA construct of the invention and/or expression construct of the invention and/or host cell of the invention together with a suitable carrier, excipient or diluent.

According to a most preferred embodiment, the composition is in a form suitable for ingestion by an insect and/or arachnid.

The composition may be in any suitable physical form for application to insects and/or arachnids. The composition may be in solid form (such as a powder, pellet or a bait), liquid form (such as a spray) or gel form for example.

The composition may contain further components which serve to stabilise the dsRNA and/or prevent degradation of the dsRNA during prolonged storage of the composition.

The composition may still further contain components which enhance or promote uptake of the dsRNA by the intestinal or gut cell. These may include, for example, chemical agents which generally promote the uptake of RNA into cells e.g. lipofectamine etc.

It is contemplated that the "composition" of the invention may be supplied as a "kit-of-parts" comprising the double-stranded RNA in one container and a suitable diluent or carrier for the RNA containing entity (such as an RNA construct, DNA construct, expression construct or host cell) in a separate container. The invention also relates to supply of the double-stranded RNA alone without any further components. In these embodiments the dsRNA may be supplied in a concentrated form, such as a concentrated aqueous solution. It may even be supplied in frozen form or in freeze-dried or lyophilised form. The latter may be more stable for long term storage and may be de-frosted and/or reconstituted with a suitable diluent immediately prior to use.

In one specific embodiment, the composition may be a coating, paste or powder that can be applied to a substrate in order to protect said substrate from infestation by insects and/or arachnids. In this embodiment, the composition can be used to protect any substrate or material that is susceptible to infestation by or damage caused by an insect and/or arachnid, for example foodstuffs and other perishable materials, and substrates such as wood. Preferred target insect and/or arachnid species for this embodiment include, but are not limited to the pests of the invention as defined earlier (see "Target organisms/species"), i.e. household insects and/or arachnids, ectoparasites and insects relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. Most preferred target species are cockroaches, for example cockroaches of the genus *Blatella*, including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). The most preferred target is German cockroach (*Blatella germanica*).

In this embodiment the composition will comprise at least one double-stranded RNA containing entity (e.g. an RNA construct as described above), wherein the double-stranded RNA region comprises annealed complementary strands, at least one of which has a nucleotide sequence which corresponds to a target nucleotide sequence of a target gene from an insect and/or arachnid to be controlled and at least one carrier, diluent or excipient suitable for the intended use.

The nature of the excipients and the physical form of the composition may vary depending upon the nature of the substrate that it is desired to treat. For example, the composition may be a liquid that is brushed or sprayed onto or imprinted into the material or substrate to be treated, or a coating or powder that is applied to the material or substrate to be treated. Thus, in one embodiment, the composition is in the form of a coating on a suitable surface which adheres to, and is eventually ingested by an insect and/or arachnid which comes into contact with the coating.

In one embodiment, the composition is in the form of a bait. The bait is designed to lure the insect and/or arachnid to come into contact with the composition. Upon coming into contact therewith, the composition is then internalised by the insect and/or arachnid, by ingestion for example and mediates RNAi to thus kill the insect and/or arachnid. Said bait may comprise a food substance, such as a protein based food, for example fish meal. Boric acid may also be used as a bait. The bait may depend on the species being targeted. For example, *Blatella germanica* will eat almost any food substance available to them. An attractant may also be used. The attractant may be a pheromone, such as a male or female pheremone for example. As an example, the pheromones referred to in the book "Insect Pheremones and their use in Pest Management" (Howse et al, Chapman and Hall, 1998) may be used in the invention. The attractant acts to lure the insect and/or arachnid to the bait, and may be targeted for a particular insect and/or arachnid or may attract a whole range of insects. The bait may be in any suitable form, such as a solid, paste, pellet or powdered form.

The bait may also be carried away by the insect and/or arachnid back to the colony. The bait may then act as a food source for other members of the colony, thus providing an effective control of a large number of insects and/or arachnids and potentially an entire insect and/or arachnid pest colony. This is an advantage associated with use of the double stranded RNA of the invention, because the delayed action of the RNAi mediated effects on the pests allows the bait to be carried back to the colony, thus delivering maximal impact in terms of exposure to the insects and/or arachnids.

Additionally, compositions which come into contact with the insects and/or arachnids may remain on the cuticle of the insect and/or arachnid. When cleaning, either an individual insect and/or arachnid cleaning itself or insects and/or arachnids cleaning one another, the compositions may be ingested and can thus mediate their effects in the insect and/or arachnid. This requires that the composition is sufficiently stable such that the dsRNA remains intact and capable of mediating RNAi even when exposed to external environmental conditions for a length of time, which may be a period of days for example.

The baits may be provided in a suitable "housing" or "trap". Such housings and traps are commercially available and existing traps may be adapted to include the compositions of the invention. Any housing or trap which may attract an insect and/or arachnid to enter it is included within the scope of the invention. The housing or trap may be box-shaped for example, and may be provided in pre-formed condition or may be formed of foldable cardboard for example. Suitable materials for a housing or trap include plastics and cardboard, particularly corrugated cardboard. Suitable dimensions for such a housing or trap are, for example, 7-15 cm wide, 15-20 cm long and 1-5 cm high. The inside surfaces of the traps may be lined with a sticky substance in order to restrict movement of the insect and/or arachnid once inside the trap. The housing or trap may contain a suitable trough inside which can hold the bait in place. A trap is distinguished from a housing because the insect can not readily leave a trap following entry, whereas a housing acts as a "feeding station" which provides the insect and/or arachnid with a preferred environment in which they can feed and feel safe from predators.

Accordingly, in a further aspect the invention provides a housing or trap for insects and/or arachnids which contains a composition of the invention, which may incorporate any of the features of the composition described herein.

In a further alternative embodiment, the composition may be provided in the form of a spray. Thus, a human user can spray the pest directly with the composition. The composition is then internalized by the insect and/or arachnid, from where it can mediate RNA interference, thus controlling the insect and/or arachnid. The spray is preferably a pressurized/aerosolized spray or a pump spray. The particles may be of suitable size such that they adhere to the insect and/or arachnid, for example to the exoskeleton, of the insect and/or arachnid and may be absorbed therefrom. Particle size may be measured by known means, such as by use of a Mastersizer, which is a commercially available device.

In a still further embodiment, the carrier is an electrostatically charged powder or particle which adheres to the insect and/or arachnid cuticle. Suitable powders and particles which are capable of adhering to an insect and/or arachnid and thus delivering the RNA constructs of the invention are described in detail in WO 94/00980 and WO 97/33472, both of which are incorporated herein by reference.

Alternatively, the carrier may comprise magnetic particles which adhere to the insect cuticle. Suitable magnetic particles which are capable of adhering to an insect and/or arachnid and thus delivering the RNA constructs of the invention are described in detail in WO 00/01236, which reference is incorporated herein.

In a still further embodiment, which is preferred, the carrier of the composition comprises metallic particles which are initially unmagnetised but which are capable of becoming magnetically polarised when subjected to the electrical field provided by the insect and/or arachnid body. This mode of action is described in detail in WO 2004/049807 and is incorporated by reference herein.

These compositions which come into contact with the insects and/or arachnids may remain on the cuticle of the insect and/or arachnid. When cleaning, either an individual insect and/or arachnid cleaning itself or insects and/or arachnids cleaning one another, the compositions may be ingested and can thus mediate their effects in the insect and/or arachnid. This requires that the composition is sufficiently stable such that the dsRNA remains intact and capable of mediating RNAi even when exposed to external environmental conditions for a length of time, which may be a period of days for example.

Preferably, the composition incorporates a carrier which increases the uptake of the double stranded RNA into the insect and/or arachnid pest (see "target organisms/species" above), which is preferably an insect and/or arachnid and preferably a species of cockroach. Such a carrier may be a lipid-based carrier, preferably comprising one or more of, oil-in water emulsions, micelles, cholesterol, lipopolyamines and liposomes. Other agents which promote uptake of the constructs of the invention are well known to those of skill in the art and include polycations, dextrans and (tris) cationic lipids, such as CS096, CS102 etc. Commercially available liposomes include LIPOFECTIN® and CELLFECTIN® etc. A number of suitable carriers are listed under the heading "Transfection promoting agent" in WO 03/004644 and each of the examples provided is hereby incorporated by reference.

In a further preferred embodiment, the carrier is a nucleic acid condensing agent. Preferably, the nucleic acid condensing agent comprises spermidine or protamine sulphate or a derivative thereof.

The compositions of the invention may be combined together with further active ingredients, including with a further pesticide. Thus, the composition may be provided as a "kit-of-parts" comprising the double-stranded RNA containing composition in one container and one or more suitable pesticides, which may be a chemical or biological pesticide, in a separate container. Alternatively, the compositions may be provided as a mixture which are stable and to be used in conjunction with one another.

Suitable active ingredients which may act in a complementary manner to the double stranded RNA molecules of the present invention include, but are not limited to the following: Chlorpyrifos, Allethrin, Resmethrin, Tetrabromoethyl, Dimethol-cyclopropane carboxylic acid (which are generally included in liquid compostions); and Hydramethylnon, Avermectin, Chlorpyrifos, Sulfuramid, Hydroprene, Fipronil (GABA receptor), Isopropylphenyl methyl carbamate, lndoxacarb (PARA), Noviflumuron (Chitinsynthesis inhibitor), Imiprothrin (PARA), Abamectin (Glutamate-gated Chloride channel), Imidacloprid (Acethylcholin receptor) (which are generally included in bait compositions).

In a preferred embodiment, the active ingredient is known to be a preferred insecticide and/or arachnicide in terms of health and environmental considerations, such as for instance Hydramethylnon and Avermectin.

According to another embodiment, the dsRNA is expressed in a suitable host cell such as a bacterial or fungal cell and the cell is taken up or eaten by the pest species. According to a further embodiment, the dsRNA is isolated from, or purified from, the cell which is preferably bacterial or fungal cell expressing the dsRNA, and the dsRNA is provided as a pesticide or in a pesticidal formulation to the pest species. Host cells, such as bacterial and fungal host cells may be engineered to produce any of the dsRNA or RNA constructs of the invention. These host cells, which are preferably bacterial cells may be ingested or otherwise internalized by the pest species. When taken up, the dsRNA can initiate an RNAi response, leading to the degradation of the target mRNA and weakening or killing of the pest.

Therefore, in a more specific embodiment, said double-stranded RNA or RNA construct is expressed by a prokaryotic, such as a bacterial, or eukaryotic, such as a yeast, host cell or host organism. These cells or organisms may be provided in any suitable formulation to facilitate uptake by the insect and/or arachnid.

Uses and Methods of the Invention

In a still further aspect, the invention relates to the use of an RNA construct of the invention and/or a DNA construct of the invention and/or an expression construct of the invention and/or a composition of the invention and/or housing or trap of the invention for controlling an insect and/or arachnid by RNA interference. The use may apply to a number of insects and/or arachnids at all stages of development, having orthologous target genes to the novel targets identified herein, including household insects and/or arachnids, ecto-parasites and insects and/or arachnids relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. Most preferred target species are cockroaches, for example cockroaches of the genus *Blatella*, including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). The most preferred target is German cockroach (*Blatella germanica*).

Preferably, the pest is combatted via RNAi, and is consequently killed, paralysed, delayed in growth, inhibited in feeding of and/or hindered in its reproduction.

In a complementary aspect, the invention also provides a method of controlling insect and/or arachnid (pests) comprising administering to an insect and/or arachnid an RNA construct comprising a dsRNA region as defined above and/or a DNA construct of the invention and/or an expression construct as defined above and/or host cells as defined above and/or a composition as defined above and/or housing or trap as defined above, wherein the double stranded RNA is capable of down regulating the expression of at least one insect gene through RNA interference.

The administration may involve, for example feeding the insect and/or arachnid or may involve contacting the insect and/or arachnid with the dsRNA (in its various forms of presentation as described and defined above). Suitable means for direct contact include baits sticky strips, magnetic and electrically charged powders and particles sprays, gels, ointments, surface treatments etc as defined and described above with respect to the compositions of the invention. Any means of administration is included within the scope of the present invention provided it leads to effective double stranded RNA mediated interference of target gene expression, thus controlling the insect and/or arachnid.

It may be advantageous to provide multiple double stranded RNA region containing constructs directed against multiple targets, since this increases the efficacy of the insect and/or arachnid control and also decreases the possibility of the insect and/or arachnid acquiring resistance.

Accordingly, in one embodiment of the method, multiple RNA constructs as defined above and/or DNA constructs as defined above and/or expression constructs as defined above and/or host cells as defined above and/or compositions as defined above and/or housing or trap as defined above are provided/administered to the pest in order to mediate multiple separate RNAi events.

The multiple targets may all be targeted at the same time, or may be targeted in sequential manner. Thus, in one embodiment, the multiple RNA constructs and/or DNA constructs and/or expression constructs and/or host cells and/or compositions and/or housings or traps are provided/administered sequentially in order to reduce the probability of the insect and/or arachnid acquiring resistance.

The methods of the invention may apply to a number of insects and/or arachnids at all stages of development, having orthologous target genes to the novel targets identified herein. Target insects include household insects and/or arachnids, ecto-parasites and insects and/or arachnids relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. Most preferred target species are cockroaches, for example cockroaches of the genus *Blatella*, including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). The most preferred target is German cockroach (*Blatella germanica*).

Preferably, the insect and/or arachnid pest is combatted via RNAi, and is consequently killed, paralysed, delayed in growth, inhibited in feeding of and/or hindered in its reproduction.

The host cell may be, in one embodiment, a bacterial cell which has been engineered to produce the RNA constructs of the invention.

In a still further aspect, the invention provides a method for controlling cockroach pests comprising providing/administering to the cockroach an RNA construct comprising at least one double stranded RNA region, at least one strand of which comprises a nucleotide sequence that is complementary to a portion of the nucleotide sequence encoding a cockroach ribosomal protein. Cockroach ribosomal proteins represent a novel target for RNAi, which can mediate effective control of a cockroach infestation.

Preferably, at least one strand of the at least one double stranded RNA region comprises at least about 17, 18, 19, 20, 21 nucleotides, preferably at least about 23 nucleotides, 24 nucleotides, 27 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 900 nucleotides, 1000 nucleotides, 1100 nucleotides, 1200 nucleotides or about 1300 nucleotides of any of the nucleic acid molecules comprising the nucleotide sequence as set forth in any of SEQ ID NOs 1, 4, 6, 7, 9, 10, 65 to 70, 71 to 79, 11, 16, 17, 19, 20, 80 to 87, 21, 26, 27, 29, 30, 88 to 93, 31, 36, 37, 39, 40, 94 to 108, 180 and 181, or the complement thereof.

In an even further aspect, the invention provides a method for controlling cockroach pests comprising providing/administering to the cockroach an RNA construct comprising at least one double stranded RNA region, at least one strand of which comprises a nucleotide sequence that is complementary to a portion of the nucleotide sequence encoding a tropomyosin, a HMG Coenzyme A synthase gene or an Actin 5C gene. Cockroach tropomyosin, HMG Coenzyme A synthase and Actin 5C proteins represent a novel target for RNAi, which can mediate effective control of a cockroach infestation.

Preferably, at least one strand of the at least one double stranded region comprises at least about 17 nucleotides, preferably at least about 18 nucleotides, 19 nucleotides, 20 nucleotides, 21 nucleotides, 23 nucleotides, 24 nucleotides, 27 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 900 nucleotides, 1000 nucleotides, 1100 nucleotides, 1200 nucleotides or about 1300 nucleotides of any of the nucleic acid molecules comprising the nucleotide sequence as set forth in any of SEQ ID NOs 41, 43, 44, 47, 48, 109 to 147, 182 to 187, 49, 51, 52, 55, 56, 148 to 150, 57, 63, 64, 151 to 179, and 188 to 200, or the complement thereof.

The methods of the invention may apply to a number of insects and/or arachnids at all stages of development, having orthologous target genes to the novel targets identified herein. Target insects include household insects, ecto-parasites and insects and/or arachnid relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas. More preferred target species are cockroaches (Blattodea) such as but not, limited to *Blatella* spp. (e.g. *Blatella germanica* (german cockroach)), *Periplaneta* spp. (e.g. *Periplaneta americana* (American cockroach) and *Periplaneta australiasiae* (Australian cockroach)), *Blatta* spp. (e.g. *Blatta orientalis* (Oriental cockroach)) and *Supella* spp. (e.g. *Supella longipalpa* (brown-banded cockroach); ants (Formicoidea), such as but not limited to *Solenopsis* spp. (e.g. *Solenopsis invicta* (Red Fire Ant)), *Monomorium* spp. (e.g. *Monomorium pharaonis* (Pharaoh Ant)), *Camponotus* spp. (e.g. *Camponotus* spp (Carpenter Ants)), *Lasius* spp. (e.g. *Lasius niger* (Small Black Ant)), *Tetramorium* spp. (e.g. *Tetramorium caespitum* (Pavement Ant)), *Myrmica* spp. (e.g. *Myrmica rubra* (Red Ant)), *Formica* spp (wood ants), *Crematogaster* spp. (e.g. *Crematogaster lineolata* (Acrobat Ant)), *Iridomyrmex* spp. (e.g. *Iridomyrmex humilis* (Argentine Ant)), *Pheidole* spp. (Big Headed Ants), and *Dasymutilla* spp. (e.g. *Dasymutilla occidentalis* (Velvet Ant)); termites (Isoptera and/or Termitidae) such as but not limite to *Amitermes* spp. (e.g. *Amitermes floridensis* (Florida dark-winged subterranean termite)), *Reticulitermes* spp. (e.g. *Reticulitermes flavipes* (the eastern subterranean termite), *Reticulitermes hesperus* (Western Subterranean Termite)), *Coptotermes* spp. (e.g. *Coptotermes formosanus* (Formosan Subterranean Termite)), *Incisitermes* spp. (e.g. *Incisitermes minor* (Western Drywood Termite)) and *Neotermes* spp. (e.g. *Neotermes connexus* (Forest Tree Termite)), cockroaches, for example cockroaches of the genus *Blatella*, including German cockroach (*Blatella germanica*), of the genus *Periplaneta*, including American cockroach (*Periplaneta americana*) and Australian cockroach (*Periplaneta australiasiae*), of the genus *Blatta*, including Oriental cockroach (*Blatta orientalis*) and of the genus *Supella*, including brown-banded cockroach (*Supella longipalpa*). More preferred targets are cockroaches. The most preferred target is German cockroach (*Blatella germanica*).

Preferably, the insect and/or arachnid pest is combatted via RNAi, and is consequently killed, paralysed, delayed in growth, inhibited in feeding of and/or hindered in its reproduction.

Kits of the Invention

The invention also provides kits for use in the methods of the invention. These kits may incorporate the RNA constructs and/or DNA constructs and/or expression constructs and/or host cells and/or compositions and/or housings or traps of the invention, all of which deliver dsRNA regions to effect RNAi against specific target genes.

Preferably, the kits will also include instructions for use of the components of the kit. The double stranded RNAs found in the kits of the invention, or produced by components of the kits of the invention are capable of down regulating the expression of at least one insect (pest) gene through RNA interference.

Preferably, in order to provide more effective pest control (as described above), the kit comprises multiple components, each of which mediates RNAi at a different target gene or insect and/or arachnid species. Thus the kit may comprise multiple RNA constructs and/or DNA constructs and/or expression constructs and/or compositions, wherein each double stranded RNA is capable of down regulating the expression of at least one insect and/or arachnid (pest) gene through RNA interference.

Preferably, the components of the kit are applied sequentially to mediate effective pest control. However, some or all of the components may be administered simultaneously if required for maximal impact.

The kit may additionally comprise known pesticides, which may be provided together or separately from the components forming part of the invention.

Suitable active ingredients which may act in a complementary manner to the double stranded RNA molecules of the present invention include, but are not limited to the following: Chlorpyrifos, Allethrin, Resmethrin, Tetrabromoethyl, Dimethol-cyclopropane carboxylic acid (which are generally included in liquid compostions), and Hydramethylnon, Avermectin, Chlorpyrifos, Sulfuramid, Hydroprene, Fipronil (GABA receptor), Isopropylphenyl methyl carbamate, Indoxacarb (PARA), Noviflumuron (Chitinsynthesis inhibitor), Imiprothrin (PARA), Abamectin (Glutamate-gated Chloride channel), Imidacloprid (Acethylcholin receptor) (which are generally included in bait compositions).

In a preferred embodiment, the active ingredient is known to be a "preferred" insecticide and/or arachnicide with respect to health and environmental considerations, such as for instance Hydramethylnon and avermectin.

The kits of the invention may thus also be directed against multiple species at the same time in order to give a broad-scale pest control option. Double stranded RNA molecules may be included in the kits (as part of the appropriate constructs etc.) to mediate RNAi of multiple targets, including inter-species orthologues of the same targets for example.

The kits may include suitable buffers and packaging etc to ensure stability and storage of the components therein.

Technical Advantages of the Invention

There are numerous major advantages associated with the present invention over the use of conventional chemical insecticides.

(1) The RNAi mediating dsRNA has to match the target with a high degree of nucleotide sequence identity in order to effectively down regulate expression and thus control the pest. Thus, specificity can be achieved by designing double stranded RNA molecules in which one strand has high homology to the target sequence but which strand has only low homology to the orthologous sequence in a mammalian species, such as a human. This specificity is greater than can be achieved with conventional chemical pesticides.

(2) A new set of targets has been identified which can be used in the control of pests. Because these targets have previously not been identified, there should be no acquired resistance in the pest species.

(3) The double stranded RNA used in RNAi against the novel targets is a biodegradable product as compared to the known chemically synthesised pesticides, such as DMSO etc. The biodegradable nature of the constructs makes them more environmentally sound.

(4) RNAi does not necessarily provide an immediate effect in terms of killing the pest, rather the effects are mediated effectively but require time for the double stranded RNA to be associated with its target. The RNAi effect may result in killing the pest at a later moment and not directly upon contact, such as Noviflumuron (which is a chitinsynthesis inhibiter, from Dow AgroSciences). Thus, the use of RNAi may allow more facile control of large infestations of pests such as insects and/or arachnids because there is less chance of a shock effect being propagated amongst the pests where they may encounter a large number of dead pests in the vicinity of the insecticide and/or arachnicide.

(5) The use of multiple targets at the same time may provide more efficacious control of pest populations and reduce the possibility of acquired resistance. The targets may be common to a number of pest species providing broad scale treatment.

(6) In contrast to conventional pesticides, no professional assistance would be required in order to treat the relevant areas, due to the more safe nature of the DNA and RNA constructs, compositions and host cells of the invention.

(7) Minimum disruption of human activity would be required since the double stranded RNA region containing constructs are designed such that they will have no adverse effects or only minor effects on gene expression outside of the target pest population.

The invention will be further understood with reference to the following experimental section:

DESCRIPTION OF TABLES AND FIGURES

Table 1: Examples of novel identified insect target genes. Gene function assigned is based on the FlyBase orthologue.

Table 2: dsRNA fragments complementary to *Blatella germanica* target sequences

Table 3: Effect of dsRNA treatments on the number of cockroaches successfully moulting to the adult stage, as a percentage of live insects (means±standard errors, n=4)

Table 4: Selected sequences* of target genes. Fragments of at least 17 bp of the sequences* are present in the specified orthologous sequences in insect species (represented by GI number).

Table 5: Selected sequences* of target genes. Fragments of at least 17 bp of the sequences* are present in the specified orthologous sequences in arachnid species (represented by GI number).

FIG. 1: Mortality of *B. germanica* on artificial pellet diet. The concentration of dsRNA in the pellets was 1% w/w. The concentration of imidacloprid was 1% w/w.

Figure 2:
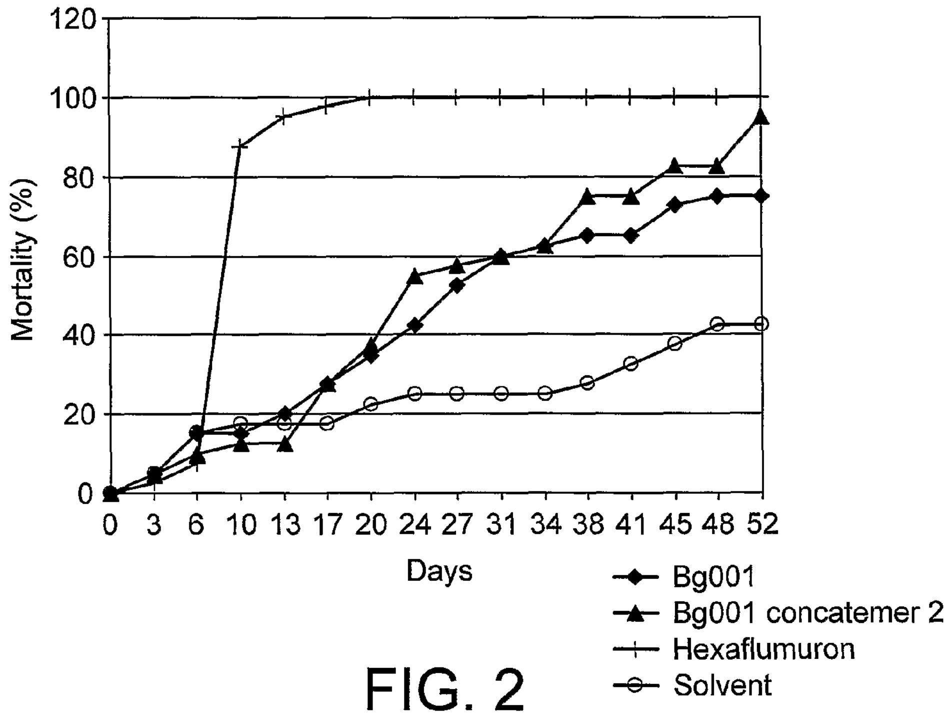

FIG. 2: Mortality of *B. germanica* on artificial pellet diet. The concentration of dsRNA (Bg001, having the sequence as represented as SEQ ID NO 9, and Bg001 concatemer 2, having the sequence as represented as SEQ ID NO 68) in the pellets was 1% w/w. In this experiment, hexaflumuron (1% w/w) was tested as a positive control and solvent as a negative control.

Figure 3:
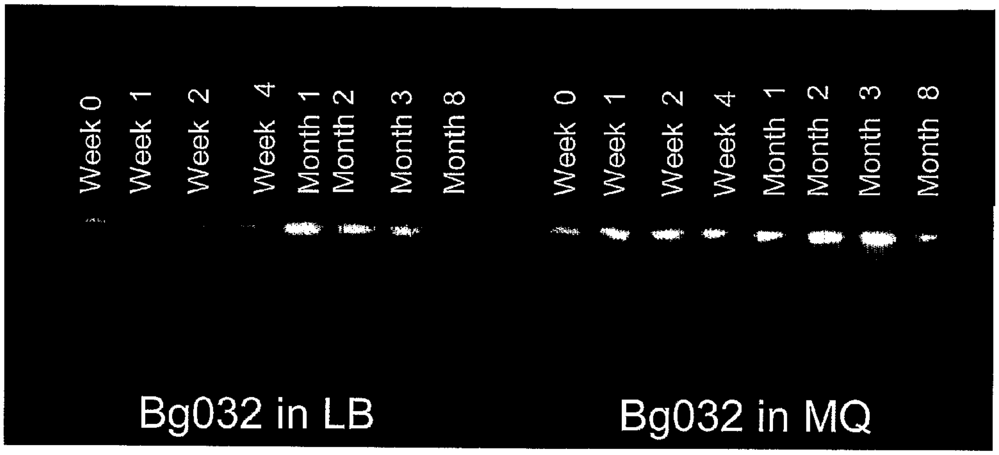
Figure 4:
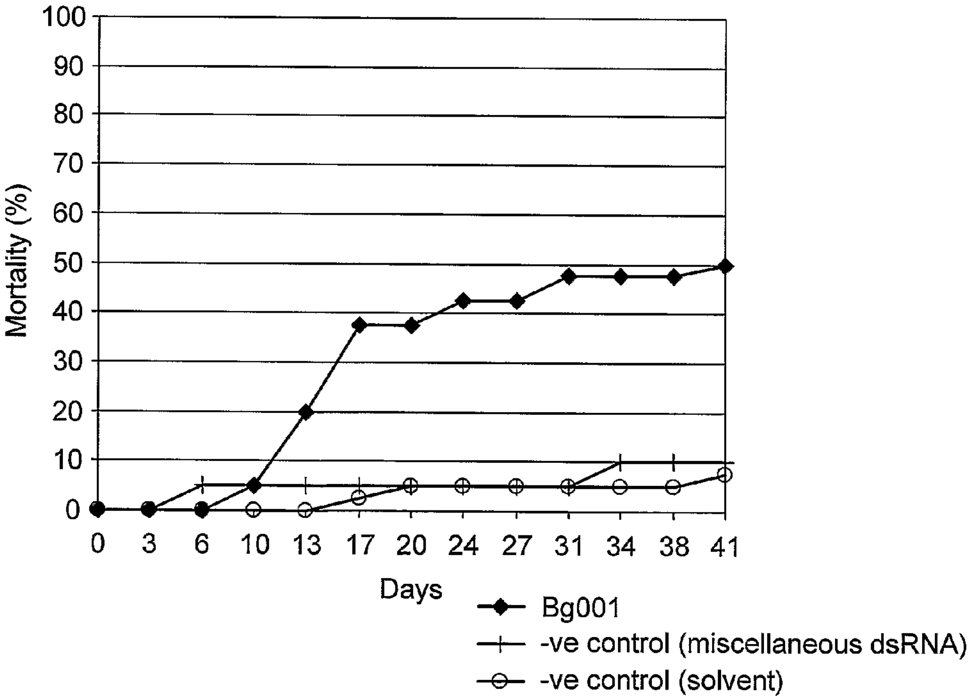

FIG. 3 Stability of Bg032 dsRNA in LB medium (LB) and Rnase free water (MQ) at room temperature over a period of eight months FIG. 4: Effect on cockroach mortality upon applying dsRNA (Bg001) to first instars nymphs during one week. In this experiment, miscellaneous dsRNA and solvent were tested as negative controls. The concentration of dsRNA in the pellets was 1% w/w.

FIG. 5: Sequences of the invention

TABLE 1

| Target ID | Dm identifier | SEQ ID NO NA | SEQ ID NO AA | Function (based on FlyBase): flybase.org/ |
|---|---|---|---|---|
| Bg001 | CG11276 | 1 | 2 | Ribosomal protein S4 (RpS4), structural constituent of ribosome involved in protein biosynthesis which is a component of the cytosolic small ribosomal subunit |
| Bg003 | CG3395 | 11 | 12 | Ribosomal protein S9 (RpS9), structural constituent of ribosome involved in protein biosynthesis which is a component of the cytosolic small ribosomal subunit |
| Bg004 | CG6141 | 21 | 23 | Ribosomal protein L9, structural constituent of ribosome involved in protein biosynthesis which is localised to the ribosome |
| Bg005 | CG2746 | 31 | 32 | Ribosomal protein L19, structural constituent of ribosome involved in protein biosynthesis which is localised to the ribosome |
| Bg031 | CG4898 | 41 | 42 | Tropomyosin 1 (AF260897), member of the tropomyosins family which are closely related proteins with multiple functions, including the regulation of the actin-myosin interaction, transport of mRNA, and mechanical support of the cytoplasmic membrane) |
| Bg032 | CG16796 | 49 | 50 | HMG Coenzyme A synthase (X73679) catalyzes a committed step in the pathways for isoprenoid, cholesterol, and ketone body production |
| Bg033 | CG4027 | 57 | 58 | Actin 5C (AY004248) is the major gene in *Drosophila melanogaster* that encodes the cytoskeletal actin present in all cell types in all growth stages |

TABLE 2

| Gene | dsRNA fragment size (bp) | freefrag | freefrag size (position on dsRNA) |
|---|---|---|---|
| Bg001 | 594 (SEQ ID NO 9) | best1_human_24_3 | 69 (19-87) |
| Bg001 | 594 (SEQ ID NO 9) | best2_human_24_3 | 69 (445-513) |
| Bg001 | 594 (SEQ ID NO 9) | best3_human_24_3 | 62 (206-267) |
| Bg001 | 594 (SEQ ID NO 9) | best1_human_21_0 | 573 (1-573) |
| Bg003 | 433 (SEQ ID NO 19) | best1_human_24_3 | 133 (141-273) |
| Bg003 | 433 (SEQ ID NO 19) | best2_human_24_3 | 72 (68-139) |
| Bg003 | 433 (SEQ ID NO 19) | best3_human_24_3 | 65 (1-65) |
| Bg003 | 433 (SEQ ID NO 19) | best1_human_21_0 | 412 (1-412) |
| Bg004 | 449 (SEQ ID NO 29) | best1_human_24_3 | 78 (276-353) |
| Bg004 | 449 (SEQ ID NO 29) | best2_human_24_3 | 61 (200-260) |
| Bg004 | 449 (SEQ ID NO 29) | best3_human_24_3 | 53 (91-143) |
| Bg004 | 449 (SEQ ID NO 29) | best1_human_21_0 | 428 (1-428) |
| Bg005 | 404 (SEQ ID NO 39) | best1_human_24_3 | 115 (40-154) |
| Bg005 | 404 (SEQ ID NO 39) | best2_human_24_3 | 45 (191-235) |
| Bg005 | 404 (SEQ ID NO 39) | best3_human_24_3 | 42 (237-278) |
| Bg005 | 404 (SEQ ID NO 39) | best1_human_21_0 | 383 (1-383) |
| Bg031 | 849 (SEQ ID NO 47) | best1_human_24_3 | 70 (756-825) |
| Bg031 | 849 (SEQ ID NO 47) | best2_human_24_3 | 56 (546-601) |
| Bg031 | 849 (SEQ ID NO 47) | best3_human_24_3 | 54 (280-333) |
| Bg031 | 849 (SEQ ID NO 47) | best1_human_21_0 | 821 (8-828) |
| Bg031 | 849 (SEQ ID NO 47) | best2_human_21_0 | 6 (1-6) |
| Bg032 | 1300 (SEQ ID NO 55) | best1_human_24_3 | 126 (1138-1263) |
| Bg032 | 1300 (SEQ ID NO 55) | best2_human_24_3 | 114 (731-844) |
| Bg032 | 1300 (SEQ ID NO 55) | best3_human_24_3 | 99 (259-357) |
| Bg032 | 1300 (SEQ ID NO 55) | best1_human_21_0 | 1279 (1-1279) |
| Bg033 | 446 (SEQ ID NO 63) | best1_human_24_3 | 4 (362-365) |
| Bg033 | 446 (SEQ ID NO 63) | best2_human_24_3 | 4 (367-370) |
| Bg033 | 446 (SEQ ID NO 63) | best3_human_24_3 | 3 (115-117) |
| Bg033 | 446 (SEQ ID NO 63) | best1_human_21_0 | 108 (88-195) |
| Bg033 | 446 (SEQ ID NO 63) | best2_human_21_0 | 102 (244-345) |
| Bg033 | 446 (SEQ ID NO 63) | best3_human_21_0 | 62 (350-411) |

TABLE 3

| Day | Bg001 | Bg001 concatemer 2 | Positive control | Negative control |
|---|---|---|---|---|
| 38 | 0.0 (±0.0) | 0.0 (±0.0) | 0.0 (±0.0) | 2.5 (±2.5) |
| 41 | 0.0 (±0.0) | 0.0 (±0.0) | 0.0 (±0.0) | 9.6 (±6.7) |
| 45 | 0.0 (±0.0) | 0.0 (±0.0) | 0.0 (±0.0) | 64.1 (±14.0) |

TABLE 3-continued

| Day | Bg001 | Bg001 concatemer 2 | Positive control | Negative control |
|---|---|---|---|---|
| 48 | 33.3 (±23.6) | 0.0 (±0.0) | 0.0 (±0.0) | 77.1 (±10.4) |
| 52 | 41.7 (±25.0) | 0.0 (±0.0) | 0.0 (±0.0) | 100.0 (±0.0) |

TABLE 4

| Target ID | SEQ ID NO | Example GI-number and species | Sequence* |
|---|---|---|---|
| Bg001 | 71 | 2871551 (*Drosophila melanogaster*) | aaggcatggatgttggacaagct |
| Bg001 | 72 | 48927129 (*Hydropsyche* sp.) | gcatggatgttggacaagctcgg |
| Bg001 | 73 | 60293875 (*Homalodisca coagulata*); 71547743 (*Oncometopia nigricans*) | attaaggttgatggaaaagtcagaac |
| Bg001 | 74 | 56153292 (*Rhynchosciara americana*) | cccaactatccagctggttttatggatgttgt |
| Bg001 | 75 | 90820001 (*Graphocephala atropunctata*) | gctggttttatggatgttgttacaattgaaaa |
| Bg001 | 76 | 25956479 (*Biphyllus lunatus*) | attgaaaaaactggagaatttttccg |
| Bg001 | 77 | 15353483 (*Apis mellifera*) | ggtaatctctgtatgattactgg |
| Bg001 | 78 | 92041090 (*Drosophila willistoni*) | cgtcatcctggttcctttgacattgt |
| Bg001 | 79 | 62083410 (*Lysiphlebus testaceipes*) | ttaaagattcacaaggacacac |
| Bg003 | 80 | 76169686 (*Diploptera punctata*) | aaaatccgtaaagctgccagagaact |
| Bg003 | 81 | 62083482 (*Lysiphlebus testaceipes*) | cgtaaagctgccagagaacttct |
| Bg003 | 82 | 2459311 (*Antheraea yamamai*) | aggttgtttgaaggcaatgctctt |
| Bg003 | 83 | 22040140 (*Ctenocephalides felis*) | cgtattggagtgttggatgaa |

TABLE 4-continued

| Target ID | SEQ ID NO | Example GI-number and species | Sequence* |
|---|---|---|---|
| Bg003 | 84 | 83664146 (*Myzus persicae*) | ccgtatgaagcttgattacgt |
| Bg003 | 85 | 55909980 (*Locusta migratoria*);<br>76169686 (*Diploptera punctata*);<br>15358510 (*Apis mellifera*);<br>67890783 (*Drosophila pseudoobscura*) | ttgggtttgaagattgaagatttcttgga |
| Bg003 | 86 | 62240069 (*Diabrotica virgifera*) | aagattgaagatttcttggaa |
| Bg003 | 87 | 57963755 (*Heliconius melpomene*);<br>83663084 (*Myzus persicae*) | aggaacaaacgtgaagtgtggcg |
| Bg004 | 88 | 70909652 (*Cicindela litorea*) | tgctctcatattgagaacatg |
| Bg004 | 89 | 83660638 (*Myzus persicae*) | aagggtttcctgtacaaaatg |
| Bg004 | 90 | 83931139 (*Lutzomyia longipalpis*) | gccgtgtatgcccatttccccat |
| Bg004 | 91 | 67895088 (*Drosophila pseudoobscura*);<br>92218607 (*Drosophila willistoni*) | tatgcccatttccccattaactgcgt |
| Bg004 | 92 | 92960248 (*Drosophila ananassae*);<br>15455304 (*Drosophila melanogaster*);<br>38047668 (*Drosophila yakuba*) | cgtaacttcttgggcgagaagt |
| Bg004 | 93 | 56199511 (*Culicoides sonorensis*);<br>67876239 (*Drosophila pseudoobsoura*) | aaatggtttggaacaaagaaggag |
| Bg005 | 94 | 92931824 (*Drosophila virilis*) | gatcccaatgaaataaacgaaat |
| Bg005 | 95 | 55883492 (*Locusta migratoria*) | aatgaaataaacgaaattgcaaatac |
| Bg005 | 96 | 60296437 (*Homalodisca coagulata*) | ggttttggcaaaaggaagggtac |
| Bg005 | 97 | 78231035 (*Heliconius erato/himera* mixed EST library) | gcaaatgcccgtatgccacagaa |
| Bg005 | 98 | 76553206 (*Spodoptera frugiperda*);<br>33491424 (*Trichoplusia ni*) | aatgcccgtatgccacagaagg |
| Bg005 | 99 | 55900360 (*Locusta migratoria*) | aagaagtacagggaagcaaagaa |
| Bg005 | 100 | 57963592 (*Heliconius melpomene*) | aagaagatcgacagacatctata |
| Bg005 | 101 | 92948400 (*Drosophila ananassae*);<br>2871894 (*Drosophila melanogaster*);<br>68267374 (*Drosophila simulans*);<br>33354497 (*Drosophila yakuba*);<br>83935652 (*Lutzomyia longipalpis*);<br>18866169 (*Anopheles gambiae*);<br>60307025 (*Sphaerius* sp.);<br>25958948 (*Curculio glandium*);<br>90812513 (*Nasonia giraulti*) | caagggtaacgtgttcaagaacaagcg |
| Bg005 | 102 | 18909153 (*Anopheles gambiae*);<br>60311920 (*Euclidia glyphica*);<br>25957531 (*Cicindela campestris*);<br>18948649 (*Anopheles gambiae*);<br>38048300 (*Drosophila yakuba*);<br>58385089 (*Anopheles gambiae* str. PEST);<br>27556513 (*Anopheles gambiae*);<br>70909752 (*Cicindela campestris*);<br>56462221 (*Lonomia obliqua*);<br>92931824 (*Drosophila virilis*) | aagggtaacgtgttcaagaacaagcgtgtcct |
| Bg005 | 103 | 25957246 (*Carabus granulatus*);<br>90135865 (*Bicyclus anynana*) | gtgttcaagaacaagcgtgtcctgatggagt |
| Bg005 | 104 | 71538996 (*Diaphorina citri*);<br>90812513 (*Nasonia giraulti*);<br>60311920 (*Euclidia glyphica*) | tgatggagttcatccacaagaagaaggctg |
| Bg005 | 105 | 15511486 (*Drosophila melanogaster*) | catccacaagaagaaggctgagaag |
| Bg005 | 106 | 60311920 (*Euclidia glyphica*) | acaagaagaaggctgagaaggc |

TABLE 4-continued

| Target ID | SEQ ID NO | Example GI-number and species | Sequence* |
|---|---|---|---|
| Bg005 | 107 | 82572137 (*Acyrthosiphon pisum*); 73616334 (*Aphis gossypii*); 37804858 (*Rhopalosiphum padi*); 31365253 (*Toxoptera citricida*); 84647391 (*Myzus persicae*) | accaattccagacaaaatattcgtaa |
| Bg005 | 108 | 55908261 (*Locusta migratoria*); 10764114 (*Manduca sexta*); 90135865 (*Bicyclus apynana*); 91845469 (*Bombyx mori*) | gaagaaggctgagaaggccaggaca |
| Bg031 | 109 | 84252313 (*Aedes aegypti*); 78052352 (*Heliconius erato*); 50818693 (*Heliconius melpomene*); 92942003 (*Drosophila ananassae*); 92466045 (*Drosophila erecta*); 92998051 (*Drosophila grimshawi*); 3627588 (*Drosophila melanogaster*); 92985296 (*Drosophila mojavensis*); 92921049 (*Drosophila virilis*); 92230306 (*Drosophila willistoni*); 92983068 (*Drosophila mojavensis*); 60294371 (*Homalodisca coagulata*); 73614014 (*Aphis gossypii*); 90819969 (*Graphocephala atropunctata*); 55886387 (*Locusta migratoria*); 85854848 (*Aedes aegypti*); 19310970 (*Periplaneta fuliginosa*); 20387026 (*Lepisma saccharina*); 27621313 (*Anopheles gambiae*); 91838618 (*Bombyx mori*); 20387028 (*Lepisma saccharina*); 4378572 (*Periplaneta americana*); 71050465 (*Oncometopia nigricans*); 18916954 (*Anopheles gambiae*); 29557544 (*Bombyx mori*); 55911583 (*Locusta migratoria*); 90978993 (*Aedes aegypti*); 56462261 (*Lonomia obliqua*); 85850284 (*Aedes aegypti*); 78230930 (*Heliconius erato/himera* mixed EST library); 55895968 (*Locusta migratoria*); 29557242 (*Bombyx mori*); 18926345 (*Anopheles gambiae*); 37663025 (*Bombyx mori*); 18940590 (*Anopheles gambiae*); 81521031 (*Lutzomyia longipalpis*); 55804534 (*Acyrthosiphon pisum*); 18898107 (*Anopheles gambiae*); 29557268 (*Bombyx mori*); 84647487 (*Myzus persicae*); 37664569 (*Bombyx mori*); 81521022 (*Lutzomyia longipalpis*); 70978108 (*Aedes aegypti*) | atggatgccatcaagaagaagatgcaggcgatgaagctggagaaggacaacgcg |
| Bg031 | 110 | 4378572 (*Periiplaneta americana*); 19310970 (*Periplaneta fuliginosa*) | gggccgagaaggctgaggaggaggc |
| Bg031 | 111 | 4378572 (*Periplaneta americana*); 19310970 (*Periplaneta fuliginosa*) | tccctgcagaagaagatccagcagattgagaatgatct |
| Bg031 | 112 | 50557705 (*Homalodisca coagulata*); 71050465 (*Oncometopia nigricans*) | tgatgcaagtcaacgccaagct |
| Bg031 | 113 | 78056651 (*Heliconius erato*); 50818693 (*Heliconius melpomene*) | atgcaagtcaacgccaagctgga |
| Bg031 | 114 | 4378572 (*Periplaneta americana*); 19310970 (*Periplaneta fuliginosa*) | gtcaacgccaagctggacgagaaggacaaggccct |
| Bg031 | 115 | 71050465 (*Oncometopia nigricans*) | gagaaggacaaggccctgcagaa |
| Bg031 | 116 | 55907164 (*Locusta migratoria*); 55917622 (*Locusta migratonia*) | aaccgccgaatccaactgctggagga |

TABLE 4-continued

| Target ID | SEQ ID NO | Example GI-number and species | Sequence* |
|---|---|---|---|
| Bg031 | 117 | 86462380 (*Acyrthosiphon pisum*); 73618346 (*Aphis gossypii*); 53883526 (*Plutella xylostella*); 25958075 (*Platystomos albinus*); 85854848 (*Aedes aegypti*); 40384866 (*Nilaparvata lugens*); 56085268 (*Bombyx mori*); 78050451 (*Heliconius erato*); 71535946 (*Diaphorina citri*); 20387028 (*Lepisma saccharina*); 4378572 (*Periplaneta americana*); 19310970 (*Periplaneta fuliginosa*); 66500379 (*Apis mellifera*); 45753874 (*Apis mellifera*); 66522385 (*Apis mellifera*) | gcgatgaagctggagaaggacaacgcgatgga tcgcgc |
| Bg031 | 118 | 34788042 (*Callosobruchus maculatus*) | tctgaggaacgtttggccacagc |
| Bg031 | 119 | 20387028 (*Lepisma saccharina*) | tggcagatgaagagcgtatgga |
| Bg031 | 120 | 90972767 (*Aedes aegypti*); 56150925 (*Rhynchosciara americana*); 85854848 (*Aedes aegypti*) | gatgaagagcgtatggatgct |
| Bg031 | 121 | 60296314 (*Homalodisca coagulata*); 71050465 (*Oncometopia nigricans*) | gctttggagaaccagctgaagga |
| Bg031 | 122 | 85850407 (*Aedes aegypti*) | gagaaccagctgaaggaagcc |
| Bg031 | 123 | 29555905 (*Bombyx mori*) | cagctgaaggaagccaggttc |
| Bg031 | 124 | 85847532 (*Aedes aegypti*); 77850398 (*Aedes aegypti*); 3627588 (*Drosophila melanogaster*); 56150925 (*Rhynchosciara americana*); 77792932 (*Aedes aegypti*) | ttcatggctgaggaagctgacaagaaata |
| Bg031 | 125 | 78540242 (*Glossina morsitans*); 6901854 (*Bombyx mori*) | gctgacaagaaatatgatgaggt |
| Bg031 | 126 | 40384866 (*Nilaparvata lugens*) | gacaagaaatatgatgaggtcgc |
| Bg031 | 127 | 84647487 (*Myzus persicae*) | atggttgaggccgacttggaaagagcaga |
| Bg031 | 128 | 51979105 (*Myzus persicae*) | gccgacttggaaagagcagaaga |
| Bg031 | 129 | 55886192 (*Locusta migratoria*) | cgacttggaaagagcagaagagcgtgc |
| Bg031 | 130 | 92957972 (*Drosophila ananassae*) | ccaagattgtggagcttgagga |
| Bg031 | 131 | 60312749 (*Gryllus bimaculatus*) | aagattgtggagcttgaggaaga |
| Bg031 | 132 | 70978108 (*Aedes aegypti*) | tggatcgcgcccttctctgcgaacagcaggcc cg |
| Bg031 | 133 | 67842690 (*Drosophila pseudoobscura*) | attgtggagcttgaggaagaactgcgcgt |
| Bg031 | 134 | 92939324 (*Drosophila virilis*) | ctgcgcgttgtcggcaacaac |
| Bg031 | 135 | 53883608 (*Plutella xylostella*) | cgcgttgtcggcaacaacctgaagtcccttga ggt |
| Bg031 | 136 | 4378572 (*Periplaneta americana*); 19310970 (*Periplaneta fuliginosa*); 33354924 (*Drosophila yakuba*); 25957752 (*Cicindela campestris*); 60312749 (*Gryllus bimaculatus*); 55907164 (*Locusta migratoria*); 75726914 (*Tribolium castaneum*) | gttgtcggcaacaacctgaagtcccttgaggt gtctgaagagaaggccaacctgcgtga |
| Bg031 | 137 | 19310970 (*Periplaneta fuliginosa*) | taccaggctaaaggaggctga |
| Bg031 | 138 | 55923520 (*Locusta migratoria*); 20387028 (*Lepisma saccharina*); 55922834 (*Locusta migratoria*) | accaggctaaaggaggctgaagc |

TABLE 4-continued

| Target ID | SEQ ID NO | Example GI-number and species | Sequence* |
|---|---|---|---|
| Bg031 | 139 | 25958290 (*Platystomos albinus*) | gctaaaggaggctgaagctcg |
| Bg031 | 140 | 45757348 (*Apis mellifera*);<br>77783094 (*Aedes aegypti*);<br>25956952 (*Biphyllus lunatus*);<br>25957752 (*Cicindela campestris*);<br>90972767 (*Aedes aegypti*);<br>75722624 (*Tribolium castaneum*);<br>47519043 (*Acyrthosiphon pisum*);<br>73612504 (*Aphis gossypii*);<br>83664605 (*Myzus persicae*);<br>9055470 (*Pyrocoelia rufa*);<br>30030953 (*Toxoptera citricida*);<br>77758700 (*Aedes aegypti*);<br>33365552 (*Glossina morsitans*);<br>56154884 (*Rhynchosciara americana*);<br>78540242 (*Glossina morsitans*) | ctaaaggaggctgaagctcgtgctgagtt |
| Bg031 | 141 | 52630932 (*Toxoptera citricida*);<br>71047185 (*Oncometopia nigricans*) | aaggaggctgaagctcgtgctgagttcgctga |
| Bg031 | 142 | 92943056 (*Drosophila ananassae*);<br>92460361 (*Drosophila erecta*);<br>49400641 (*Drosophila melanogaster*) | gctcgtgctgagttcgctgaa |
| Bg031 | 143 | 19310970 (*Periplaneta fuliginosa*);<br>60311491 (*Euclidia glyphica*);<br>60312896 (*Gryllus bimaculatus*);<br>25958290 (*Platystomos albinus*);<br>60311415 (*Euclidia glyphica*);<br>55886380 (*Locusta migratoria*);<br>60312749 (*Gryllus bimaculatus*) | tgcagaaggaggttgacaggcttgaggatgaa<br>ttggtacacgagaaggagaagtacaagt |
| Bg031 | 144 | 55895696 (*Locusta migratoria*) | ttggtacacgagaaggagaagtacaagtacat |
| Bg031 | 145 | 60311892 (*Euclidia glyphica*);<br>55900730 (*Locusta migratoria*);<br>60311708 (*Euclidia glyphica*) | gagaaggagaagtacaagtacatttgtgacga<br>tcttgatatgactttcaccga |
| Bg031 | 146 | 77732463 (*Aedes aegypti*);<br>4378572 (*Periplaneta americana*);<br>19310970 (*Periplaneta fuliginosa*) | aacagcaggcccgcgacgccaac |
| Bg031 | 147 | 19310970 (*Periplaneta fuliginosa*);<br>60311610 (*Euclidia glyphica*);<br>60313268 (*Gryllus bimaculatus*) | catttgtgacgatcttgatatgactttcaccg<br>aacttattgg |
| Bg032 | 148 | 76169650 (*Diploptera punctata*) | cggacagggaggacatcaactc |
| Bg032 | 149 | 18888282 (*Anopheles gambiae*) | tggacaagtcgaagagcgtcaag |
| Bg032 | 150 | 91094918 (*Tribolium castaneum*) | ctgctccaagatccagaaaca |
| Bg033 | 151 | 60310034 (*Scarabaeus laticollis*);<br>83933868 (*Lutzomyia longipalpis*);<br>90137292 (*Spodoptera frugiperda*);<br>82610902 (*Tineola bisselliella*);<br>5853355 (*Lymantria dispar*);<br>50818292 (*Heliconius melpomene*);<br>22474252 (*Helicoverpa armigera*);<br>58371832 (*Lonomia obliqua*);<br>3719570 (*Manduca sexta*);<br>25959205 (*Meladema coriacea*);<br>53883538 (*Plutella xylostella*);<br>34787974 (*Callosobruchus maculatus*);<br>16901146 (*Ctenocephalides felis*);<br>60309684 (*Scarabaeus laticollis*);<br>78050191 (*Heliconius erato*);<br>57963831 (*Heliconius melpomene*);<br>60305522 (*Mycetophagus quadripustulatus*);<br>60295481 (*Homalodisca coagulata*);<br>71539924 (*Oncometopia nigricans*);<br>29556355 (*Bombyx mori*);<br>14010638 (*Heliothis virescens*);<br>5853355 (*Lymantria dispar*);<br>293219 (*Manduca sexta*); | gaggcccagagcaagagaggtatcctcactct<br>gaagtaccccat |

TABLE 4-continued

| Target ID | SEQ ID NO | Example GI-number and species | Sequence* |
|---|---|---|---|
| | | 40218737 (*Spodoptera exigua*);<br>67838313 (*Drosophila pseudoobscura*) | |
| Bg033 | 152 | 83662157 (*Myzus persicae*) | gctccagaggaacacccaatcct |
| Bg033 | 153 | 71543527 (*Oncometopia nigricans*);<br>60295481 (*Homalodisca coagulata*);<br>71048162 (*Oncometopia nigricans*) | atcctgctgactgaggctcccct |
| Bg033 | 154 | 49206619 (*Drosophila melanogaster*);<br>22474062 (*Helicoverpa armigera*);<br>29535046 (*Bombyx mori*);<br>60295481 (*Homalodisca coagulata*);<br>60336301 (*Homalodisca coagulata*);<br>62387502 (*Reticulitermes flavipes*);<br>60311490 (*Euclidia glyphica*);<br>91082248 (*Tribolium castaneum*);<br>67838313 (*Drosophila pseudoobscura*);<br>24251124 (*Culicoides* sp.);<br>60304993 (*Dascillus cervinus*);<br>25956497 (*Biphyllus lunatus*);<br>62239347 (*Diabrotica virgifera*);<br>55783599 (*Apriona germari*);<br>50818328 (*Heliconius melpomene*);<br>75723625 (*Tribolium castaneum*);<br>60305522 (*Mycetophagus quadripustulatus*);<br>49395567 (*Drosophila melanogaster*);<br>67838495 (*Drosophila pseudoobscura*);<br>50818292 (*Heliconius melpomene*) | aaggccaacagggagaagatgactcaaatcat<br>gtttgagaccttcaa |
| Bg033 | 155 | 25959205 (*Meladema coriacea*);<br>18923947 (*Anopheles gambiae*);<br>3477239 (*Drosophila melanogaster*);<br>29556355 (*Bombyx mori*);<br>56772582 (*Drosophila virilis*);<br>34788040 (*Callosobruchus maculatus*);<br>60315015 (*Tricholepisma aurea*);<br>49395567 (*Drosophila melanogaster*);<br>60314849 (*Tnicholepisma aurea*);<br>60314729 (*Tnicholepisma aurea*);<br>34787974 (*Callosobruchus maculatus*);<br>60315012 (*Tnicholepisma aurea*);<br>50560908 (*Homalodisca coagulata*);<br>62387502 (*Reticulitermes flavipes*);<br>60305522 (*Mycetophagus quadripustulatus*);<br>62387510 (*Reticulitermes flavipes*);<br>60295481 (*Homalodisca coagulata*) | caaatcatgtttgagaccttcaacacccc |
| Bg033 | 156 | 71547931 (*Oncometopia nigricans*);<br>60311490 (*Euclidia glyphica*);<br>75723625 (*Tribolium castaneum*);<br>49394847 (*Drosophila melanogaster*);<br>61949513 (*Tribolium castaneum*) | tcatgtttgagaccttcaacacccccgccatg<br>tatgt |
| Bg033 | 157 | 37951847 (*Ips pini*);<br>60299272 (*Diaphorina citri*);<br>73615611 (*Aphis gossypii*);<br>84648237 (*Myzus persicae*);<br>86461101 (*Acyrthosiphon pisum*);<br>52630958 (*Toxoptera citricida*);<br>34788040 (*Callosobruchus maculatus*);<br>60315015 (*Tricholepisma aurea*) | accttcaacacccccgccatgtatgttgccat<br>ccaggc |
| Bg033 | 158 | 37804525 (*Rhopalosiphum padi*);<br>86307561 (*Culex pipiens*);<br>62238804 (*Diabrotica virgifera*);<br>40310862 (*Timarcha balearica*);<br>49005801 (*Drosophila melanogaster*);<br>83933868 (*Lutzomyia longipaipis*) | cccgccatgtatgttgccatccaggccgt |
| Bg033 | 159 | 67782282 (*Aedes aegypti*);<br>48718502 (*Anopheles funestus*);<br>18933335 (*Anopheles gambiae*);<br>58385473 (*Anopheles gambiae* str. PEST);<br>66509773 (*Apis mellifera*);<br>45331062 (*Megachile rotundata*);<br>18923947 (*Anopheles gambiae*); | gccatccaggccgtgctgtccct |

TABLE 4-continued

| Target ID | SEQ ID NO | Example GI-number and species | Sequence* |
|---|---|---|---|
| | | 60312762 (*Gryllus bimaculatus*); 90137292 (*Spodoptera frugiperda*) | |
| Bg033 | 160 | 60312762 (*Gryllus bimaculatus*) | tacgcttccggccgtaccactggtattgtg |
| Bg033 | 161 | 30031443 (*Toxoptera citricida*) | gcttccggccgtaccactggtat |
| Bg033 | 162 | 34788040 (*Callosobruchus maculatus*); 19613046 (*Anopheles gambiae*); 92043996 (*Drosophila willistoni*); 58375293 (*Anopheles gambiae* str. PEST) | cgtaccactggtattgtgctggactctggtga |
| Bg033 | 163 | 18938956 (*Anopheles gambiae*); 92926094 (*Drosophila virilis*) | ggtattgtgctggactctggtgacgg |
| Bg033 | 164 | 92473382 (*Drosophila erecta*); 78050191 (*Heliconius erato*); 78230609 (*Heliconius erato/himera* mixed EST library) | ggtgacggcgtctcccacaccgt |
| Bg033 | 165 | 29556355 (*Bombyx mori*); 55923288 (*Locusta migratoria*) | gtctcccacaccgtacccatctatgaaggtta |
| Bg033 | 166 | 60304032 (*Eucinetus* sp.); 37951847 (*Ips pini*); 60310034 (*Scarabaeus laticollis*); 55913655 (*Locusta migratoria*) | tcccacaccgtacccatctatgaaggttacgc |
| Bg033 | 167 | 60311532 (*Euclidia glyphica*); 60311490 (*Euclidia glyphica*); 62387510 (*Reticulitermes flavipes*); 60309684 (*Scarabaeus laticollis*) | tgaagtaccccattgaacatggaatcatcacc aactggga |
| Bg033 | 168 | 92948842 (*Drosophila ananassae*); 62387555 (*Reticulitermes flavipes*); 3113938 (*Drosophila melanogaster*); 68267390 (*Drosophila simulans*); 12802910 (*Coptotermes acinaciformis*); 55917578 (*Locusta migratoria*); 78050191 (*Heliconius erato*) | tgccccatgccatcctgcgtctggactt |
| Bg033 | 169 | 78231052 (*Heliconius erato/himera* mixed EST library); 29551161 (*Bombyx mori*); 55888553 (*Locusta migratoria*); 33528426 (*Trichoplusia ni*); 22474252 (*Helicoverpa armigera*); 55896579 (*Locusta migratoria*) | gccatcctgcgtctggacttggccggccgt |
| Bg033 | 170 | 55924447 (*Locusta migratoria*); 57963831 (*Heliconius melpomene*); 293219 (*Manduca sexta*); 60314729 (*Tricholepisma aurea*); 50818292 (*Heliconius melpomene*) | cgtctggacttggccggccgtgacttgac |
| Bg033 | 171 | 55901019 (*Locusta migratoria*); 67877117 (*Drosophila pseudoobscura*); 42765807 (*Armigeres subalbatus*); 92044691 (*Drosophila willistoni*); 91718815 (*Liriomyza huidobrensis*); 67838313 (*Drosophila pseudoobscura*) | cgtgacttgactgactacctgatgaagatcct |
| Bg033 | 172 | 13761518 (*Drosophila melanogaster*); 18938956 (*Anopheles gambise*); 18923947 (*Anopheles gambiae*); 18933335 (*Anopheles gambiae*); 18928068 (*Anopheles gambiae*); 77731484 (*Aedes aegypti*); 21260592 (*Culex pipiens*); 20146853 (*Simulium vittatum*); 51978737 (*Bacillus cereus*) | gactacctgatgaagatcctgaccgagcgtgg ctac |
| Bg033 | 173 | 12802910 (*Coptotermes acinaciformis*) | atgaagatcctgaccgagcgtggctacagctt cac |
| Bg033 | 174 | 84648237 (*Myzus persicae*); 86461101 (*Acyrthosiphon pisum*); | ggaatcatcaccaactgggatgacatgga |

TABLE 4-continued

| Target ID | SEQ ID NO | Example GI-number and species | Sequence* |
|---|---|---|---|
| | | 73618206 (*Aphis gossypii*); 55913634 (*Locusta migratoria*); 37804558 (*Rhopalosiphum padi*); 52630958 (*Toxoptera citricida*); 37593622 (*Pediculus humanus*); 49395567 (*Drosophila melanogaster*); 37951847 (*Ips pini*) | |
| Bg033 | 175 | 55888553 (*Locusta migratoria*); 53883538 (*Plutella xylostella*); 29535046 (*Bombyx mori*); 2700128 (*Drosophila melanogaster*); 50560971 (*Homalodisca coagulata*); 55901019 (*Locusta migratoria*); 29551161 (*Bombyx mori*); 55901019 (*Locusta migratoria*); 22474062 (*Helicoverpa armigera*); 50560971 (*Homalodisca coagulata*); 55888553 (*Locusta migratoria*); 53883538 (*Plutella xylostella*); 29556355 (*Bombyx mori*); 55901019 (*Locusta migratoria*); 55901019 (*Locusta migratoria*) | atcatcaccaactgggatgacatggagaagatctggca |
| Bg033 | 176 | 677900 (*Aedes aegypti*); 42764600 (*Armigeres subalbatus*); 51978737 (*Bacillus cereus*); 86465013 (*Bombyx mori*); 90811718 (*Culex pipiens*); 92460622 (*Drosophila erecta*); 67838495 (*Drosophila pseudoobscura*); 92926494 (*Drosophila virilis*); 83934452 (*Lutzomyia longipalpis*); 90814004 (*Nasonia vitripennis*); 71547039 (*Oncometopia nigricans*); 60315012 (*Tricholepisma aurea*); 71048162 (*Oncometopia nigricans*); 82610902 (*Tineola bisselliella*); 60310034 (*Scarabaeus laticollis*); 5853355 (*Lymantria dispar*); 60309684 (*Scarabaeus laticollis*); 49005801 (*Drosophila melanogaster*); 60314849 (*Tricholepisma aurea*); 60312762 (*Gryllus bimaculatus*); 60314729 (*Tricholepisma aurea*); 60311532 (*Euclidia glyphica*); 3338522 (*Drosophila melanogaster*); 55886573 (*Locusta migratoria*); 34579881 (*Aedes aegypti*); 25959205 (*Meladema coriacea*); 57963831 (*Heliconius melpomene*); 58371832 (*Lonomia obliqua*); 78230609 (*Heliconius erato/himera* mixed EST library) | gacatggagaagatctggcatcacaccttctacaa |
| Bg033 | 177 | 25957102 (*Carabus granulatus*); 18939947 (*Anopheles gambiae*); 56152104 (*Rhynchosciara americana*); 60315012 (*Tricholepisma aurea*); 60310833 (*Agriotes lineatus*); 60297606 (*Diaprepes abbreviatus*); 25958625 (*Curculio glandium*); 34787974 (*Callosobruchus maculatus*) | atggagaagatctggcatcacaccttctacaatgaa |
| Bg033 | 178 | 25956583 (*Biphyllus lunatus*); 37951847 (*Ips pini*); 40544541 (*Tribolium castaneum*); 56772582 (*Drosophila virilis*); 34788040 (*Callosobruchus maculatus*); 25956497 (*Biphyllus lunatus*) | aagatctggcatcacaccttctacaatgaactccg |
| Bg033 | 179 | 16901057 (*Ctenocephalides felis*); 56772662 (*Drosophila virilis*); 60310833 (*Agriotes lineatus*); 57963831 (*Heliconius melpomene*); 60297606 (*Diaprepes abbreviatus*); 60314729 (*Tnicholepisma aurea*); | atctggcatcacaccttctacaatgaactccgagt |

TABLE 4-continued

| Target ID | SEQ ID NO | Example GI-number and species | Sequence* |
|---|---|---|---|
| | | 60311490 (*Euclidia glyphica*); 87266181 (*Choristoneura fumiferana*); 62239347 (*Diabrotica virgifera*); 60315015 (*Tricholepisma aurea*); 677900 (*Aedes aegypti*); 51978737 (*Bacillus cereus*); 5853355 (*Lymantria dispar*); 55783599 (*Apriona germari*); 83934452 (*Lutzomyia longipalpis*); 19848020 (*Chelonus inanitus*); 82610902 (*Tineola bisselliella*); 42765392 (*Armigeres subalbatus*); 82611040 (*Trox* sp.) | |

TABLE 5

| Target ID | SEQ ID NO | Example GI-number and species | Sequence* |
|---|---|---|---|
| Bg005 | 180 | 82835847 (*Boophilus microplus*); 63511642 (*Ixodes scapularis*) | aacgtgttcaagaacaagcgtgtcct |
| Bg005 | 181 | 82835847 (*Boophilus microplus*) | catccacaagaagaaggctgagaaggccagg |
| Bg031 | 182 | 21642857 (*Amblyomma variegatum*); 4325305 (*Boophilus microplus*); 49549243 (*Rhipicephalus appendiculatus*) | gccatcaagaagaagatgcaggcgatgaagctggagaag ga |
| Bg031 | 183 | 22758956 (*Haemaphysalis longicornis*) | cctgcagaagaagatccagcagat |
| Bg031 | 184 | 83308264 (*Dermanyssus gallinae*); 22758956 (*Haemaphysalis longicornis*) | aagatgcaggcgatgaagctggagaaggacaa |
| Bg031 | 185 | 21642857 (*Amblyomma variegatum*); 29779612 (*Ornithodoros porcinus*); | gagaaggacaaggccctgcag |
| Bg031 | 186 | 10707547 (*Amblyomma americanum*); 21642025 (*Amblyomma variegatum*); 49535169 (*Rhipicephalus appendiculatus*) | gttgtcggcaacaacctgaagtccct |
| Bg031 | 187 | 29779612 (*Ornithodoros porcinus*) | aaggaggctgaagctcgtgctga |
| Bg033 | 188 | 28627064 (*Mesobuthus gibbosus*) | gaggcccagagcaagagaggtatcctc |
| Bg033 | 189 | 68767268 (*Acanthoscurria gomesiana*) | cagagcaagagaggtatcctcac |
| Bg033 | 190 | 18143239 (*Araneus ventricosus*) | gcccagagcaagagaggtatcctcactctgaagt |
| Bg033 | 191 | 32423713 (*Haemaphysalis longicornis*) | aaggccaacagggagaagatgac |
| Bg033 | 192 | 45269080 (*Ornithodoros moubata*) | gagaagatgactcaaatcatgtt |
| Bg033 | 193 | 32423713 (*Haemaphysalis longicornis*) | ggtatcctcactctgaagtaccccattga |
| Bg033 | 194 | 68764791 (*Acanthoscurria gomesiana*) | atcatgtttgagaccttcaac |
| Bg033 | 195 | 10708501 (*Amblyomma americanum*); 60730229 (*Ixodes ricinus*); 63510574 (*Ixodes scapularis*); 49538235 (*Rhipicephalus appendiculatus*); 77539276 (*Ornithodoros moubata*); 29779134 (*Ornithodoros porcinus*) | gagaccttcaacacccccgccatgta |
| Bg033 | 196 | 10708501 (*Amblyomma americanum*) | gccatccaggccgtgctgtccct |
| Bg033 | 197 | 77539276 (*Ornithodoros moubata*); 29779134 (*Ornithodoros porcinus*); 68764791 (*Acanthoscurria gomesiana*) | gtctcccacaccgtacccatctatgaaggttacgc |
| Bg033 | 198 | 68767268 (*Acanthoscurria gomesiana*); 77539276 (*Ornithodoros moubata*); 29779134 (*Ornithodoros porcinus*); 45269080 (*Ornithodoros moubata*); 68758323 (*Acanthoscurria gomesiana*) | tcaccaactgggatgacatggagaagatctggcatcacac |

TABLE 5-continued

| Target ID | SEQ ID NO | Example GI-number and species | Sequence* |
|---|---|---|---|
| Bg033 | 199 | 68764791 (*Acanthoscurria gomesiana*) | gacatggagaagatctggcatcacaccttctacaa |
| Bg033 | 200 | 18143239 (*Araneus ventricosus*); 28627064 (*Mesobuthus gibbosus*) | atggagaagatctggcatcacaccttctacaatgaactccg |

EXAMPLES

Example 1

Cloning of a Partial Sequence of the *Blattella germanica* Bg001, Bg003, Bg004 and Bg005 Genes Via Family PCR High quality, intact RNA was isolated from *Blattella germanica* (source: Central Science Laboratory, York) using TRIzol Reagent (Cat. No. 15596-026/15596-018, Invitrogen, Rockville, Md., USA) following the manufacturers directions. Genomic DNA present in the RNA preparation was removed by Dnase treatment as prescribed by the manufacturer. cDNA was generated using a commercially available kit (SuperScript™ III Reverse Transcriptase, Cat No 18080044, Invitrogen, Rockville, Md., USA) following the manufacturers directions.

To isolate cDNA sequences comprising a portion of the Bg001, Bg003, Bg004 and Bg005 genes, a series of PCR reactions with degenerate primers were performed using Amplitaq Gold (Cat. No. N8080240; Applied Biosystems) as prescribed by the manufacturer.

For Bg001, the degenerate primers oGBKA002 and oGBKA020 (represented herein as SEQ ID NO 3 and SEQ ID NO 4 respectively) were used in two independent PCR reactions with the following conditions: 10 minutes at 95° C., followed by 40 cycles of 30 seconds at 95° C., 1 minute at 57° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 1 and is referred to as the partial sequence of the Bg001 gene. The corresponding partial amino acid sequence is herein represented as SEQ ID NO 2.

For Bg003, the degenerate primers oGBKC001 and oGBKC010 (represented herein as SEQ ID NO: 13 and SEQ ID NO: 14 respectively) were used in two independent PCR reactions with the following conditions: 10 minutes at 95° C., followed by 40 cycles of 30 seconds at 95° C., 1 minute at 55° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 11 and is referred to as the partial sequence of the Bg003 gene. The corresponding partial amino acid sequence is herein represented as SEQ ID NO 12.

For Bg004, the degenerate primers oGBKD001 and oGBKD006 (represented herein as SEQ ID NO 23 and SEQ ID NO 24 respectively) were used in two independent PCR reactions with the following conditions: 10 minutes at 95° C., followed by 40 cycles of 30 seconds at 95° C., 1 minute at 50° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 21 and is referred to as the partial sequence of the Bg004 gene. The corresponding partial amino acid sequence is herein represented as SEQ ID NO 22.

For Bg005, the degenerate primers oGBKE002 and oGBKE009 (represented herein as SEQ ID NO 33 and SEQ ID NO 34 respectively) were used in two independent PCR reactions with the following conditions: 10 minutes at 95° C., followed by 40 cycles of 30 seconds at 95° C., 1 minute at 52° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 31 and is referred to as the partial sequence of the Bg005 gene. The corresponding partial amino acid sequence is herein represented as SEQ ID NO 32.

Example 2

Cloning of a Partial Sequence of the *Blattella germanica* Bg031, Bg032 and Bg033 Genes Via EST Sequence High quality, intact RNA was isolated from *Blattella germanica* (source: Central Science Laboratory, York) using TRIzol Reagent (Cat. No. 15596-026/15596-018, Invitrogen, Rockville, Md., USA) following the manufacturers directions. Genomic DNA present in the RNA preparation was removed by DNAse treatment as prescribed by the manufacturer. cDNA was generated using a commercially available kit (SuperScript™ III Reverse Transcriptase, Cat No 18080044, Invitrogen, Rockville, Md., USA) following the manufacturers directions.

To identify a partial cDNA sequence from the Bg031, Bg032 and Bg033 genes, one EST per gene was found in the public database Genbank under accession numbers AF260897, X73679 and AY004248 respectively, originating from the public database Genbank.

To isolate cDNA sequences comprising a portion of the Bg031, Bg032 and Bg033 genes, a series of PCR reactions with EST based specific primers were performed using Perfectshot™ ExTaq (Cat No RR005A, TAKARA BIO INC.) as prescribed by the manufacturer.

For Bg031, the specific primers oGBLA001 and oGBLA002 (represented herein as SEQ ID NO 43 and SEQ ID NO 44 respectively) were used in two independent PCR reactions with the following conditions: 10 minutes at 95° C., followed by 40 cycles of 30 seconds at 95° C., 1 minute at 55° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 41 and is referred to as the partial sequence of the Bg031 gene. The corresponding partial amino acid sequence is herein represented as SEQ ID NO 42.

For Bg032, the specific primers oGBLB003 and oGBLB004 (represented herein as SEQ ID NO: 51 and SEQ ID NO: 52 respectively) were used in two independent PCR reactions with the following conditions: 10 minutes at 95° C., followed by 40 cycles of 30 seconds at 95° C., 1 minute at 55° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 49 and is referred to as the partial sequence of the Bg032 gene. The corresponding partial amino acid sequence is herein represented as SEQ ID NO 50.

For Bg033, the specific primers oGBLC001 and oGBLC004 (represented herein as SEQ ID NO 59 and SEQ ID NO 60 respectively) were used in two independent PCR reactions with the following conditions: 10 minutes at 95° C., followed by 40 cycles of 30 seconds at 95° C., 1 minute at 55° C. and 1 minute at 72° C., followed by 7 minutes at 72° C. The resulting PCR products were analyzed on agarose gel, purified (QIAquick Gel Extraction Kit; Cat. No 28706, Qiagen), cloned into the pCR4-TOPO vector (Cat. No. K4575-40, Invitrogen) and sequenced. The consensus sequence resulting from the sequencing of both PCR products is herein represented by SEQ ID NO 57 and is referred to as the partial sequence of the Bg033 gene. The corresponding partial amino acid sequence is herein represented as SEQ ID NO 58.

Example 3 dsRNA Production of the *Blattella germanica* Bg001, Bg003, Bg004, Bg005, Bg031, Bg032 and Bg033 Genes dsRNA was synthesized in milligram amounts using the commercially available kit T7 RiboMAX™ Express RNAi System (Cat. No. P1700, Promega). First two separate single 5' T7 RNA polymerase promoter templates were generated in two separate PCR reactions, each reaction containing the target sequence in a different orientation relative to the T7 promotor.

For Bg001 the sense T7 template was generated using the specific T7 FW primer oGBLD001 and the specific RV primer oGBLD010 (represented herein as SEQ ID NO 5 and SEQ ID NO 6 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLD009 and the specific T7 RV primer oGBLD002 (represented herein as SEQ ID NO 7 and SEQ ID NO 8 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 9.

For Bg003 the sense T7 template was generated using the specific T7 FW primer oGBLD003 and the specific RV primer oGBLD012 (represented herein as SEQ ID NO 15 and SEQ ID NO 16 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLD011 and the specific T7 RV primer oGBLD004 (represented herein as SEQ ID NO: 17 and SEQ ID NO: 18 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 19.

For Bg004 the sense T7 template was generated using the specific T7 FW primer oGBLD005 and the specific RV primer oGBLD014 (represented herein as SEQ ID NO 25 and SEQ ID NO 26 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLD013 and the specific T7 RV primer oGBLD006 (represented herein as SEQ ID NO: 27 and SEQ ID NO: 28 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 29.

For Bg005 the sense T7 template was generated using the specific T7 FW primer oGBLD007 and the specific RV primer oGBLD016 (represented herein as SEQ ID NO 35 and SEQ ID NO 36 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLD015 and the specific T7 RV primer oGBLD008 (represented herein as SEQ ID NO: 37 and SEQ ID NO: 38 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 39.

For Bg031 the sense T7 template was generated using the specific T7 FW primer oGBLA007 and the specific RV primer oGBLA002 (represented herein as SEQ ID NO 45 and SEQ ID NO 44 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLA001 and the specific T7 RV primer oGBLA008 (represented herein as SEQ ID NO 43 and SEQ ID NO 46 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 47.

For Bg032 the sense T7 template was generated using the specific T7 FW primer oGBLB007 and the specific RV primer oGBLB004 (represented herein as SEQ ID NO 53 and SEQ ID NO 52 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLB003 and the specific T7 RV primer oGBLB008 (represented herein as SEQ ID NO 51 and SEQ ID NO 54 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 55.

For Bg033 the sense T7 template was generated using the specific T7 FW primer oGBLC007 and the specific RV primer oGBLC004 (represented herein as SEQ ID NO 61 and SEQ ID NO 60 respectively) in a PCR reaction with the following conditions: 4 minutes at 95° C., followed by 35 cycles of 30 seconds at 95° C., 30 seconds at 51° C. and 1 minute at 72° C., followed by 10 minutes at 72° C. The anti-sense T7 template was generated using the specific FW primer oGBLC001 and the specific T7 RV primer oGBLC008 (represented herein as SEQ ID NO 59 and SEQ ID NO 62 respectively) in a PCR reaction with the same conditions as described above. The resulting PCR products were analyzed on agarose gel and purified by $NaClO_4$ precipitation. The generated T7 FW and RV templates were mixed to be transcribed and the resulting RNA strands were annealed, Dnase and Rnase treated, and purified by sodium acetate, following the manufacturer's directions. The sense strand of the resulting dsRNA is herein represented by SEQ ID NO 63.

Example 4

Laboratory Trials to Screen dsRNA Targets for Activity Against the German Cockroach, *Blattella germanica*

Stock solutions of 1-10 μg/μl dsRNA in distilled water were prepared. Each dsRNA solution was diluted to the appropriate concentration and mixed with finely ground laboratory diet (Rat and mouse standard diet, B&K Universal Ltd, Hull, UK), which was previously heat treated in order to inactivate any enzymes. The mixture or formulation was formed into small pellets of equal weight (0.3 g) to achieve an end concentration of 0.1% to 2% w/w dsRNA and dried overnight at room temperature.

Newly hatched nymphs from the German cockroach, *B. germanica* were housed per 10 in plastic lidded containers (29±2° C., minimum 40% relative humidity, with a 12:12 light:dark photoperiod). Animals were starved 24 hours prior to exposure to the pellets. The cockroaches were assessed as live, moribund or dead twice a week until adulthood. The pellet was replaced with freshly prepared pellet once a week. dsRNA containing pellets, formulations, were compared with a negative control (solvent) and a positive control (1 or 2% imidacloprid, commonly used in commercially available cockroach baits). As shown in FIG. 1, at least 80% of the cockroaches died within 24 days after first administration when treated with Bg001, Bg003 and Bg005, or within 29 days when treated with Bg004 respectively.

Example 5

Testing Different Fragments for Efficiency

Identification of a Fragment of the *Blattella germanica* Bg001, Bg003, Bg004, Bg005, Bg031, Bg032 and Bg033 Genes with No Substantial Homology to Human The partial sequences of the Bg001, Bg003, Bg004, Bg005, Bg031, Bg032 and Bg033 genes, herein represented respectively as SEQ ID NO 1, SEQ ID NO 11, SEQ ID NO 21, SEQ ID NO 31, SEQ ID NO 41, SEQ ID NO 49 and SEQ ID NO 57, were analyzed to find fragments with no substantial homology to non-target organisms. In particular, since the dsRNA will be diced in the organism to siRNA molecules, the sequences were scanned for siRNA sequences that would have homology to non-target species. Such siRNA could cause adverse effects in the non-target organism und should therefore preferably be avoided in the dsRNA fragment to be incorporated in the end products. The selected fragments are suitable for cockroach control by RNA interference when for instance present in the bait and taken up by a cockroach feeding from the bait. For this analysis, non-target organism was human (*Homo sapiens*). Fragments of 21 contiguous nucleotides (best1_human__21__0), or 24 contiguous nucleotides allowing three mismatches (best1/2/3_human__24__3), that do not occur in the non-target organism were identified and are named herein "freefrags." The longest sequence of Bg001, Bg003, Bg004, Bg005, Bg031, Bg032 and Bg033 free of non-target organism sequences using the first selection criterium was given a SEQ ID NO and named herein "freefrag". These Bg001, Bg003, Bg004, Bg005, Bg031, Bg032 and Bg033 freefrags, are herein represented as SEQ ID NO 10, SEQ ID NO 20, SEQ ID NO 30, SEQ ID NO 40, SEQ ID NO 48, SEQ ID NO 56 and SEQ ID NO 64, respectively. The length and sequence of some examples of other freefrag sequences suitable for use in the present invention is represented in Table 2. The exact sequence can easily be deduced from the table. All freefrag sequences described in the table belong to the group of sequences of the invention.

A person skilled in the art will recognize that many more such freefrags, of various lengths, may be identified in the *Blatella germanica* sequences herein presented, as well as in sequences which are orthologues of the corresponding genes and proteins in the other pest sequences according to the invention, and accordingly, the present invention extends to these further identifiable freefrags.

Example 6

Choosing the Optimal Fragment; Testing Concatemers for Efficacy

Concatemers were designed for each target gene. Concatemers are synthetic tandem repeats of 50 to 100 bp dsfragments. In the present example, concatemers were designed by selecting the best possible fragments in regions with homology in protein family as well as at nucleotide level, in regions containing the best predicted siRNAs and in regions with between 40 and 60% GC content, preferably about 50% GC content, if possible.

For Bg001 two concatemers were designed consisting of a five times repeat of a 50 bp fragment, ie represented by SEQ ID NO 65 and 66, resulting in Bg001 concatemer 1 and Bg001 concatemer 2, herein represented respectively as SEQ ID NO 67 and SEQ ID NO 68, and one concatemer was designed consisting of a three times repeat of a 100 bp repeat, ie represented by SEQ ID NO 69, resulting in Bg001 concatemer 3, herein represented as SEQ ID NO 70. XbaI and SmaI flanking sites were added for cloning in a vector to produce dsRNA. These dsRNA constructs comprising the concatemers were tested in the cockroach laboratory trials.

In a further experiment as shown in FIG. 2, mortality was significant higher when treated with Bg001 and Bg001 concatemer 2 compared to the negative control (solvent).

Besides mortality, treatment showed a significant effect on development. For example at day 48, from the surviving cockroaches treated with Bg001 only 33.3% moulted to the adult stage whereas none of the cockroaches treated with Bg001 concatemer 2 did within this time as shown in Table 3.

Example 7

Testing Different Formulations

RNA interference (RNAi) is a potentially very powerful tool to inhibit the expression of target genes in a sequence-specific manner in many different species. However, for RNAi to be valuable and effective, specific silencing of any given target gene is essential, devoid of nonspecific knockdown and toxic side effects. Applications of dsRNA have been hindered by the inability to effectively deliver these compounds to their sites of action within cells. Progress in chemical modification of the dsRNA to enhance the strength and stability of interaction, without losing specificity, is ongoing. In this study an evaluation is made of a few concepts for delivery of dsRNA to target genes in *B. germanica.*

RNAi induced effects can be improved by increasing the intracellular uptake of dsRNA by facilitating endocytosis or by increasing the stability of the dsRNA in the biological environment using delivery agents such as lipids and liposomes. siRNAs have anionic phosphodiester backbones and for this reason, cationic liposome/lipid-mediated siRNA delivery (siFection) is investigated. These cationic liposome/lipid-based systems are selected from a number of commercially available products, including lipofectamine and 1,2-dioleoyl-3-trimethyl-ammonium-propane (DOTAP)-cholesterol, and test the dsRNA formulations in the cockroach laboratory trials. Parameters to be investigated include the lipid:dsRNA ratio of mixing, the extent of cationic liposome/lipid-dsRNA complex formation, the particle size, the mode of delivery and the dose-response effect.

Example 8

Testing for dsRNA Stability

Application of dsRNA for gene silencing will be dependent on improvements in molecule bio-stability, specificity and delivery.

The stability of the generated dsRNAs was tested in TRIZMA buffer at pH 7 and pH 9 and in CAPS buffer at pH 11 to mimic the pH in the gut of some target species. dsRNA was incubated for several days and aliquots were analyzed on 20% polyacrylamide gels at different time intervals. No influence of the pH on the stability of the dsRNA could be observed based on the gel results.

The stability of the generated dsRNAs as a function of time was tested in RNAse free water and in LB medium at room temperature over a period of eight months. Aliquots were taken weekly and/or monthly and stored at −20° C. prior to analysis on 20% polyacrylamide gels. No significant degradation of the dsRNA could be observed on a polyacrylamide gel as shown in FIG. 3;

Example 9

Laboratory Trial to Test a Single Dose dsRNA on Mortality in the Early Nymphal Stage of the German Cockroach, *Blattella germanica*

A stock solution of 10 μg/μl dsRNA in distilled water was prepared and mixed with finely ground laboratory diet (Rat and mouse standard diet, B&K Universal Ltd, Hull, UK), which was previously heat treated in order to inactivate any enzymes. The mixture or formulation was formed into small pellets of equal weight (0.3 g) to achieve an end concentration of 1% w/w dsRNA and dried overnight at room temperature.

Newly hatched nymphs from the German cockroach, *B. germanica* were housed per 10 in plastic lidded containers (29±2° C., minimum 40% relative humidity, with a 12:12 light:dark photoperiod). Animals were starved 24 hours prior to exposure to the pellets. After one week, this initial dose was replaced with untreated pellet. The cockroaches were assessed as live, moribund or dead twice a week until adulthood. Bg001 dsRNA containing pellet showed significant higher mortality compared to the two negative controls (solvent and miscellaneous dsRNA) as shown in FIG. 4.

The invention claimed is:

1. An RNA construct comprising at least one double stranded RNA region, at least one strand of which comprises a nucleotide sequence that is complementary to at least 24 nucleotides of a nucleotide sequence as set forth in any one of SEQ ID NOs: 1, 6, 9, 10, 65 to 70, 73 to 76 and 78, or the complement thereof, or an orthologous nucleotide sequence from a Blattodea species, wherein the orthologous nucleotide sequence has at least 80% sequence identity with the nucleotide sequence of SEQ ID NO: 1, wherein the percentage sequence identity is calculated over the same length.

2. The RNA construct according to claim 1 wherein the complementarity of said nucleotide sequence comprises at least 95% nucleotide sequence identity with (i) at least 25 nucleotides of any one of the nucleotide sequences as defined in claim 1, or the complement thereof, wherein the percentage sequence identity is calculated over the same length.

3. The RNA construct according to claim 1 wherein the nucleotide sequence comprised in the at least one strand has less than 12.5% sequence identity over 24 contiguous nucleotides with the corresponding nucleotide sequence from a mammalian species.

4. The RNA construct according to claim 1 comprising at least two nucleotide sequences independently chosen from any of SEQ ID NOs 1, 6, 9, 10, 65 to 70, 73 to 76 and 78, for instance any of SEQ ID NOs 65 to 70.

5. The RNA construct of claim 1 which comprises at least one additional dsRNA region, at least one strand of which comprises a nucleotide sequence that is complementary to at least 21 nucleotides of the nucleotide sequence of a further gene from a Blattodea species.

6. The RNA construct according to claim 5 wherein the complementarity of said nucleotide sequence comprises at least 70% nucleotide sequence identity, wherein the percentage sequence identity is calculated over the same length.

7. The RNA construct according to claim 5 wherein the at least one strand has less than 12.5% sequence identity over 24 contiguous nucleotides with the corresponding nucleotide sequence from a mammalian species.

8. The RNA construct according to claim 7, wherein the mammalian species is a human.

9. The RNA construct of claim 1, further comprising at least one additional functional sequence and optionally a linker.

10. The RNA construct according to claim 9 wherein said additional functional sequence is a sequence facilitating large-scale production of the RNA construct.

11. The RNA construct according to claim 9 wherein the linker is a conditionally self-cleaving RNA sequence, optionally a pH sensitive linker or a hydrophobic sensitive linker.

12. The RNA construct according to claim 9 wherein the linker is an intron.

13. The RNA construct according to claim 9 wherein said additional functional sequence is a sequence effecting an increase or decrease in the stability of the dsRNA.

14. The RNA construct according to claim 9 wherein said additional functional sequence is a sequence allowing the binding of proteins or other molecules to facilitate uptake of the RNA construct by a Blattodea.

15. The RNA construct according to claim 9 wherein said additional functional sequence is a sequence which is an aptamer that binds to receptors or to molecules in the gut of an insect to facilitate uptake, endocytosis and/or transcytosis by Blattodea.

16. The RNA construct according to claim 1 wherein the at least one strand comprises at least 27 nucleotides or more of any of the nucleic acid molecules comprising the nucleotide sequence as set forth in any of SEQ ID NOs 1, 9, 10, 65 to 70, 74 and 75, or the complement thereof.

17. A DNA construct comprising a nucleotide sequence encoding an RNA construct of claim 1.

18. An expression construct comprising a DNA construct according to claim 17.

19. An expression construct according to claim 18 further comprising one or more control sequences capable of driving expression of the nucleotide sequence; and optionally a transcription termination sequence.

20. A host cell comprising an RNA construct of claim 1.

21. The host cell as defined in claim 20, which is a bacterial cell.

22. The host cell as defined in claim 21, which is an inactivated bacterial cell.

23. A pesticide composition comprising an RNA construct as defined in claim 1 together with a suitable carrier.

24. The composition according to claim 23 wherein the carrier comprises electrostatically charged powder or particles and/or magnetic particles, preferably metallic particles which are initially unmagnetised but which are capable of becoming magnetically polarised when subjected to the electrical field provided by the Blattodea body, which powder or particles adhere to the Blattodea cuticle and which may be ingested by a Blattodea.

25. The composition of claim 23 in combination with a further pesticide.

26. A housing or trap for Blattodea which contains a composition as defined in claim 23.

27. A kit comprising the RNA construct of claim 1 and instructions for using the RNA construct.

28. The kit of claim 27 which comprises multiple RNA constructs, wherein each double stranded RNA is capable of down regulating the expression of at least one Blattodea gene through RNA interference.

29. The kit of claim 27 wherein the multiple RNA constructs are used sequentially in order to reduce the probability of the Blattodea acquiring resistance.

30. A method of controlling Blattodea comprising administering to the Blattodea an RNA construct as defined in claim 1, wherein the double stranded RNA is capable of down regulating the expression of at least one Blattodea gene through RNA interference.

31. The method of claim 30, wherein multiple RNA constructs are administered to said Blattodea.

32. The method of claim 31, wherein the multiple RNA constructs are administered sequentially in order to reduce the probability of the Blattodea acquiring resistance.

33. The method according to claim 30, wherein the Blattodea is a *Blatella* spp., *Periplaneta* spp., *Blatta* spp. or *Supella* spp.

34. A method for controlling cockroach pests comprising providing to the cockroach an RNA construct comprising at least one double stranded RNA region, at least one strand of which comprises a nucleotide sequence that is complementary to at least 21 nucleotides of a nucleotide sequence as set forth in any of SEQ ID NOs 1, 6, 9, 10, 65-70, 73 to 76 and 78, or the complement thereof.

35. The method according to claim 24 wherein said cockroach pest is chosen from the species belonging to the group of genera consisting of *Blatella, Periplaneta, Blatta* and *Supella.*

36. A method according to claim 34 wherein said cockroach pest is chosen from the group consisting of German cockroach (*Blatella Germanica*), American cockroach (*Periplaneta americana*), Australian cockroach (*Periplaneta australiasiae*), Oriental cockroach (*Blatta orientalis*) and brown-banded cockroach (*Supella longipalpa*).

37. An RNA construct comprising at least one double stranded RNA region, at least one strand of which comprises at least 24 nucleotides or more of any of the nucleic acid molecules comprising the nucleotide sequence as set forth in any of SEQ ID NOs 1, 6, 9, 10, 65 to 70, 73 to 76 and 78, or the complement thereof.

38. A DNA construct comprising a region encoding an RNA construct of claim 5.

39. An expression construct comprising a DNA construct according to claim 38.

40. A host cell comprising an RNA construct of claim 5 or an expression construct of claim 39.

41. The host cell as defined in claim 40, which is a bacterial cell.

42. The host cell as defined in claim 41, which is an inactivated bacterial cell.

43. A pesticide composition comprising the host cell of claim 41.

44. The composition according to claim 43, which is in the form of a bait.

45. The composition according to claim 43, which is in the form of a spray, preferably a pressurized/aerosolized spray or pump spray.

46. A method for generating an RNA construct, comprising contacting a DNA construct of claim 17 with cell-free components under conditions that allow transcription of said DNA construct to produce said RNA construct.

47. The method of claim 46 wherein the cell is a bacterial cell.

48. A pesticide composition comprising an RNA construct as defined in claim 5 together with a suitable carrier.

49. The composition according to claim 48 which is in a form suitable for ingestion by a Blattodea species.

50. The composition according to claim 48 which is in solid form, such as a pellet or powder, liquid form or gel form.

51. The composition according to claim 48 which is in the form of a bait.

52. The composition according to claim 51 wherein the bait further includes at least one food substance, such as a protein based food or boric acid and/or an attractant, such as a pheromone.

53. The composition according to claim 48 wherein the composition is stored in a housing or trap which a Blattodea species can enter in order to ingest the composition.

54. The composition according to claim 48 which is in the form of a spray, preferably a pressurized/aerosolized spray or a pump spray.

55. The composition according to claim 48 which is in the form of a coating on a suitable surface which adheres to an insect and/or arachnid when it comes into contact with the coating.

56. The composition according to claim 48 wherein the carrier comprises electrostatically charged powder or particles and/or magnetic particles, preferably metallic particles which are initially unmagnetised but which are capable of becoming magnetically polarised when subjected to the electrical field provided by the Blattodea body, which adhere to the Blattodea cuticle.

57. The composition according to claim 48 wherein the carrier increases the uptake of the double stranded RNA into the Blattodea.

58. The composition of claim 57 wherein the carrier is a lipid-based carrier, preferably comprising one or more of, oil-in water emulsions, cholesterol, micelles, lipopolyamines and liposomes.

59. The composition of claim 57 wherein the carrier comprises a nucleic acid condensing agent, preferably spermidine or protamine sulphate.

60. A housing or trap for Blattodea species which contains a composition as defined in claim 48.

61. A method of controlling Blattodea species comprising administering to a Blattodea species an RNA construct as defined in claim 5, wherein the double stranded RNA is capable of down regulating the expression of at least one Blattodea gene through RNA interference.

62. The method of claim 61, wherein multiple RNA constructs are administered.

63. The method of claim 62, wherein the multiple RNA constructs are administered sequentially in order to reduce the probability of the pest acquiring resistance.

64. The method according to claim 61, wherein the Blattodea species is *Blatella* spp., *Periplaneta* spp., *Blatta* spp. or *Supella* spp.

65. The method according to claim 61 wherein the Blattodea species is growth delayed, paralysed, made infertile or killed.

66. A kit comprising the RNA construct of claim 5 and instructions for using the double stranded RNA construct.

67. The kit of claim 66 which comprises multiple RNA constructs, wherein each double stranded RNA is capable of down regulating the expression of at least one Blattodea gene through RNA interference.

68. The kit of claim 67 wherein the multiple RNA constructs are used sequentially in order to reduce the probability of the Blattodea acquiring resistance.

69. A method for generating an RNA construct, comprising culturing a host cell as defined in claim 20 under conditions that permit expression of the RNA construct.

70. The method of claim 69 further comprising purification of the RNA construct.

71. An expression construct comprising a DNA construct encoding the RNA construct of claim 1.

72. A host cell comprising the DNA construct of claim 17.

73. A pesticide composition comprising a host cell of claim 20 or claim 72 together with a suitable carrier.

74. The composition according to claim 73, which is in the form of a spray, preferably a pressurized/aerosolized spray or pump spray.

75. A method of controlling Blattodea species comprising administering to a Blattodea the host cell of claim 20 or claim 72.

76. The method of claim 75, wherein multiple host cells or compositions are administered to said Blattodea species.

77. The method of claim 76, wherein the multiple host cells or compositions are administered sequentially.

78. A method of controlling Blattodea species comprising administering to a Blattodea the host cell of claim 41, wherein the double stranded RNA is capable of down regulating the expression of at least one Blattodea gene through RNA interference.

79. The method of claim 78, wherein multiple host cells or compositions are administered to said Blattodea species.

80. A method for generating an RNA construct, comprising administering a DNA construct of claim 17 to a cell under conditions that allow transcription of said DNA construct to produce said RNA construct.

81. The method of claim 80 wherein the cell is a bacterial cell.

82. A housing or trap for Blattodea species which contains a composition as defined in claim 73.

83. A housing or trap for Blattodea species which contains the composition as defined in claim 43.

* * * * *

SEQUENCE LISTING

```
<160> NUMBER OF SEQ ID NOS: 200

<210> SEQ ID NO 1
<211> LENGTH: 624
<212> TYPE: DNA
<213> ORGANISM: Blattella germanica

<400> SEQUENCE: 1

taaggcatgg atgttggaca agctcggtgg agtgtatgct ccaagaccaa gcacaggacc     60

tcacaagtta cgagagagtc tgccccttgt aatatttctt cgtaataggc tgaaatatgc    120

attaaccaac tgtgaggtta agaaaattgt tatgcagcgc cttattaagg ttgatggaaa    180
```

-continued agtcagaaca gaccccaact atccagctgg ttttatggat gttgttacaa ttgaaaaaac 240
tggagaattt ttccgtctga tttatgacgt gaaaggacgt ttcaccattc acagaataac 300
tgctgaagaa gccaagtata aactgtgcaa ggtaaagaga gtgcagactg ggcccaaggg 360
tattccattc ttggtgaccc atgatggtag aactcttaga tatcctgatc ctgtcatcaa 420
agttaatgat acagttcaac ttgacatcgc tacttccaag attatggata gcatcaaatt 480
tgataatggt aatctctgta tgattactgg aggccgtaac ttgggtcgtg ttggaactgt 540
agttaatcga gaacgtcatc ctggttcctt tgacattgtg catgttaaag attcacaagg 600
acacacattt gctaccagat tgaa 624

<210> SEQ ID NO 2
<211> LENGTH: 208
<212> TYPE: PRT
<213> ORGANISM: Blattella germanica

<400> SEQUENCE: 2

```
Lys Ala Trp Met Leu Asp Lys Leu Gly Gly Val Tyr Ala Pro Arg Pro
1               5                   10                  15

Ser Thr Gly Pro His Lys Leu Arg Glu Ser Leu Pro Leu Val Ile Phe
            20                  25                  30

Leu Arg Asn Arg Leu Lys Tyr Ala Leu Thr Asn Cys Glu Val Lys Lys
        35                  40                  45

Ile Val Met Gln Arg Leu Ile Lys Val Asp Gly Lys Val Arg Thr Asp
    50                  55                  60

Pro Asn Tyr Pro Ala Gly Phe Met Asp Val Val Thr Ile Glu Lys Thr
65                  70                  75                  80

Gly Glu Phe Phe Arg Leu Ile Tyr Asp Val Lys Gly Arg Phe Thr Ile
                85                  90                  95

His Arg Ile Thr Ala Glu Glu Ala Lys Tyr Lys Leu Cys Lys Val Lys
            100                 105                 110

Arg Val Gln Thr Gly Pro Lys Gly Ile Pro Phe Leu Val Thr His Asp
        115                 120                 125

Gly Arg Thr Leu Arg Tyr Pro Asp Pro Val Ile Lys Val Asn Asp Thr
    130                 135                 140

Val Gln Leu Asp Ile Ala Thr Ser Lys Ile Met Asp Ser Ile Lys Phe
145                 150                 155                 160

Asp Asn Gly Asn Leu Cys Met Ile Thr Gly Gly Arg Asn Leu Gly Arg
                165                 170                 175

Val Gly Thr Val Val Asn Arg Glu Arg His Pro Gly Ser Phe Asp Ile
            180                 185                 190

Val His Val Lys Asp Ser Gln Gly His Thr Phe Ala Thr Arg Leu Asn
        195                 200                 205
```

<210> SEQ ID NO 3
<211> LENGTH: 23
<212> TYPE: DNA
<213> ORGANISM: Artificial sequence
<220> FEATURE:
<223> OTHER INFORMATION: Degenerate primer

<400> SEQUENCE: 3
catttgaagc gtttwrmygc ycc 23

<210> SEQ ID NO 4
<211> LENGTH: 27

<212> TYPE: DNA
<213> ORGANISM: Artificial sequence
<220> FEATURE:
<223> OTHER INFORMATION: specific primer

<400> SEQUENCE: 4
gtgcccttgc caatgatgaa cacgttg 27

<210> SEQ ID NO 5
<211> LENGTH: 45
<212> TYPE: DNA
<213> ORGANISM: Artificial sequence
<220> FEATURE:
<223> OTHER INFORMATION: specific T7 primer

<400> SEQUENCE: 5
cgctaatacg actcactata ggggagtgta tgctccaaga ccaag 45

<210> SEQ ID NO 6
<211> LENGTH: 24
<212> TYPE: DNA
<213> ORGANISM: Artificial sequence
<220> FEATURE:
<223> OTHER INFORMATION: specific primer

<400> SEQUENCE: 6
caatctggta gcaaatgtgt gtcc 24

<210> SEQ ID NO 7
<211> LENGTH: 23
<212> TYPE: DNA
<213> ORGANISM: Artificial sequence
<220> FEATURE:
<223> OTHER INFORMATION: specific primer

<400> SEQUENCE: 7
ggagtgtatg ctccaagacc aag 23

<210> SEQ ID NO 8
<211> LENGTH: 46
<212> TYPE: DNA
<213> ORGANISM: Artificial sequence
<220> FEATURE:
<223> OTHER INFORMATION: Synthetic T7 primer

<400> SEQUENCE: 8
cgctaatacg actcactata ggcaatctgg tagcaaatgt gtgtcc 46

<210> SEQ ID NO 9
<211> LENGTH: 594
<212> TYPE: RNA
<213> ORGANISM: Blattella germanica

<400> SEQUENCE: 9
ggaguguaug cuccaagacc aagcacagga ccucacaagu uacgagagag ucugccccuu 60
guaauauuuc uucguaauag gcugaaauau gcauuaacca acugugaggu uaagaaaauu 120
guuaugcagc gccuuauuaa gguugaugga aaagucagaa cagaccccaa cuauccagcu 180
gguuuuaugg auguuguuac aauugaaaaa acuggagaau uuuuccgucu gauuuaugac 240
gugaaaggac guuucaccau ucacagaaua acugcugaag aagccaagua uaaacugugc 300
aagguaaaga gagugcagac ugggcccaag gguauuccau ucuuggugac ccaugauggu 360
agaacucuua gauauccuga uccugucauc aaaguuaaug auacaguuca acuugacauc 420

-continued

```
gcuacuucca agauuaugga uagcaucaaa uuugauaaug guaaucucug uaugauuacu    480

ggaggccgua acuugggucg uguuggaacu guaguuaauc gagaacguca uccugguucc    540

uuugacauug ugcauguuaa agauucacaa ggacacacau uugcuaccag auug          594
```

<210> SEQ ID NO 10
<211> LENGTH: 573
<212> TYPE: RNA
<213> ORGANISM: Blattella germanica

<400> SEQUENCE: 10

```
ggaguguaug cuccaagacc aagcacagga ccucacaagu uacgagagag ucugccccuu     60

guaauauuuc uucguaauag gcugaaauau gcauuaacca acugugaggu uaagaaaauu    120

guuaugcagc gccuuauuaa gguugaugga aaagucagaa cagaccccaa cuauccagcu    180

gguuuuaugg auguuguuac aauugaaaaa acuggagaau uuuuccgucu gauuuaugac    240

gugaaaggac guuucaccau ucacagaaua acugcugaag aagccaagua uaaacugugc    300

aagguaaaga gagugcagac ugggcccaag gguauuccau ucuuggugac ccaugauggu    360

agaacucuua gauauccuga uccugucauc aaaguuaaug auacaguuca acuugacauc    420

gcuacuucca agauuaugga uagcaucaaa uuugauaaug guaaucucug uaugauuacu    480

ggaggccgua acuugggucg uguuggaacu guaguuaauc gagaacguca uccugguucc    540

uuugacauug ugcauguuaa agauucacaa gga                                 573
```

<210> SEQ ID NO 11
<211> LENGTH: 436
<212> TYPE: DNA
<213> ORGANISM: Blattella germanica

<400> SEQUENCE: 11

```
tcccaggcga ccttatgaaa aggcacgtct tgatcaggag ttgaaaatca taggagaata     60

tggtcttagg aacaaacgtg aagtgtggcg agtcaagtat accttggcaa aaatccgtaa    120

agctgccaga gaacttctga ctttggaaga gaaagatcag cgcaggttgt ttgaaggcaa    180

tgctcttctt cgtcggttgg tgcgtattgg agtgttggat gaaacccgta tgaagcttga    240

ttacgtcttg ggtttgaaga ttgaagattt cttggaacga cgtctccaaa cacaagtttt    300

caagttgggg cttgcaaaat caatccatca tgctcgtgtg ctgatccgtc aaagacatat    360

cagggttcgt aagcaggtcg tgaatattcc aagcttcatt gtgagacttg attcccagaa    420

gcatattgac ttctcg                                                    436
```

<210> SEQ ID NO 12
<211> LENGTH: 145
<212> TYPE: PRT
<213> ORGANISM: Blattella germanica

<400> SEQUENCE: 12

```
Pro Arg Arg Pro Tyr Glu Lys Ala Arg Leu Asp Gln Glu Leu Lys Ile
1               5                   10                  15

Ile Gly Glu Tyr Gly Leu Arg Asn Lys Arg Glu Val Trp Arg Val Lys
            20                  25                  30

Tyr Thr Leu Ala Lys Ile Arg Lys Ala Ala Arg Glu Leu Leu Thr Leu
        35                  40                  45

Glu Glu Lys Asp Gln Arg Arg Leu Phe Glu Gly Asn Ala Leu Leu Arg
    50                  55                  60

Arg Leu Val Arg Ile Gly Val Leu Asp Glu Thr Arg Met Lys Leu Asp
```

-continued

```
65                  70                  75                  80

Tyr Val Leu Gly Leu Lys Ile Glu Asp Phe Leu Glu Arg Arg Leu Gln
                85                  90                  95

Thr Gln Val Phe Lys Leu Gly Leu Ala Lys Ser Ile His His Ala Arg
            100                 105                 110

Val Leu Ile Arg Gln Arg His Ile Arg Val Arg Lys Gln Val Val Asn
        115                 120                 125

Ile Pro Ser Phe Ile Val Arg Leu Asp Ser Gln Lys His Ile Asp Phe
    130                 135                 140

Ser
145


<210> SEQ ID NO 13
<211> LENGTH: 26
<212> TYPE: DNA
<213> ORGANISM: Artificial sequence
<220> FEATURE:
<223> OTHER INFORMATION: degenerate primer
<220> FEATURE:
<221> NAME/KEY: misc_feature
<222> LOCATION: (18)..(18)
<223> OTHER INFORMATION: n = a, c, g or t

<400> SEQUENCE: 13

tcggtcttct cgaagacnta ygtkac                                          26


<210> SEQ ID NO 14
<211> LENGTH: 20
<212> TYPE: DNA
<213> ORGANISM: Artificial sequence
<220> FEATURE:
<223> OTHER INFORMATION: degenerative primer

<400> SEQUENCE: 14

ccgccgaagg gmgayttbag                                                 20


<210> SEQ ID NO 15
<211> LENGTH: 43
<212> TYPE: DNA
<213> ORGANISM: Artificial sequence
<220> FEATURE:
<223> OTHER INFORMATION: specific T7 primer

<400> SEQUENCE: 15

cgctaatacg actcactata ggcaggcgac cttatgaaaa ggc                       43


<210> SEQ ID NO 16
<211> LENGTH: 23
<212> TYPE: DNA
<213> ORGANISM: Artificial sequence
<220> FEATURE:
<223> OTHER INFORMATION: specific primer

<400> SEQUENCE: 16

cgagaagtca atatgcttct ggg                                             23


<210> SEQ ID NO 17
<211> LENGTH: 21
<212> TYPE: DNA
<213> ORGANISM: Artificial sequence
<220> FEATURE:
<223> OTHER INFORMATION: specific primer

<400> SEQUENCE: 17
```

-continued

```
caggcgacct tatgaaaagg c                                            21


<210> SEQ ID NO 18
<211> LENGTH: 45
<212> TYPE: DNA
<213> ORGANISM: Artificial sequence
<220> FEATURE:
<223> OTHER INFORMATION: specific T7 primer

<400> SEQUENCE: 18

cgctaatacg actcactata ggcgagaagt caatatgctt ctggg                 45


<210> SEQ ID NO 19
<211> LENGTH: 433
<212> TYPE: RNA
<213> ORGANISM: Blattella germanica

<400> SEQUENCE: 19

caggcgaccu uaugaaaagg cacgucuuga ucaggaguug aaaaucauag gagaauaugg     60

ucuuaggaac aaacgugaag uguggcgagu caaguauacc uuggcaaaaa uccguaaagc    120

ugccagagaa cuucugacuu uggaagagaa agaucagcgc agguuguuug aaggcaaugc    180

ucuucuucgu cgguuggugc guauuggagu guuggaugaa acccguauga agcuugauua    240

cgucuugggu uugaagauug aagauuucuu ggaacgacgu cuccaaacac aaguuuucaa    300

guuggggcuu gcaaaaucaa uccaucaugc ucgugugcug auccgucaaa gacauaucag    360

gguucguaag caggucguga auauuccaag cuucauugug agacuugauu cccagaagca    420

uauugacuuc ucg                                                       433


<210> SEQ ID NO 20
<211> LENGTH: 412
<212> TYPE: RNA
<213> ORGANISM: Blattella germanica

<400> SEQUENCE: 20

caggcgaccu uaugaaaagg cacgucuuga ucaggaguug aaaaucauag gagaauaugg     60

ucuuaggaac aaacgugaag uguggcgagu caaguauacc uuggcaaaaa uccguaaagc    120

ugccagagaa cuucugacuu uggaagagaa agaucagcgc agguuguuug aaggcaaugc    180

ucuucuucgu cgguuggugc guauuggagu guuggaugaa acccguauga agcuugauua    240

cgucuugggu uugaagauug aagauuucuu ggaacgacgu cuccaaacac aaguuuucaa    300

guuggggcuu gcaaaaucaa uccaucaugc ucgugugcug auccgucaaa gacauaucag    360

gguucguaag caggucguga auauuccaag cuucauugug agacuugauu cc            412


<210> SEQ ID NO 21
<211> LENGTH: 448
<212> TYPE: DNA
<213> ORGANISM: Blattella germanica

<400> SEQUENCE: 21

tgtgaaagga ccacgaggca ccttgaagcg cggtttcaag catcttgctt tagatatcca     60

cttggttcat ccaaggctcc tgaaggtgga aaaatggttt ggaacaaaga aggagttggc    120

agccgtgcgc accgtctgct ctcatattga gaacatgatt aaaggagtca caaagggttt    180

cctgtacaaa atgcgcgccg tgtatgccca tttccccatt aactgcgtaa ccacagaaaa    240

caattccgtt attgaagtgc gtaacttctt gggcgagaag ttcatccgca gagtgaagat    300

ggctccggga gtgaccgtca ccaattctcc aaagcagaaa gacgagctca ttctggaggg    360
```

caacgacatc gaggatgtat cgagatcagc cgcactcatc caacaatcga cgactgtgaa 420
gaacaaggac atccggaaat tccttgac 448

<210> SEQ ID NO 22
<211> LENGTH: 149
<212> TYPE: PRT
<213> ORGANISM: Blattella germanica

<400> SEQUENCE: 22

Val Lys Gly Pro Arg Gly Thr Leu Lys Arg Gly Phe Lys His Leu Ala
1 5 10 15

Leu Asp Ile His Leu Val His Pro Arg Leu Leu Lys Val Glu Lys Trp
20 25 30

Phe Gly Thr Lys Lys Glu Leu Ala Ala Val Arg Thr Val Cys Ser His
35 40 45

Ile Glu Asn Met Ile Lys Gly Val Thr Lys Gly Phe Leu Tyr Lys Met
50 55 60

Arg Ala Val Tyr Ala His Phe Pro Ile Asn Cys Val Thr Thr Glu Asn
65 70 75 80

Asn Ser Val Ile Glu Val Arg Asn Phe Leu Gly Glu Lys Phe Ile Arg
85 90 95

Arg Val Lys Met Ala Pro Gly Val Thr Val Thr Asn Ser Pro Lys Gln
100 105 110

Lys Asp Glu Leu Ile Leu Glu Gly Asn Asp Ile Glu Asp Val Ser Arg
115 120 125

Ser Ala Ala Leu Ile Gln Gln Ser Thr Thr Val Lys Asn Lys Asp Ile
130 135 140

Arg Lys Phe Leu Asp
145

<210> SEQ ID NO 23
<211> LENGTH: 20
<212> TYPE: DNA
<213> ORGANISM: Artificial sequence
<220> FEATURE:
<223> OTHER INFORMATION: forward degenerative primer
<220> FEATURE:
<221> NAME/KEY: misc_feature
<222> LOCATION: (12)..(13)
<223> OTHER INFORMATION: n = a, c, g or t

<400> SEQUENCE: 23
gtgaaggccc gnntggtgac 20

<210> SEQ ID NO 24
<211> LENGTH: 26
<212> TYPE: DNA
<213> ORGANISM: Artificial sequence
<220> FEATURE:
<223> OTHER INFORMATION: reverse degenerative primer

<400> SEQUENCE: 24
gtcgtcttct cdgahacrta vagacc 26

<210> SEQ ID NO 25
<211> LENGTH: 43
<212> TYPE: DNA
<213> ORGANISM: Artificial sequence
<220> FEATURE:
<223> OTHER INFORMATION: T7 primer forward

<400> SEQUENCE: 25
cgctaatacg actcactata gggtgaaagg accacgaggc acc 43

<210> SEQ ID NO 26
<211> LENGTH: 21
<212> TYPE: DNA
<213> ORGANISM: Artificial sequence
<220> FEATURE:
<223> OTHER INFORMATION: specific primer reverse

<400> SEQUENCE: 26
ccgtcaagga atttccggat g 21

<210> SEQ ID NO 27
<211> LENGTH: 21
<212> TYPE: DNA
<213> ORGANISM: Artificial sequence
<220> FEATURE:
<223> OTHER INFORMATION: specific primer forward

<400> SEQUENCE: 27
gtgaaaggac cacgaggcac c 21

<210> SEQ ID NO 28
<211> LENGTH: 43
<212> TYPE: DNA
<213> ORGANISM: Artificial sequence
<220> FEATURE:
<223> OTHER INFORMATION: specific T7 primer reverse

<400> SEQUENCE: 28
cgctaatacg actcactata ggccgtcaag gaatttccgg atg 43

<210> SEQ ID NO 29
<211> LENGTH: 449
<212> TYPE: RNA
<213> ORGANISM: Blattella germanica

<400> SEQUENCE: 29
gugaaaggac cacgaggcac cuugaagcgc gguuucaagc aucuugcuuu agauauccac 60
uugguucauc caaggcuccu gaagguggaa aaaugguuug gaacaaagaa ggaguuggca 120
gccgugcgca ccgucugcuc ucauauugag aacaugauua aaggagucac aaaggguuuc 180
cuguacaaaa ugcgcgccgu guaugcccau uuccccauua acugcguaac cacagaaaac 240
aauuccguua uugaagugcg uaacuucuug ggcgagaagu ucauccgcag agugaagaug 300
gcuccgggag ugaccgucac caauucucca aagcagaaag acgagcucau ucuggagggc 360
aacgacaucg aggauguauc gagaucagcc gcacucaucc aacaaucgac gacugugaag 420
aacaaggaca uccggaaauu ccuugacgg 449

<210> SEQ ID NO 30
<211> LENGTH: 428
<212> TYPE: RNA
<213> ORGANISM: Blattella germanica

<400> SEQUENCE: 30
gugaaaggac cacgaggcac cuugaagcgc gguuucaagc aucuugcuuu agauauccac 60
uugguucauc caaggcuccu gaagguggaa aaaugguuug gaacaaagaa ggaguuggca 120
gccgugcgca ccgucugcuc ucauauugag aacaugauua aaggagucac aaaggguuuc 180
cuguacaaaa ugcgcgccgu guaugcccau uuccccauua acugcguaac cacagaaaac 240

```
aauuccguua uugaagugcg uaacuucuug ggcgagaagu ucauccgcag agugaagaug    300

gcuccgggag ugaccgucac caauucucca aagcagaaag acgagcucau ucuggagggc    360

aacgacaucg aggauguauc gagaucagcc gcacucaucc aacaaucgac gacugugaag    420

aacaagga                                                              428


<210> SEQ ID NO 31
<211> LENGTH: 404
<212> TYPE: DNA
<213> ORGANISM: Blattella germanica

<400> SEQUENCE: 31

ggcttgatcc caatgaaata aacgaaattg caaataccaa ttccagacaa aatattcgta     60

aactgattaa agatggtctt atcatcaaga agcccgtagc tgtacactca agggcccgtg    120

ttcgcaagaa caccgaagca agaagaaaag gacgtcactg cggttttggc aaaaggaagg    180

gtacggcaaa tgcccgtatg ccacagaagg tcttgtggat taatcgcatg cgtgttctga    240

gaaggcttct caagaagtac agggaagcaa agaagatcga cagacatcta taccaccagc    300

tgtacatgaa ggccaagggt aacgtgttca agaacaagcg tgtcctgatg gagttcatcc    360

acaagaagaa ggctgagaag gccaggacaa agatgcttaa cgac                      404


<210> SEQ ID NO 32
<211> LENGTH: 134
<212> TYPE: PRT
<213> ORGANISM: Blattella germanica

<400> SEQUENCE: 32

Leu Asp Pro Asn Glu Ile Asn Glu Ile Ala Asn Thr Asn Ser Arg Gln
1               5                   10                  15

Asn Ile Arg Lys Leu Ile Lys Asp Gly Leu Ile Ile Lys Lys Pro Val
            20                  25                  30

Ala Val His Ser Arg Ala Arg Val Arg Lys Asn Thr Glu Ala Arg Arg
        35                  40                  45

Lys Gly Arg His Cys Gly Phe Gly Lys Arg Lys Gly Thr Ala Asn Ala
    50                  55                  60

Arg Met Pro Gln Lys Val Leu Trp Ile Asn Arg Met Arg Val Leu Arg
65                  70                  75                  80

Arg Leu Leu Lys Lys Tyr Arg Glu Ala Lys Lys Ile Asp Arg His Leu
                85                  90                  95

Tyr His Gln Leu Tyr Met Lys Ala Lys Gly Asn Val Phe Lys Asn Lys
            100                 105                 110

Arg Val Leu Met Glu Phe Ile His Lys Lys Lys Ala Glu Lys Ala Arg
        115                 120                 125

Thr Lys Met Leu Asn Asp
    130


<210> SEQ ID NO 33
<211> LENGTH: 26
<212> TYPE: DNA
<213> ORGANISM: Artificial sequence
<220> FEATURE:
<223> OTHER INFORMATION: degenerative primer forward

<400> SEQUENCE: 33

tgcgatgcgg caaraaraag gtbtgg                                           26
```

-continued

<210> SEQ ID NO 34
<211> LENGTH: 19
<212> TYPE: DNA
<213> ORGANISM: Artificial sequence
<220> FEATURE:
<223> OTHER INFORMATION: degenerative primer reverse

<400> SEQUENCE: 34
gtcggcgagc ytcrgcytg 19

<210> SEQ ID NO 35
<211> LENGTH: 46
<212> TYPE: DNA
<213> ORGANISM: Artificial sequence
<220> FEATURE:
<223> OTHER INFORMATION: specific T7 primer forward

<400> SEQUENCE: 35
cgctaatacg actcactata ggggcttgat cccaatgaaa taaacg 46

<210> SEQ ID NO 36
<211> LENGTH: 24
<212> TYPE: DNA
<213> ORGANISM: Artificial sequence
<220> FEATURE:
<223> OTHER INFORMATION: specific primer reverse

<400> SEQUENCE: 36
gtcgttaagc atctttgtcc tggc 24

<210> SEQ ID NO 37
<211> LENGTH: 24
<212> TYPE: DNA
<213> ORGANISM: Artificial sequence
<220> FEATURE:
<223> OTHER INFORMATION: specific primer forward

<400> SEQUENCE: 37
ggcttgatcc caatgaaata aacg 24

<210> SEQ ID NO 38
<211> LENGTH: 46
<212> TYPE: DNA
<213> ORGANISM: Artificial sequence
<220> FEATURE:
<223> OTHER INFORMATION: specific T7 primer reverse

<400> SEQUENCE: 38
cgctaatacg actcactata gggtcgttaa gcatctttgt cctggc 46

<210> SEQ ID NO 39
<211> LENGTH: 404
<212> TYPE: RNA
<213> ORGANISM: Blattella germanica

<400> SEQUENCE: 39
ggcuugaucc caaugaaaua aacgaaauug caaauaccaa uuccagacaa aauauucgua 60
aacugauuaa agauggucuu aucaucaaga agcccguagc uguacacuca agggcccgug 120
uucgcaagaa caccgaagca agaagaaaag gacgucacug cgguuuuggc aaaaggaagg 180
guacggcaaa ugcccguaug ccacagaagg ucuuguggau uaaucgcaug cguguucuga 240
gaaggcuucu caagaaguac agggaagcaa agaagaucga cagacaucua uaccaccagc 300
uguacaugaa ggccaagggu aacguguuca agaacaagcg uguccugaug gaguucaucc 360

-continued

```
acaagaagaa ggcugagaag gccaggacaa agaugcuuaa cgac                  404


<210> SEQ ID NO 40
<211> LENGTH: 383
<212> TYPE: RNA
<213> ORGANISM: Blattella germanica

<400> SEQUENCE: 40

ggcuugaucc caaugaaaua aacgaaauug caaauaccaa uuccagacaa aauauucgua    60

aacugauuaa agauggucuu aucaucaaga agcccguagc uguacacuca agggcccgug   120

uucgcaagaa caccgaagca agaagaaaag gacgucacug cgguuuuggc aaaaggaagg   180

guacggcaaa ugcccguaug ccacagaagg ucuuguggau uaaucgcaug cguguucuga   240

gaaggcuucu caagaaguac agggaagcaa agaagaucga cagacaucua uaccaccagc   300

uguacaugaa ggccaagggu aacguguuca agaacaagcg uguccugaug gaguucaucc   360

acaagaagaa ggcugagaag gcc                                           383


<210> SEQ ID NO 41
<211> LENGTH: 849
<212> TYPE: DNA
<213> ORGANISM: Blattella germanica

<400> SEQUENCE: 41

atggatgcca tcaagaagaa gatgcaggcg atgaagctgg agaaggacaa cgcgatggat    60

cgcgcccttc tctgcgaaca gcaggcccgc gacgccaaca tccgggccga gaaggctgag   120

gaggaggccc gatccctgca gaagaagatc cagcagattg agaatgatct tgatcagacc   180

atggagcagt tgatgcaagt caacgccaag ctggacgaga aggacaaggc cctgcagaat   240

gctgagagtg aggtcgctgc cctcaaccgc cgaatccaac tgctggagga ggatcttgag   300

aggtctgagg aacgtttggc cacagccacc gccaagttgg ctgaggcttc ccaggctgcc   360

gatgagtcag agcgagctcg taagattctt gaatccaaag gcctggcaga tgaagagcgt   420

atggatgctt tggagaacca gctgaaggaa gccaggttca tggctgagga agctgacaag   480

aaatatgatg aggtcgcacg taagttggct atggttgagg ccgacttgga aagagcagaa   540

gagcgtgccg agactggtga atccaagatt gtggagcttg aggaagaact gcgcgttgtc   600

ggcaacaacc tgaagtccct tgaggtgtct gaagagaagg ccaacctgcg tgaggaagag   660

tacaagcaac agattaagac tctgaatacc aggctaaagg aggctgaagc tcgtgctgag   720

ttcgctgaaa gatccgtgca gaaattgcag aaggaggttg acaggcttga ggatgaattg   780

gtacacgaga aggagaagta caagtacatt tgtgacgatc ttgatatgac tttcaccgaa   840

cttattggc                                                           849


<210> SEQ ID NO 42
<211> LENGTH: 283
<212> TYPE: PRT
<213> ORGANISM: Blattella germanica

<400> SEQUENCE: 42

Met Asp Ala Ile Lys Lys Lys Met Gln Ala Met Lys Leu Glu Lys Asp
1               5                   10                  15

Asn Ala Met Asp Arg Ala Leu Leu Cys Glu Gln Gln Ala Arg Asp Ala
            20                  25                  30

Asn Ile Arg Ala Glu Lys Ala Glu Glu Glu Ala Arg Ser Leu Gln Lys
        35                  40                  45
```

```
Lys Ile Gln Gln Ile Glu Asn Asp Leu Asp Gln Thr Met Glu Gln Leu
    50                  55                  60

Met Gln Val Asn Ala Lys Leu Asp Glu Lys Asp Lys Ala Leu Gln Asn
65                  70                  75                  80

Ala Glu Ser Glu Val Ala Ala Leu Asn Arg Arg Ile Gln Leu Leu Glu
                85                  90                  95

Glu Asp Leu Glu Arg Ser Glu Glu Arg Leu Ala Thr Ala Thr Ala Lys
            100                 105                 110

Leu Ala Glu Ala Ser Gln Ala Ala Asp Glu Ser Glu Arg Ala Arg Lys
        115                 120                 125

Ile Leu Glu Ser Lys Gly Leu Ala Asp Glu Glu Arg Met Asp Ala Leu
    130                 135                 140

Glu Asn Gln Leu Lys Glu Ala Arg Phe Met Ala Glu Glu Ala Asp Lys
145                 150                 155                 160

Lys Tyr Asp Glu Val Ala Arg Lys Leu Ala Met Val Glu Ala Asp Leu
                165                 170                 175

Glu Arg Ala Glu Glu Arg Ala Glu Thr Gly Glu Ser Lys Ile Val Glu
            180                 185                 190

Leu Glu Glu Glu Leu Arg Val Val Gly Asn Asn Leu Lys Ser Leu Glu
        195                 200                 205

Val Ser Glu Glu Lys Ala Asn Leu Arg Glu Glu Glu Tyr Lys Gln Gln
    210                 215                 220

Ile Lys Thr Leu Asn Thr Arg Leu Lys Glu Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Glu Leu Val His Glu Lys Glu Lys Tyr Lys Tyr Ile Cys Asp
            260                 265                 270

Asp Leu Asp Met Thr Phe Thr Glu Leu Ile Gly
        275                 280
```

<210> SEQ ID NO 43
<211> LENGTH: 27
<212> TYPE: DNA
<213> ORGANISM: Artificial sequence
<220> FEATURE:
<223> OTHER INFORMATION: specific primer forward

<400> SEQUENCE: 43
atggatgcca tcaagaagaa gatgcag 27

<210> SEQ ID NO 44
<211> LENGTH: 30
<212> TYPE: DNA
<213> ORGANISM: Artificial sequence
<220> FEATURE:
<223> OTHER INFORMATION: specific primer reverse

<400> SEQUENCE: 44
gccaataagt tcggtgaaag tcatatcaag 30

<210> SEQ ID NO 45
<211> LENGTH: 46
<212> TYPE: DNA
<213> ORGANISM: Artificial sequence
<220> FEATURE:
<223> OTHER INFORMATION: specific T7 primer forward

<400> SEQUENCE: 45

-continued

```
cgctaatacg actcactata ggatggatgc catcaagaag aagatg                46


<210> SEQ ID NO 46
<211> LENGTH: 46
<212> TYPE: DNA
<213> ORGANISM: Artificial sequence
<220> FEATURE:
<223> OTHER INFORMATION: specific T7 primer reverse

<400> SEQUENCE: 46

cgctaatacg actcactata gggccaataa gttcggtgaa agtcat                46


<210> SEQ ID NO 47
<211> LENGTH: 849
<212> TYPE: RNA
<213> ORGANISM: Blattella germanica

<400> SEQUENCE: 47

auggaugcca ucaagaagaa gaugcaggcg augaagcugg agaaggacaa cgcgauggau    60

cgcgcccuuc ucugcgaaca gcaggcccgc gacgccaaca uccgggccga gaaggcugag   120

gaggaggccc gaucccugca gaagaagauc cagcagauug agaaugaucu ugaucagacc   180

auggagcagu ugaugcaagu caacgccaag cuggacgaga aggacaaggc ccugcagaau   240

gcugagagug aggucgcugc ccucaaccgc cgaauccaac ugcuggagga ggaucuugag   300

aggucugagg aacguuuggc cacagccacc gccaaguugg cugaggcuuc ccaggcugcc   360

gaugagucag agcgagcucg uaagauucuu gaauccaaag gccuggcaga ugaagagcgu   420

auggaugcuu uggagaacca gcugaaggaa gccagguuca uggcugagga agcugacaag   480

aaauaugaug aggucgcacg uaaguuggcu augguugagg ccgacuugga aagagcagaa   540

gagcgugccg agacugguga auccaagauu guggagcuug aggaagaacu gcgcguuguc   600

ggcaacaacc ugaagucccu ugaggugucu gaagagaagg ccaaccugcg ugaggaagag   660

uacaagcaac agauuaagac ucugaauacc aggcuaaagg aggcugaagc ucgugcugag   720

uucgcugaaa gauccgugca gaaauugcag aaggagguug acaggcuuga ggaugaauug   780

guacacgaga aggagaagua caaguacauu ugugacgauc uugauaugac uuucaccgaa   840

cuuauuggc                                                           849


<210> SEQ ID NO 48
<211> LENGTH: 821
<212> TYPE: RNA
<213> ORGANISM: Blattella germanica

<400> SEQUENCE: 48

ccaucaagaa gaagaugcag gcgaugaagc uggagaagga caacgcgaug gaucgcgccc    60

uucucugcga acagcaggcc cgcgacgcca acauccgggc cgagaaggcu gaggaggagg   120

cccgaucccu gcagaagaag auccagcaga uugagaauga ucuugaucag accauggagc   180

aguugaugca agucaacgcc aagcuggacg agaaggacaa ggcccugcag aaugcugaga   240

gugaggucgc ugcccucaac cgccgaaucc aacugcugga ggaggaucuu gagaggucug   300

aggaacguuu ggccacagcc accgccaagu uggcugaggc uucccaggcu gccgaugagu   360

cagagcgagc ucguaagauu cuugaaucca aaggccuggc agaugaagag cguauggaug   420

cuuuggagaa ccagcugaag gaagccaggu ucauggcuga ggaagcugac aagaaauaug   480

augaggucgc acguaaguug gcuaugguug aggccgacuu ggaaagagca gaagagcgug   540

ccgagacugg ugaauccaag auuguggagc uugaggaaga acugcgcguu gucggcaaca   600
```

accugaaguc ccuugaggug ucugaagaga aggccaaccu gcgugaggaa gaguacaagc 660
aacagauuaa gacucugaau accaggcuaa aggaggcuga agcucgugcu gaguucgcug 720
aaagauccgu gcagaaauug cagaaggagg uugacaggcu ugaggaugaa uugguacacg 780
agaaggagaa guacaaguac auuugugacg aucuugauau g 821

<210> SEQ ID NO 49
<211> LENGTH: 1300
<212> TYPE: DNA
<213> ORGANISM: Blattella germanica

<400> SEQUENCE: 49
gctctggagc tcatattccc ttcgcagtat gtggatcagg tggacctcga ggtctacgac 60
aatgtttctg caggaaagta cacggtgggg ttgggacagg ctcgcatggg gttctgcacg 120
gacagggagg acatcaactc tctgtgtctc accgtcgtca gtcgactgat ggaacgatgg 180
agcatcccct actcgcaaat tgggcgcctg gaagtaggca ccgagaccct tctggacaag 240
tcgaagagcg tcaagactgt cctgatgcaa ctcttcaagg acaacacgga catcgagggc 300
gtggataccg tgaacgcctg ttacgggggc acctcggctc tcttcaatgc gatttcgtgg 360
gtggagtcca gctcctggga tggcaggtat gctcttgtgg tcgctgggga cattgctgtg 420
tatgctaaag gcagtgcgag gcccaccggt ggagcagggg ctgtggccat gctagtgggc 480
gccaatgctc ccctagtgtt cgacagagga gttcgttcat cacacatgca acatgcttat 540
gacttctaca aaccggatct gtcctcgctg taccccaccg tggatggcaa gctgtcaatt 600
caatgctatc ttagtgcctt agatcattgt tatcaactgt actgctccaa gatccagaaa 660
caacttggag agaagttcga tattgagcgg ctggatgcag ttctcttcca cgcgccttat 720
tgtaagttgg tgcagaagtc tcttgctcgc ctcgtcttga acgactttgt gcgggcatca 780
gaggaggagc ggacgactaa atactccagt ctggaagcac taaaaggcgt gaagctagaa 840
gatacgtact tcgaccgaga agttgagaaa gcagtcatga catacagcaa gaacatgttt 900
gaagagaaaa caaagccctc gctgttgctc gccaaccaag tcggcaacat gtacactcct 960
tcgctttacg gaggtttggt ctctctattg gtcagcaaga gcgcccagga gttggcaggg 1020
aagcgcgtgg ccttgttttc ttacggctcc ggactggcct cttccatgtt ctctctaaga 1080
atatcatcgg acgccagcgc gaaatcttct ctgcaacgcc tcgtctcgaa tctctcgcac 1140
atcaagccgc agctggatct gcgccacaag gtgtcaccag aggagtttgc acaaacgatg 1200
gagacgaggg aacacaacca ccacaaagct ccatacaccc cagagggctc gatcgacgtc 1260
ttgtttccag gaacttggta tctggagagc gtggacagcc 1300

<210> SEQ ID NO 50
<211> LENGTH: 433
<212> TYPE: PRT
<213> ORGANISM: Blattella germanica

<400> SEQUENCE: 50

Ala Leu Glu Leu Ile Phe Pro Ser Gln Tyr Val Asp Gln Val Asp Leu
1 5 10 15

Glu Val Tyr Asp Asn Val Ser Ala Gly Lys Tyr Thr Val Gly Leu Gly
20 25 30

Gln Ala Arg Met Gly Phe Cys Thr Asp Arg Glu Asp Ile Asn Ser Leu
35 40 45

Cys Leu Thr Val Val Ser Arg Leu Met Glu Arg Trp Ser Ile Pro Tyr

```
    50                  55                  60

Ser Gln Ile Gly Arg Leu Glu Val Gly Thr Glu Thr Leu Leu Asp Lys
65                  70                  75                  80

Ser Lys Ser Val Lys Thr Val Leu Met Gln Leu Phe Lys Asp Asn Thr
                85                  90                  95

Asp Ile Glu Gly Val Asp Thr Val Asn Ala Cys Tyr Gly Gly Thr Ser
            100                 105                 110

Ala Leu Phe Asn Ala Ile Ser Trp Val Glu Ser Ser Ser Trp Asp Gly
        115                 120                 125

Arg Tyr Ala Leu Val Val Ala Gly Asp Ile Ala Val Tyr Ala Lys Gly
    130                 135                 140

Ser Ala Arg Pro Thr Gly Gly Ala Gly Ala Val Ala Met Leu Val Gly
145                 150                 155                 160

Ala Asn Ala Pro Leu Val Phe Asp Arg Gly Val Arg Ser Ser His Met
                165                 170                 175

Gln His Ala Tyr Asp Phe Tyr Lys Pro Asp Leu Ser Ser Leu Tyr Pro
            180                 185                 190

Thr Val Asp Gly Lys Leu Ser Ile Gln Cys Tyr Leu Ser Ala Leu Asp
        195                 200                 205

His Cys Tyr Gln Leu Tyr Cys Ser Lys Ile Gln Lys Gln Leu Gly Glu
    210                 215                 220

Lys Phe Asp Ile Glu Arg Leu Asp Ala Val Leu Phe His Ala Pro Tyr
225                 230                 235                 240

Cys Lys Leu Val Gln Lys Ser Leu Ala Arg Leu Val Leu Asn Asp Phe
                245                 250                 255

Val Arg Ala Ser Glu Glu Glu Arg Thr Thr Lys Tyr Ser Ser Leu Glu
            260                 265                 270

Ala Leu Lys Gly Val Lys Leu Glu Asp Thr Tyr Phe Asp Arg Glu Val
        275                 280                 285

Glu Lys Ala Val Met Thr Tyr Ser Lys Asn Met Phe Glu Glu Lys Thr
    290                 295                 300

Lys Pro Ser Leu Leu Leu Ala Asn Gln Val Gly Asn Met Tyr Thr Pro
305                 310                 315                 320

Ser Leu Tyr Gly Gly Leu Val Ser Leu Leu Val Ser Lys Ser Ala Gln
                325                 330                 335

Glu Leu Ala Gly Lys Arg Val Ala Leu Phe Ser Tyr Gly Ser Gly Leu
            340                 345                 350

Ala Ser Ser Met Phe Ser Leu Arg Ile Ser Ser Asp Ala Ser Ala Glu
        355                 360                 365

Ser Pro Leu Gln Arg Leu Val Ser Asn Leu Ser His Ile Lys Pro Gln
    370                 375                 380

Leu Asp Leu Arg His Lys Val Ser Pro Glu Glu Phe Ala Gln Thr Met
385                 390                 395                 400

Glu Thr Arg Glu His Asn His His Lys Ala Pro Tyr Thr Pro Glu Gly
                405                 410                 415

Ser Ile Asp Val Leu Phe Pro Gly Thr Trp Tyr Leu Glu Ser Val Asp
            420                 425                 430

Ser
```

<210> SEQ ID NO 51
<211> LENGTH: 25
<212> TYPE: DNA
<213> ORGANISM: Artificial sequence
<220> FEATURE:

<223> OTHER INFORMATION: specific primer forward

<400> SEQUENCE: 51
gctctggagc tcatattccc ttcgc 25

<210> SEQ ID NO 52
<211> LENGTH: 24
<212> TYPE: DNA
<213> ORGANISM: Artificial sequence
<220> FEATURE:
<223> OTHER INFORMATION: specific primer reverse

<400> SEQUENCE: 52
ggctgtccac gctctccaga tacc 24

<210> SEQ ID NO 53
<211> LENGTH: 45
<212> TYPE: DNA
<213> ORGANISM: Artificial sequence
<220> FEATURE:
<223> OTHER INFORMATION: specific T7 primer forward

<400> SEQUENCE: 53
cgctaatacg actcactata gggctctgga gctcatattc ccttc 45

<210> SEQ ID NO 54
<211> LENGTH: 41
<212> TYPE: DNA
<213> ORGANISM: Artificial sequence
<220> FEATURE:
<223> OTHER INFORMATION: specific T7 primer reverse

<400> SEQUENCE: 54
cgctaatacg actcactata ggggctgtcc acgctctcca g 41

<210> SEQ ID NO 55
<211> LENGTH: 1300
<212> TYPE: RNA
<213> ORGANISM: Blattella germanica

<400> SEQUENCE: 55
gcucuggagc ucauauuccc uucgcaguau guggaucagg uggaccucga ggucuacgac 60
aauguuucug caggaaagua cacggugggg uugggacagg cucgcauggg guucugcacg 120
gacagggagg acaucaacuc ucugugucuc accgucguca gucgacugau ggaacgaugg 180 agcaucccu acucgcaaau ugggcgccug gaaguaggca ccgagacccu ucuggacaag 240
ucgaagagcg ucaagacugu ccugaugcaa cucuucaagg acaacacgga caucgagggc 300
guggauaccg ugaacgccug uuacgggggc accucggcuc ucuucaaugc gauuucgugg 360
guggagucca gcuccuggga uggcagguau gcucuugugg ucgcugggga cauugcugug 420
uaugcuaaag gcagugcgag gcccaccggu ggagcagggg cuguggccau gcuagugggc 480
gccaaugcuc cccuaguguu cgacagagga guucguucau cacacaugca acaugcuuau 540
gacuucuaca aaccggaucu guccucgcug uaccccaccg uggauggcaa gcugucaauu 600
caaugcuauc uuagugccuu agaucauugu uaucaacugu acugcuccaa gauccagaaa 660
caacuuggag agaaguucga uauugagcgg cuggaugcag uucucuucca cgcgccuuau 720
uguaaguugg ugcagaaguc ucuugcucgc cucgucuuga acgacuuugu gcgggcauca 780
gaggaggagc ggacgacuaa auacuccagu cuggaagcac uaaaaggcgu gaagcuagaa 840
gauacguacu ucgaccgaga aguugagaaa gcagucauga cauacagcaa gaacauguuu 900

-continued gaagagaaaa caaagcccuc gcuguugcuc gccaaccaag ucggcaacau guacacuccu 960
ucgcuuuacg gagguuuggu cucucuauug gucagcaaga gcgcccagga guuggcaggg 1020
aagcgcgugg ccuuguuuuc uuacggcucc ggacuggccu cuuccauguu cucucuaaga 1080
auaucaucgg acgccagcgc gaaaucuucu cugcaacgcc ucgucucgaa ucucucgcac 1140
aucaagccgc agcuggaucu gcgccacaag gugucaccag aggaguuugc acaaacgaug 1200
gagacgaggg aacacaacca ccacaaagcu ccauacaccc cagagggcuc gaucgacguc 1260
uuguuuccag gaacuuggua ucuggagagc guggacagcc 1300

<210> SEQ ID NO 56
<211> LENGTH: 1279
<212> TYPE: RNA
<213> ORGANISM: Blattella germanica

<400> SEQUENCE: 56
gcucuggagc ucauauuccc uucgcaguau guggaucagg uggaccucga ggucuacgac 60
aauguuucug caggaaagua cacggugggg uugggacagg cucgcauggg guucugcacg 120
gacagggagg acaucaacuc ucugugucuc accgucguca gucgacugau ggaacgaugg 180 agcaucccccu acucgcaaau ugggcgccug gaaguaggca ccgagacccu ucuggacaag 240
ucgaagagcg ucaagacugu ccugaugcaa cucuucaagg acaacacgga caucgagggc 300
guggauaccg ugaacgccug uuacgggggc accucggcuc ucuucaaugc gauuucgugg 360
guggagucca gcuccuggga uggcagguau gcucuugugg ucgcugggga cauugcugug 420
uaugcuaaag gcagugcgag gcccaccggu ggagcagggg cuguggccau gcuagugggc 480
gccaaugcuc cccuaguguu cgacagagga guucguucau cacacaugca acaugcuuau 540
gacuucuaca aaccggaucu guccucgcug uaccccaccg uggauggcaa gcugucaauu 600
caaugcuauc uuagugccuu agaucauugu uaucaacugu acugcuccaa gauccagaaa 660
caacuuggag agaaguucga uauugagcgg cuggaugcag uucucuucca cgcgccuuau 720
uguaaguugg ugcagaaguc ucuugcucgc cucgucuuga acgacuuugu gcgggcauca 780
gaggaggagc ggacgacuaa auacuccagu cuggaagcac uaaaaggcgu gaagcuagaa 840
gauacguacu ucgaccgaga aguugagaaa gcagucauga cauacagcaa gaacauguuu 900
gaagagaaaa caaagcccuc gcuguugcuc gccaaccaag ucggcaacau guacacuccu 960
ucgcuuuacg gagguuuggu cucucuauug gucagcaaga gcgcccagga guuggcaggg 1020
aagcgcgugg ccuuguuuuc uuacggcucc ggacuggccu cuuccauguu cucucuaaga 1080
auaucaucgg acgccagcgc gaaaucuucu cugcaacgcc ucgucucgaa ucucucgcac 1140
aucaagccgc agcuggaucu gcgccacaag gugucaccag aggaguuugc acaaacgaug 1200
gagacgaggg aacacaacca ccacaaagcu ccauacaccc cagagggcuc gaucgacguc 1260
uuguuuccag gaacuuggu 1279

<210> SEQ ID NO 57
<211> LENGTH: 451
<212> TYPE: DNA
<213> ORGANISM: Blattella germanica

<400> SEQUENCE: 57
gaggcccaga gcaagagagg tatcctcact ctgaagtacc ccattgaaca tggaatcatc 60
accaactggg atgacatgga gaagatctgg catcacacct tctacaatga actccgagtg 120

-continued

```
gctccagagg aacacccaat cctgctgact gaggctcccc tgaacccaaa ggccaacagg    180

gagaagatga ctcaaatcat gtttgagacc ttcaacaccc ccgccatgta tgttgccatc    240

caggccgtgc tgtccctcta cgcttccggc cgtaccactg gtattgtgct ggactctggt    300

gacggcgtct cccacaccgt acccatctat gaaggttacg cattgcccca tgccatcctg    360

cgtctggact tggccggccg tgacttgact gactacctga tgaagatcct gaccgagcgt    420

ggctacagct tcacaactac agcagagcga g                                   451
```

```
<210> SEQ ID NO 58
<211> LENGTH: 150
<212> TYPE: PRT
<213> ORGANISM: Blattella germanica

<400> SEQUENCE: 58

Glu Ala Gln Ser Lys Arg Gly Ile Leu Thr Leu Lys Tyr Pro Ile Glu
1               5                   10                  15

His Gly Ile Ile Thr Asn Trp Asp Asp Met Glu Lys Ile Trp His His
            20                  25                  30

Thr Phe Tyr Asn Glu Leu Arg Val Ala Pro Glu Glu His Pro Ile Leu
        35                  40                  45

Leu Thr Glu Ala Pro Leu Asn Pro Lys Ala Asn Arg Glu Lys Met Thr
    50                  55                  60

Gln Ile Met Phe Glu Thr Phe Asn Thr Pro Ala Met Tyr Val Ala Ile
65                  70                  75                  80

Gln Ala Val Leu Ser Leu Tyr Ala Ser Gly Arg Thr Thr Gly Ile Val
                85                  90                  95

Leu Asp Ser Gly Asp Gly Val Ser His Thr Val Pro Ile Tyr Glu Gly
            100                 105                 110

Tyr Ala Leu Pro His Ala Ile Leu Arg Leu Asp Leu Ala Gly Arg Asp
        115                 120                 125

Leu Thr Asp Tyr Leu Met Lys Ile Leu Thr Glu Arg Gly Tyr Ser Phe
    130                 135                 140

Thr Thr Thr Ala Glu Arg
145                 150
```

```
<210> SEQ ID NO 59
<211> LENGTH: 25
<212> TYPE: DNA
<213> ORGANISM: Artificial sequence
<220> FEATURE:
<223> OTHER INFORMATION: degenerative primer forward

<400> SEQUENCE: 59

gaggcccaga gcaagagagg tatcc                                           25
```

```
<210> SEQ ID NO 60
<211> LENGTH: 26
<212> TYPE: DNA
<213> ORGANISM: Artificial sequence
<220> FEATURE:
<223> OTHER INFORMATION: degenerative primer reverse

<400> SEQUENCE: 60

ctcgctctgc tgtagttgtg aagctg                                          26
```

```
<210> SEQ ID NO 61
<211> LENGTH: 42
<212> TYPE: DNA
<213> ORGANISM: Artificial sequence
```

<220> FEATURE:
<223> OTHER INFORMATION: specific T7 primer forward

<400> SEQUENCE: 61
cgctaatacg actcactata gggaggccca gagcaagaga gg 42

<210> SEQ ID NO 62
<211> LENGTH: 48
<212> TYPE: DNA
<213> ORGANISM: Artificial sequence
<220> FEATURE:
<223> OTHER INFORMATION: specific T7 primer reverse

<400> SEQUENCE: 62
cgctaatacg actcactata ggtctgctgt agttgtgaag ctgtagcc 48

<210> SEQ ID NO 63
<211> LENGTH: 446
<212> TYPE: RNA
<213> ORGANISM: Blattella germanica

<400> SEQUENCE: 63
gaggcccaga gcaagagagg uauccucacu cugaaguacc ccauugaaca uggaaucauc 60
accaacuggg augacaugga gaagaucugg caucacaccu ucuacaauga acuccgagug 120
gcuccagagg aacacccaau ccugcugacu gaggcucccc ugaacccaaa ggccaacagg 180
gagaagauga cucaaaucau guuugagacc uucaacaccc ccgccaugua uguugccauc 240
caggccgugc ugucccucua cgcuuccggc cguaccacug guauugugcu ggacucuggu 300
gacggcgucu cccacaccgu acccaucuau gaagguuacg cauugcccca ugccauccug 360
cgucuggacu uggccggccg ugacuugacu gacuaccuga ugaagauccu gaccgagcgu 420
ggcuacagcu ucacaacuac agcaga 446

<210> SEQ ID NO 64
<211> LENGTH: 108
<212> TYPE: RNA
<213> ORGANISM: Blattella germanica

<400> SEQUENCE: 64
uggcaucaca ccuucuacaa ugaacuccga guggcuccag aggaacaccc aauccugcug 60
acugaggcuc cccugaaccc aaaggccaac agggagaaga ugacucaa 108

<210> SEQ ID NO 65
<211> LENGTH: 50
<212> TYPE: DNA
<213> ORGANISM: Artificial sequence
<220> FEATURE:
<223> OTHER INFORMATION: Synthetic fragment

<400> SEQUENCE: 65
tatgctccaa gaccaagcac aggacctcac aagttacgag agagtctgcc 50

<210> SEQ ID NO 66
<211> LENGTH: 50
<212> TYPE: DNA
<213> ORGANISM: Artificial sequence
<220> FEATURE:
<223> OTHER INFORMATION: Synthetic fragment

<400> SEQUENCE: 66
cttgggtcgt gttggaactg tagttaatcg agaacgtcat cctggttcct 50

-continued

<210> SEQ ID NO 67
<211> LENGTH: 250
<212> TYPE: DNA
<213> ORGANISM: Artificial sequence
<220> FEATURE:
<223> OTHER INFORMATION: Concatemer

<400> SEQUENCE: 67
tatgctccaa gaccaagcac aggacctcac aagttacgag agagtctgcc tatgctccaa 60
gaccaagcac aggacctcac aagttacgag agagtctgcc tatgctccaa gaccaagcac 120
aggacctcac aagttacgag agagtctgcc tatgctccaa gaccaagcac aggacctcac 180
aagttacgag agagtctgcc tatgctccaa gaccaagcac aggacctcac aagttacgag 240
agagtctgcc 250

<210> SEQ ID NO 68
<211> LENGTH: 250
<212> TYPE: DNA
<213> ORGANISM: Artificial sequence
<220> FEATURE:
<223> OTHER INFORMATION: Concatemer

<400> SEQUENCE: 68
cttgggtcgt gttggaactg tagttaatcg agaacgtcat cctggttcct cttgggtcgt 60
gttggaactg tagttaatcg agaacgtcat cctggttcct cttgggtcgt gttggaactg 120
tagttaatcg agaacgtcat cctggttcct cttgggtcgt gttggaactg tagttaatcg 180
agaacgtcat cctggttcct cttgggtcgt gttggaactg tagttaatcg agaacgtcat 240
cctggttcct 250

<210> SEQ ID NO 69
<211> LENGTH: 100
<212> TYPE: DNA
<213> ORGANISM: Artificial sequenc
<220> FEATURE:
<223> OTHER INFORMATION: Synthetic fragment

<400> SEQUENCE: 69
gctgaaatat gcattaacca actgtgaggt taagaaaatt gttatgcagc gccttattaa 60
ggttgatgga aaagtcagaa cagaccccaa ctatccagct 100

<210> SEQ ID NO 70
<211> LENGTH: 300
<212> TYPE: DNA
<213> ORGANISM: Artificial sequence
<220> FEATURE:
<223> OTHER INFORMATION: Concatemer

<400> SEQUENCE: 70
gctgaaatat gcattaacca actgtgaggt taagaaaatt gttatgcagc gccttattaa 60
ggttgatgga aaagtcagaa cagaccccaa ctatccagct gctgaaatat gcattaacca 120
actgtgaggt taagaaaatt gttatgcagc gccttattaa ggttgatgga aaagtcagaa 180
cagaccccaa ctatccagct gctgaaatat gcattaacca actgtgaggt taagaaaatt 240
gttatgcagc gccttattaa ggttgatgga aaagtcagaa cagaccccaa ctatccagct 300

<210> SEQ ID NO 71
<211> LENGTH: 23
<212> TYPE: DNA
<213> ORGANISM: Blattella germanica -continued

<400> SEQUENCE: 71
aaggcatgga tgttggacaa gct 23

<210> SEQ ID NO 72
<211> LENGTH: 23
<212> TYPE: DNA
<213> ORGANISM: Blattella germanica

<400> SEQUENCE: 72
gcatggatgt tggacaagct cgg 23

<210> SEQ ID NO 73
<211> LENGTH: 26
<212> TYPE: DNA
<213> ORGANISM: Blattella germanica

<400> SEQUENCE: 73
attaaggttg atggaaaagt cagaac 26

<210> SEQ ID NO 74
<211> LENGTH: 32
<212> TYPE: DNA
<213> ORGANISM: Blattella germanica

<400> SEQUENCE: 74
cccaactatc cagctggttt tatggatgtt gt 32

<210> SEQ ID NO 75
<211> LENGTH: 32
<212> TYPE: DNA
<213> ORGANISM: Blattella germanica

<400> SEQUENCE: 75
gctggtttta tggatgttgt tacaattgaa aa 32

<210> SEQ ID NO 76
<211> LENGTH: 26
<212> TYPE: DNA
<213> ORGANISM: Blattella germanica

<400> SEQUENCE: 76
attgaaaaaa ctggagaatt tttccg 26

<210> SEQ ID NO 77
<211> LENGTH: 23
<212> TYPE: DNA
<213> ORGANISM: Blattella germanica

<400> SEQUENCE: 77
ggtaatctct gtatgattac tgg 23

<210> SEQ ID NO 78
<211> LENGTH: 26
<212> TYPE: DNA
<213> ORGANISM: Blattella germanica

<400> SEQUENCE: 78
cgtcatcctg gttcctttga cattgt 26

<210> SEQ ID NO 79
<211> LENGTH: 22
<212> TYPE: DNA

<213> ORGANISM: Blattella germanica

<400> SEQUENCE: 79
ttaaagattc acaaggacac ac 22

<210> SEQ ID NO 80
<211> LENGTH: 26
<212> TYPE: DNA
<213> ORGANISM: Blattella germanica

<400> SEQUENCE: 80
aaaatccgta aagctgccag agaact 26

<210> SEQ ID NO 81
<211> LENGTH: 23
<212> TYPE: DNA
<213> ORGANISM: Blattella germanica

<400> SEQUENCE: 81
cgtaaagctg ccagagaact tct 23

<210> SEQ ID NO 82
<211> LENGTH: 24
<212> TYPE: DNA
<213> ORGANISM: Blattella germanica

<400> SEQUENCE: 82
aggttgtttg aaggcaatgc tctt 24

<210> SEQ ID NO 83
<211> LENGTH: 21
<212> TYPE: DNA
<213> ORGANISM: Blattella germanica

<400> SEQUENCE: 83
cgtattggag tgttggatga a 21

<210> SEQ ID NO 84
<211> LENGTH: 21
<212> TYPE: DNA
<213> ORGANISM: Blattella germanica

<400> SEQUENCE: 84
ccgtatgaag cttgattacg t 21

<210> SEQ ID NO 85
<211> LENGTH: 29
<212> TYPE: DNA
<213> ORGANISM: Blattella germanica

<400> SEQUENCE: 85
ttgggtttga agattgaaga tttcttgga 29

<210> SEQ ID NO 86
<211> LENGTH: 21
<212> TYPE: DNA
<213> ORGANISM: Blattella germanica

<400> SEQUENCE: 86
aagattgaag atttcttgga a 21

<210> SEQ ID NO 87
<211> LENGTH: 23

-continued

<212> TYPE: DNA
<213> ORGANISM: Blattella germanica

<400> SEQUENCE: 87
aggaacaaac gtgaagtgtg gcg 23

<210> SEQ ID NO 88
<211> LENGTH: 21
<212> TYPE: DNA
<213> ORGANISM: Blattella germanica

<400> SEQUENCE: 88
tgctctcata ttgagaacat g 21

<210> SEQ ID NO 89
<211> LENGTH: 21
<212> TYPE: DNA
<213> ORGANISM: Blattella germanica

<400> SEQUENCE: 89
aagggtttcc tgtacaaaat g 21

<210> SEQ ID NO 90
<211> LENGTH: 23
<212> TYPE: DNA
<213> ORGANISM: Blattella germanica

<400> SEQUENCE: 90
gccgtgtatg cccatttccc cat 23

<210> SEQ ID NO 91
<211> LENGTH: 26
<212> TYPE: DNA
<213> ORGANISM: Blattella germanica

<400> SEQUENCE: 91
tatgcccatt tccccattaa ctgcgt 26

<210> SEQ ID NO 92
<211> LENGTH: 22
<212> TYPE: DNA
<213> ORGANISM: Blattella germanica

<400> SEQUENCE: 92
cgtaacttct tgggcgagaa gt 22

<210> SEQ ID NO 93
<211> LENGTH: 24
<212> TYPE: DNA
<213> ORGANISM: Blattella germanica

<400> SEQUENCE: 93
aaatggtttg gaacaaagaa ggag 24

<210> SEQ ID NO 94
<211> LENGTH: 23
<212> TYPE: DNA
<213> ORGANISM: Blattella germanica

<400> SEQUENCE: 94
gatcccaatg aaataaacga aat 23

<210> SEQ ID NO 95

```
<211> LENGTH: 26
<212> TYPE: DNA
<213> ORGANISM: Blattella germanica

<400> SEQUENCE: 95

aatgaaataa acgaaattgc aaatac                                          26


<210> SEQ ID NO 96
<211> LENGTH: 23
<212> TYPE: DNA
<213> ORGANISM: Blattella germanica

<400> SEQUENCE: 96

ggttttggca aaaggaaggg tac                                             23


<210> SEQ ID NO 97
<211> LENGTH: 23
<212> TYPE: DNA
<213> ORGANISM: Blattella germanica

<400> SEQUENCE: 97

gcaaatgccc gtatgccaca gaa                                             23


<210> SEQ ID NO 98
<211> LENGTH: 22
<212> TYPE: DNA
<213> ORGANISM: Blattella germanica

<400> SEQUENCE: 98

aatgcccgta tgccacagaa gg                                              22


<210> SEQ ID NO 99
<211> LENGTH: 23
<212> TYPE: DNA
<213> ORGANISM: Blattella germanica

<400> SEQUENCE: 99

aagaagtaca gggaagcaaa gaa                                             23


<210> SEQ ID NO 100
<211> LENGTH: 23
<212> TYPE: DNA
<213> ORGANISM: Blattella germanica

<400> SEQUENCE: 100

aagaagatcg acagacatct ata                                             23


<210> SEQ ID NO 101
<211> LENGTH: 27
<212> TYPE: DNA
<213> ORGANISM: Blattella germanica

<400> SEQUENCE: 101

caagggtaac gtgttcaaga acaagcg                                         27


<210> SEQ ID NO 102
<211> LENGTH: 32
<212> TYPE: DNA
<213> ORGANISM: Blattella germanica

<400> SEQUENCE: 102

aagggtaacg tgttcaagaa caagcgtgtc ct                                   32
```

<210> SEQ ID NO 103
<211> LENGTH: 31
<212> TYPE: DNA
<213> ORGANISM: Blattella germanica

<400> SEQUENCE: 103
gtgttcaaga acaagcgtgt cctgatggag t 31

<210> SEQ ID NO 104
<211> LENGTH: 30
<212> TYPE: DNA
<213> ORGANISM: Blattella germanica

<400> SEQUENCE: 104
tgatggagtt catccacaag aagaaggctg 30

<210> SEQ ID NO 105
<211> LENGTH: 25
<212> TYPE: DNA
<213> ORGANISM: Blattella germanica

<400> SEQUENCE: 105
catccacaag aagaaggctg agaag 25

<210> SEQ ID NO 106
<211> LENGTH: 22
<212> TYPE: DNA
<213> ORGANISM: Blattella germanica

<400> SEQUENCE: 106
acaagaagaa ggctgagaag gc 22

<210> SEQ ID NO 107
<211> LENGTH: 26
<212> TYPE: DNA
<213> ORGANISM: Blattella germanica

<400> SEQUENCE: 107
accaattcca gacaaaatat tcgtaa 26

<210> SEQ ID NO 108
<211> LENGTH: 25
<212> TYPE: DNA
<213> ORGANISM: Blattella germanica

<400> SEQUENCE: 108
gaagaaggct gagaaggcca ggaca 25

<210> SEQ ID NO 109
<211> LENGTH: 54
<212> TYPE: DNA
<213> ORGANISM: Blattella germanica

<400> SEQUENCE: 109
atggatgcca tcaagaagaa gatgcaggcg atgaagctgg agaaggacaa cgcg 54

<210> SEQ ID NO 110
<211> LENGTH: 25
<212> TYPE: DNA
<213> ORGANISM: Blattella germanica

<400> SEQUENCE: 110
gggccgagaa ggctgaggag gaggc 25

<210> SEQ ID NO 111
<211> LENGTH: 38
<212> TYPE: DNA
<213> ORGANISM: Blattella germanica

<400> SEQUENCE: 111
tccctgcaga agaagatcca gcagattgag aatgatct 38

<210> SEQ ID NO 112
<211> LENGTH: 22
<212> TYPE: DNA
<213> ORGANISM: Blattella germanica

<400> SEQUENCE: 112
tgatgcaagt caacgccaag ct 22

<210> SEQ ID NO 113
<211> LENGTH: 23
<212> TYPE: DNA
<213> ORGANISM: Blattella germanica

<400> SEQUENCE: 113
atgcaagtca acgccaagct gga 23

<210> SEQ ID NO 114
<211> LENGTH: 35
<212> TYPE: DNA
<213> ORGANISM: Blattella germanica

<400> SEQUENCE: 114
gtcaacgcca agctggacga gaaggacaag gccct 35

<210> SEQ ID NO 115
<211> LENGTH: 23
<212> TYPE: DNA
<213> ORGANISM: Blattella germanica

<400> SEQUENCE: 115
gagaaggaca aggccctgca gaa 23

<210> SEQ ID NO 116
<211> LENGTH: 26
<212> TYPE: DNA
<213> ORGANISM: Blattella germanica

<400> SEQUENCE: 116
aaccgccgaa tccaactgct ggagga 26

<210> SEQ ID NO 117
<211> LENGTH: 38
<212> TYPE: DNA
<213> ORGANISM: Blattella germanica

<400> SEQUENCE: 117
gcgatgaagc tggagaagga caacgcgatg gatcgcgc 38

<210> SEQ ID NO 118
<211> LENGTH: 23
<212> TYPE: DNA
<213> ORGANISM: Blattella germanica

<400> SEQUENCE: 118
tctgaggaac gtttggccac agc 23

<210> SEQ ID NO 119
<211> LENGTH: 22
<212> TYPE: DNA
<213> ORGANISM: Blattella germanica

<400> SEQUENCE: 119
tggcagatga agagcgtatg ga 22

<210> SEQ ID NO 120
<211> LENGTH: 21
<212> TYPE: DNA
<213> ORGANISM: Blattella germanica

<400> SEQUENCE: 120
gatgaagagc gtatggatgc t 21

<210> SEQ ID NO 121
<211> LENGTH: 23
<212> TYPE: DNA
<213> ORGANISM: Blattella germanica

<400> SEQUENCE: 121
gctttggaga accagctgaa gga 23

<210> SEQ ID NO 122
<211> LENGTH: 21
<212> TYPE: DNA
<213> ORGANISM: Blattella germanica

<400> SEQUENCE: 122
gagaaccagc tgaaggaagc c 21

<210> SEQ ID NO 123
<211> LENGTH: 21
<212> TYPE: DNA
<213> ORGANISM: Blattella germanica

<400> SEQUENCE: 123
cagctgaagg aagccaggtt c 21

<210> SEQ ID NO 124
<211> LENGTH: 29
<212> TYPE: DNA
<213> ORGANISM: Blattella germanica

<400> SEQUENCE: 124
ttcatggctg aggaagctga caagaaata 29

<210> SEQ ID NO 125
<211> LENGTH: 23
<212> TYPE: DNA
<213> ORGANISM: Blattella germanica

<400> SEQUENCE: 125
gctgacaaga aatatgatga ggt 23

<210> SEQ ID NO 126
<211> LENGTH: 23
<212> TYPE: DNA
<213> ORGANISM: Blattella germanica

<400> SEQUENCE: 126
gacaagaaat atgatgaggt cgc 23

<210> SEQ ID NO 127
<211> LENGTH: 29
<212> TYPE: DNA
<213> ORGANISM: Blattella germanica

<400> SEQUENCE: 127
atggttgagg ccgacttgga aagagcaga 29

<210> SEQ ID NO 128
<211> LENGTH: 23
<212> TYPE: DNA
<213> ORGANISM: Blattella germanica

<400> SEQUENCE: 128
gccgacttgg aaagagcaga aga 23

<210> SEQ ID NO 129
<211> LENGTH: 27
<212> TYPE: DNA
<213> ORGANISM: Blattella germanica

<400> SEQUENCE: 129
cgacttggaa agagcagaag agcgtgc 27

<210> SEQ ID NO 130
<211> LENGTH: 22
<212> TYPE: DNA
<213> ORGANISM: Blattella germanica

<400> SEQUENCE: 130
ccaagattgt ggagcttgag ga 22

<210> SEQ ID NO 131
<211> LENGTH: 23
<212> TYPE: DNA
<213> ORGANISM: Blattella germanica

<400> SEQUENCE: 131
aagattgtgg agcttgagga aga 23

<210> SEQ ID NO 132
<211> LENGTH: 34
<212> TYPE: DNA
<213> ORGANISM: Blattella germanica

<400> SEQUENCE: 132
tggatcgcgc ccttctctgc gaacagcagg cccg 34

<210> SEQ ID NO 133
<211> LENGTH: 29
<212> TYPE: DNA
<213> ORGANISM: Blattella germanica

<400> SEQUENCE: 133
attgtggagc ttgaggaaga actgcgcgt 29

<210> SEQ ID NO 134
<211> LENGTH: 21
<212> TYPE: DNA
<213> ORGANISM: Blattella germanica

<400> SEQUENCE: 134
ctgcgcgttg tcggcaacaa c 21

<210> SEQ ID NO 135
<211> LENGTH: 35
<212> TYPE: DNA
<213> ORGANISM: Blattella germanica

<400> SEQUENCE: 135
cgcgttgtcg gcaacaacct gaagtccctt gaggt 35

<210> SEQ ID NO 136
<211> LENGTH: 59
<212> TYPE: DNA
<213> ORGANISM: Blattella germanica

<400> SEQUENCE: 136
gttgtcggca acaacctgaa gtcccttgag gtgtctgaag agaaggccaa cctgcgtga 59

<210> SEQ ID NO 137
<211> LENGTH: 21
<212> TYPE: DNA
<213> ORGANISM: Blattella germanica

<400> SEQUENCE: 137
taccaggcta aaggaggctg a 21

<210> SEQ ID NO 138
<211> LENGTH: 23
<212> TYPE: DNA
<213> ORGANISM: Blattella germanica

<400> SEQUENCE: 138
accaggctaa aggaggctga agc 23

<210> SEQ ID NO 139
<211> LENGTH: 21
<212> TYPE: DNA
<213> ORGANISM: Blattella germanica

<400> SEQUENCE: 139
gctaaaggag gctgaagctc g 21

<210> SEQ ID NO 140
<211> LENGTH: 29
<212> TYPE: DNA
<213> ORGANISM: Blattella germanica

<400> SEQUENCE: 140
ctaaaggagg ctgaagctcg tgctgagtt 29

<210> SEQ ID NO 141
<211> LENGTH: 32
<212> TYPE: DNA
<213> ORGANISM: Blattella germanica

<400> SEQUENCE: 141
aaggaggctg aagctcgtgc tgagttcgct ga 32

<210> SEQ ID NO 142
<211> LENGTH: 21
<212> TYPE: DNA
<213> ORGANISM: Blattella germanica

<400> SEQUENCE: 142
gctcgtgctg agttcgctga a 21

<210> SEQ ID NO 143
<211> LENGTH: 60
<212> TYPE: DNA
<213> ORGANISM: Blattella germanica

<400> SEQUENCE: 143
tgcagaagga ggttgacagg cttgaggatg aattggtaca cgagaaggag aagtacaagt 60

<210> SEQ ID NO 144
<211> LENGTH: 32
<212> TYPE: DNA
<213> ORGANISM: Blattella germanica

<400> SEQUENCE: 144
ttggtacacg agaaggagaa gtacaagtac at 32

<210> SEQ ID NO 145
<211> LENGTH: 53
<212> TYPE: DNA
<213> ORGANISM: Blattella germanica

<400> SEQUENCE: 145
gagaaggaga agtacaagta catttgtgac gatcttgata tgactttcac cga 53

<210> SEQ ID NO 146
<211> LENGTH: 23
<212> TYPE: DNA
<213> ORGANISM: Blattella germanica

<400> SEQUENCE: 146
aacagcaggc ccgcgacgcc aac 23

<210> SEQ ID NO 147
<211> LENGTH: 42
<212> TYPE: DNA
<213> ORGANISM: Blattella germanica

<400> SEQUENCE: 147
catttgtgac gatcttgata tgactttcac cgaacttatt gg 42

<210> SEQ ID NO 148
<211> LENGTH: 22
<212> TYPE: DNA
<213> ORGANISM: Blattella germanica

<400> SEQUENCE: 148
cggacaggga ggacatcaac tc 22

<210> SEQ ID NO 149
<211> LENGTH: 23
<212> TYPE: DNA
<213> ORGANISM: Blattella germanica

<400> SEQUENCE: 149
tggacaagtc gaagagcgtc aag 23

<210> SEQ ID NO 150
<211> LENGTH: 21
<212> TYPE: DNA
<213> ORGANISM: Blattella germanica

<400> SEQUENCE: 150
ctgctccaag atccagaaac a 21

<210> SEQ ID NO 151
<211> LENGTH: 44
<212> TYPE: DNA
<213> ORGANISM: Blattella germanica

<400> SEQUENCE: 151
gaggcccaga gcaagagagg tatcctcact ctgaagtacc ccat 44

<210> SEQ ID NO 152
<211> LENGTH: 23
<212> TYPE: DNA
<213> ORGANISM: Blattella germanica

<400> SEQUENCE: 152
gctccagagg aacacccaat cct 23

<210> SEQ ID NO 153
<211> LENGTH: 23
<212> TYPE: DNA
<213> ORGANISM: Blattella germanica

<400> SEQUENCE: 153
atcctgctga ctgaggctcc cct 23

<210> SEQ ID NO 154
<211> LENGTH: 47
<212> TYPE: DNA
<213> ORGANISM: Blattella germanica

<400> SEQUENCE: 154
aaggccaaca gggagaagat gactcaaatc atgtttgaga ccttcaa 47

<210> SEQ ID NO 155
<211> LENGTH: 29
<212> TYPE: DNA
<213> ORGANISM: Blattella germanica

<400> SEQUENCE: 155
caaatcatgt ttgagacctt caacacccc 29

<210> SEQ ID NO 156
<211> LENGTH: 37
<212> TYPE: DNA
<213> ORGANISM: Blattella germanica

<400> SEQUENCE: 156
tcatgtttga gaccttcaac acccccgcca tgtatgt 37

<210> SEQ ID NO 157
<211> LENGTH: 38
<212> TYPE: DNA
<213> ORGANISM: Blattella germanica

<400> SEQUENCE: 157
accttcaaca cccccgccat gtatgttgcc atccaggc 38

<210> SEQ ID NO 158
<211> LENGTH: 29
<212> TYPE: DNA

<213> ORGANISM: Blattella germanica

<400> SEQUENCE: 158
cccgccatgt atgttgccat ccaggccgt 29

<210> SEQ ID NO 159
<211> LENGTH: 23
<212> TYPE: DNA
<213> ORGANISM: Blattella germanica

<400> SEQUENCE: 159
gccatccagg ccgtgctgtc cct 23

<210> SEQ ID NO 160
<211> LENGTH: 30
<212> TYPE: DNA
<213> ORGANISM: Blattella germanica

<400> SEQUENCE: 160
tacgcttccg gccgtaccac tggtattgtg 30

<210> SEQ ID NO 161
<211> LENGTH: 23
<212> TYPE: DNA
<213> ORGANISM: Blattella germanica

<400> SEQUENCE: 161
gcttccggcc gtaccactgg tat 23

<210> SEQ ID NO 162
<211> LENGTH: 32
<212> TYPE: DNA
<213> ORGANISM: Blattella germanica

<400> SEQUENCE: 162
cgtaccactg gtattgtgct ggactctggt ga 32

<210> SEQ ID NO 163
<211> LENGTH: 26
<212> TYPE: DNA
<213> ORGANISM: Blattella germanica

<400> SEQUENCE: 163
ggtattgtgc tggactctgg tgacgg 26

<210> SEQ ID NO 164
<211> LENGTH: 23
<212> TYPE: DNA
<213> ORGANISM: Blattella germanica

<400> SEQUENCE: 164
ggtgacggcg tctcccacac cgt 23

<210> SEQ ID NO 165
<211> LENGTH: 23
<212> TYPE: DNA
<213> ORGANISM: Blattella germanica

<400> SEQUENCE: 165
ggtgacggcg tctcccacac cgt 23

<210> SEQ ID NO 166
<211> LENGTH: 32

<212> TYPE: DNA
<213> ORGANISM: Blattella germanica

<400> SEQUENCE: 166
tcccacaccg tacccatcta tgaaggttac gc 32

<210> SEQ ID NO 167
<211> LENGTH: 40
<212> TYPE: DNA
<213> ORGANISM: Blattella germanica

<400> SEQUENCE: 167
tgaagtaccc cattgaacat ggaatcatca ccaactggga 40

<210> SEQ ID NO 168
<211> LENGTH: 28
<212> TYPE: DNA
<213> ORGANISM: Blattella germanica

<400> SEQUENCE: 168
tgccccatgc catcctgcgt ctggactt 28

<210> SEQ ID NO 169
<211> LENGTH: 30
<212> TYPE: DNA
<213> ORGANISM: Blattella germanica

<400> SEQUENCE: 169
gccatcctgc gtctggactt ggccggccgt 30

<210> SEQ ID NO 170
<211> LENGTH: 29
<212> TYPE: DNA
<213> ORGANISM: Blattella germanica

<400> SEQUENCE: 170
cgtctggact tggccggccg tgacttgac 29

<210> SEQ ID NO 171
<211> LENGTH: 32
<212> TYPE: DNA
<213> ORGANISM: Blattella germanica

<400> SEQUENCE: 171
cgtgacttga ctgactacct gatgaagatc ct 32

<210> SEQ ID NO 172
<211> LENGTH: 36
<212> TYPE: DNA
<213> ORGANISM: Blattella germanica

<400> SEQUENCE: 172
gactacctga tgaagatcct gaccgagcgt ggctac 36

<210> SEQ ID NO 173
<211> LENGTH: 35
<212> TYPE: DNA
<213> ORGANISM: Blattella germanica

<400> SEQUENCE: 173
atgaagatcc tgaccgagcg tggctacagc ttcac 35

<210> SEQ ID NO 174

-continued

<211> LENGTH: 29
<212> TYPE: DNA
<213> ORGANISM: Blattella germanica

<400> SEQUENCE: 174
ggaatcatca ccaactggga tgacatgga 29

<210> SEQ ID NO 175
<211> LENGTH: 38
<212> TYPE: DNA
<213> ORGANISM: Blattella germanica

<400> SEQUENCE: 175
atcatcacca actgggatga catggagaag atctggca 38

<210> SEQ ID NO 176
<211> LENGTH: 35
<212> TYPE: DNA
<213> ORGANISM: Blattella germanica

<400> SEQUENCE: 176
gacatggaga agatctggca tcacaccttc tacaa 35

<210> SEQ ID NO 177
<211> LENGTH: 36
<212> TYPE: DNA
<213> ORGANISM: Blattella germanica

<400> SEQUENCE: 177
atggagaaga tctggcatca caccttctac aatgaa 36

<210> SEQ ID NO 178
<211> LENGTH: 35
<212> TYPE: DNA
<213> ORGANISM: Blattella germanica

<400> SEQUENCE: 178
aagatctggc atcacacctt ctacaatgaa ctccg 35

<210> SEQ ID NO 179
<211> LENGTH: 35
<212> TYPE: DNA
<213> ORGANISM: Blattella germanica

<400> SEQUENCE: 179
atctggcatc acaccttcta caatgaactc cgagt 35

<210> SEQ ID NO 180
<211> LENGTH: 26
<212> TYPE: DNA
<213> ORGANISM: Blattella germanica

<400> SEQUENCE: 180
aacgtgttca agaacaagcg tgtcct 26

<210> SEQ ID NO 181
<211> LENGTH: 31
<212> TYPE: DNA
<213> ORGANISM: Blattella germanica

<400> SEQUENCE: 181
catccacaag aagaaggctg agaaggccag g 31

<210> SEQ ID NO 182
<211> LENGTH: 41
<212> TYPE: DNA
<213> ORGANISM: Blattella germanica

<400> SEQUENCE: 182
gccatcaaga agaagatgca ggcgatgaag ctggagaagg a 41

<210> SEQ ID NO 183
<211> LENGTH: 24
<212> TYPE: DNA
<213> ORGANISM: Blattella germanica

<400> SEQUENCE: 183
cctgcagaag aagatccagc agat 24

<210> SEQ ID NO 184
<211> LENGTH: 32
<212> TYPE: DNA
<213> ORGANISM: Blattella germanica

<400> SEQUENCE: 184
aagatgcagg cgatgaagct ggagaaggac aa 32

<210> SEQ ID NO 185
<211> LENGTH: 21
<212> TYPE: DNA
<213> ORGANISM: Blattella germanica

<400> SEQUENCE: 185
gagaaggaca aggccctgca g 21

<210> SEQ ID NO 186
<211> LENGTH: 26
<212> TYPE: DNA
<213> ORGANISM: Blattella germanica

<400> SEQUENCE: 186
gttgtcggca acaacctgaa gtccct 26

<210> SEQ ID NO 187
<211> LENGTH: 23
<212> TYPE: DNA
<213> ORGANISM: Blattella germanica

<400> SEQUENCE: 187
aaggaggctg aagctcgtgc tga 23

<210> SEQ ID NO 188
<211> LENGTH: 27
<212> TYPE: DNA
<213> ORGANISM: Blattella germanica

<400> SEQUENCE: 188
gaggcccaga gcaagagagg tatcctc 27

<210> SEQ ID NO 189
<211> LENGTH: 23
<212> TYPE: DNA
<213> ORGANISM: Blattella germanica

<400> SEQUENCE: 189
cagagcaaga gaggtatcct cac 23

```
<210> SEQ ID NO 190
<211> LENGTH: 34
<212> TYPE: DNA
<213> ORGANISM: Blattella germanica

<400> SEQUENCE: 190

gcccagagca agagaggtat cctcactctg aagt                              34


<210> SEQ ID NO 191
<211> LENGTH: 23
<212> TYPE: DNA
<213> ORGANISM: Blattella germanica

<400> SEQUENCE: 191

aaggccaaca gggagaagat gac                                          23


<210> SEQ ID NO 192
<211> LENGTH: 23
<212> TYPE: DNA
<213> ORGANISM: Blattella germanica

<400> SEQUENCE: 192

gagaagatga ctcaaatcat gtt                                          23


<210> SEQ ID NO 193
<211> LENGTH: 29
<212> TYPE: DNA
<213> ORGANISM: Blattella germanica

<400> SEQUENCE: 193

ggtatcctca ctctgaagta ccccattga                                    29


<210> SEQ ID NO 194
<211> LENGTH: 21
<212> TYPE: DNA
<213> ORGANISM: Blattella germanica

<400> SEQUENCE: 194

atcatgtttg agaccttcaa c                                            21


<210> SEQ ID NO 195
<211> LENGTH: 26
<212> TYPE: DNA
<213> ORGANISM: Blattella germanica

<400> SEQUENCE: 195

gagaccttca acacccccgc catgta                                       26


<210> SEQ ID NO 196
<211> LENGTH: 23
<212> TYPE: DNA
<213> ORGANISM: Blattella germanica

<400> SEQUENCE: 196

gccatccagg ccgtgctgtc cct                                          23


<210> SEQ ID NO 197
<211> LENGTH: 35
<212> TYPE: DNA
<213> ORGANISM: Blattella germanica

<400> SEQUENCE: 197

gtctcccaca ccgtacccat ctatgaaggt tacgc                             35
```

-continued

```
<210> SEQ ID NO 198
<211> LENGTH: 40
<212> TYPE: DNA
<213> ORGANISM: Blattella germanica

<400> SEQUENCE: 198

tcaccaactg ggatgacatg gagaagatct ggcatcacac                          40


<210> SEQ ID NO 199
<211> LENGTH: 35
<212> TYPE: DNA
<213> ORGANISM: Blattella germanica

<400> SEQUENCE: 199

gacatggaga agatctggca tcacaccttc tacaa                               35


<210> SEQ ID NO 200
<211> LENGTH: 41
<212> TYPE: DNA
<213> ORGANISM: Blattella germanica

<400> SEQUENCE: 200

atggagaaga tctggcatca caccttctac aatgaactcc g                        41
```